(12) United States Patent
Walker et al.

(10) Patent No.: US 11,044,967 B2
(45) Date of Patent: Jun. 29, 2021

(54) FOOT PRESENCE SENSING USING MAGNETS IN FOOTWEAR

(71) Applicant: NIKE, Inc., Beaverton, OR (US)

(72) Inventors: Steven H. Walker, Camas, WA (US); Phillip Meneau, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 672 days.

(21) Appl. No.: 15/459,402

(22) Filed: Mar. 15, 2017

(65) Prior Publication Data
US 2017/0265584 A1  Sep. 21, 2017

Related U.S. Application Data

(60) Provisional application No. 62/308,657, filed on Mar. 15, 2016, provisional application No. 62/308,667, (Continued)

(51) Int. Cl.
*A43C 11/16* (2006.01)
*A43C 11/00* (2006.01)
(Continued)

(52) U.S. Cl.
CPC .......... *A43C 11/165* (2013.01); *A43B 1/0054* (2013.01); *A43B 3/001* (2013.01);
(Continued)

(58) Field of Classification Search
CPC ......... A43C 11/165; A43C 1/00; A43C 1/003; A43C 1/006; A43C 1/02; A43C 1/04;
(Continued)

(56) References Cited

U.S. PATENT DOCUMENTS

| 4,152,748 A | 5/1979 | Arkans |
| 4,922,634 A * | 5/1990 | Seidel .................. A43B 5/0449 36/117.8 |

(Continued)

FOREIGN PATENT DOCUMENTS

| CN | 1813603 A | 8/2006 |
| CN | 101217894 | 7/2008 |

(Continued)

OTHER PUBLICATIONS

"U.S. Appl. No. 16/280,732, Non Final Office Action dated Mar. 27, 2019", 7 pgs.
(Continued)

*Primary Examiner* — Alissa J Tompkins
*Assistant Examiner* — Dakota Marin
(74) *Attorney, Agent, or Firm* — Schwegman Lundberg & Woessner, P.A.

(57) ABSTRACT

An article of footwear can include a ferromagnetic body disposed in the article, and a magnetometer to measure a strength or direction of a magnetic field that is influenced by a position of the ferromagnetic body. One of the ferromagnetic body and the magnetometer can be configured to move relative to the other one of the ferromagnetic body and the magnetometer, for example according to movement of a foot in the article. In an example, the ferromagnetic body is disposed in a compressible insole and the ferromagnetic body moves in response to compression or relaxation of the insole. The magnetometer can be disposed in a platform or sole portion of the article that is relatively stationary compared to the ferromagnetic body. Rate of change information about the magnetic field can be used to control article functions or to provide information about a foot strike or step rate.

20 Claims, 50 Drawing Sheets

Related U.S. Application Data filed on Mar. 15, 2016, provisional application No. 62/424,939, filed on Nov. 21, 2016, provisional application No. 62/424,959, filed on Nov. 21, 2016.

(51) Int. Cl.
| | |
|---|---|
| A61B 5/00 | (2006.01) |
| G01D 5/12 | (2006.01) |
| G01L 1/14 | (2006.01) |
| A43B 1/00 | (2006.01) |
| A43B 3/00 | (2006.01) |
| G01L 5/12 | (2006.01) |
| G01L 5/24 | (2006.01) |
| A43B 13/14 | (2006.01) |
| A43B 17/00 | (2006.01) |
| A43C 1/00 | (2006.01) |
| G01D 5/24 | (2006.01) |
| G05B 15/02 | (2006.01) |
| A43C 7/00 | (2006.01) |
| G01L 1/12 | (2006.01) |
| G05B 19/048 | (2006.01) |
| G01D 5/14 | (2006.01) |
| G01D 5/34 | (2006.01) |
| A43C 1/04 | (2006.01) |
| A43C 1/06 | (2006.01) |
| A43C 1/02 | (2006.01) |

(52) U.S. Cl.
CPC .......... *A43B 3/0005* (2013.01); *A43B 3/0031* (2013.01); *A43B 13/14* (2013.01); *A43B 17/00* (2013.01); *A43C 1/00* (2013.01); *A43C 7/00* (2013.01); *A43C 11/008* (2013.01); *A61B 5/6807* (2013.01); *G01D 5/12* (2013.01); *G01D 5/24* (2013.01); *G01L 1/12* (2013.01); *G01L 1/144* (2013.01); *G01L 5/12* (2013.01); *G01L 5/24* (2013.01); *G05B 15/02* (2013.01); *G05B 19/048* (2013.01); *A43B 3/0015* (2013.01); *A43C 1/003* (2013.01); *A43C 1/006* (2013.01); *A43C 1/02* (2013.01); *A43C 1/04* (2013.01); *A43C 1/06* (2013.01); *A43C 11/00* (2013.01); *G01D 5/145* (2013.01); *G01D 5/2405* (2013.01); *G01D 5/34* (2013.01); *G05B 2219/24015* (2013.01)

(58) Field of Classification Search
CPC ........... A43C 1/06; A43C 7/00; A43C 11/008; A43C 11/00; A43B 1/0054; A43B 3/0005; A43B 3/0015; A43B 3/001; A43B 3/0031; A43B 13/14; A43B 17/00; A61B 5/6807; G01L 1/12; G01L 1/144; G01L 5/12; G01L 5/24; G01D 5/12; G01D 5/24; G01D 5/145; G01D 5/2405; G01D 5/34; G01D 19/048; G01D 2219/24015
USPC ........................................................ 36/50.1
See application file for complete search history.

(56) References Cited

U.S. PATENT DOCUMENTS

| | | | |
|---|---|---|---|
| 5,343,190 A * | 8/1994 | Rodgers ............... | A43B 1/0036 200/61.45 R |
| 5,662,123 A | 9/1997 | Goldman | |
| 5,791,068 A * | 8/1998 | Bernier ............... | A43B 1/0072 36/50.1 |
| 5,929,332 A | 7/1999 | Brown | |
| 6,032,387 A | 3/2000 | Johnson | |
| 6,033,370 A | 3/2000 | Reinbold et al. | |
| 6,195,921 B1 | 3/2001 | Truong | |
| 6,199,303 B1 | 3/2001 | Luthi et al. | |
| 6,301,964 B1 | 10/2001 | Fyfe et al. | |
| 6,305,221 B1 | 10/2001 | Hutchings | |
| 6,427,361 B1 * | 8/2002 | Chou ..................... | A43B 11/00 36/138 |
| 6,513,381 B2 | 2/2003 | Fyfe et al. | |
| 6,643,954 B2 | 11/2003 | Voswinkel | |
| 6,691,433 B2 * | 2/2004 | Liu ....................... | A43B 3/0005 24/68 SK |
| 6,896,128 B1 * | 5/2005 | Johnson ................ | A43C 1/06 36/118.1 |
| 6,898,299 B1 | 5/2005 | Brooks | |
| 7,032,448 B2 | 4/2006 | Hamamoto | |
| 7,310,895 B2 | 12/2007 | Whittlesey et al. | |
| 7,331,126 B2 * | 2/2008 | Johnson ................ | A43B 11/00 36/118.1 |
| 7,355,519 B2 | 4/2008 | Grold et al. | |
| 7,487,606 B2 * | 2/2009 | Koo ...................... | A43B 1/0054 36/141 |
| 7,506,460 B2 * | 3/2009 | DiBenedetto ........ | A43B 1/0054 36/1 |
| 7,552,549 B2 * | 6/2009 | Whittlesey ........... | A43B 3/0005 36/127 |
| 7,614,166 B2 | 11/2009 | Vick et al. | |
| 7,676,957 B2 * | 3/2010 | Johnson ................ | A43B 11/00 36/50.1 |
| 7,712,373 B2 | 5/2010 | Nagle et al. | |
| 7,752,774 B2 * | 7/2010 | Ussher ................. | A43B 3/0005 36/100 |
| 7,793,430 B2 | 9/2010 | Ellis | |
| 7,827,000 B2 | 11/2010 | Stirling et al. | |
| 7,911,339 B2 | 3/2011 | Vock | |
| 7,912,672 B2 | 3/2011 | Feichtinger et al. | |
| 8,028,443 B2 | 10/2011 | Case, Jr. | |
| 8,046,937 B2 * | 11/2011 | Beers ................... | A43B 3/0005 36/50.1 |
| 8,480,541 B1 | 7/2013 | Brunts | |
| 8,522,456 B2 | 9/2013 | Beers et al. | |
| 8,581,731 B2 | 11/2013 | Purks et al. | |
| 8,676,541 B2 | 3/2014 | Schrock et al. | |
| 8,739,639 B2 | 6/2014 | Owings et al. | |
| 8,752,200 B2 | 6/2014 | Varshavsky et al. | |
| 8,769,844 B2 | 7/2014 | Beers et al. | |
| 8,904,673 B2 * | 12/2014 | Johnson ................ | A43B 11/00 36/50.1 |
| 8,935,860 B2 * | 1/2015 | Torres .................. | A43B 3/0005 36/138 |
| 9,063,182 B2 | 6/2015 | Lombardi et al. | |
| 9,095,251 B2 | 8/2015 | Purks et al. | |
| 9,322,121 B2 | 4/2016 | Dunne et al. | |
| 9,591,891 B1 | 3/2017 | Baucom et al. | |
| 9,907,359 B2 * | 3/2018 | Beers ..................... | A43C 11/00 |
| 10,172,423 B2 | 1/2019 | Walker et al. | |
| 10,448,707 B2 | 10/2019 | Walker et al. | |
| 10,477,923 B2 | 11/2019 | Walker et al. | |
| 10,499,711 B2 | 12/2019 | Walker et al. | |
| 10,722,000 B2 | 7/2020 | Walker et al. | |
| 10,758,012 B2 | 9/2020 | Walker et al. | |
| 2005/0183292 A1 * | 8/2005 | DiBenedetto ........ | A43B 3/0005 36/132 |
| 2005/0198867 A1 * | 9/2005 | Labbe .................. | A43C 11/00 36/50.1 |
| 2006/0230642 A1 | 10/2006 | Vick et al. | |
| 2007/0000154 A1 | 1/2007 | Dibenedetto et al. | |
| 2007/0006489 A1 * | 1/2007 | Case, Jr. ............. | A43B 3/0005 36/132 |
| 2007/0011919 A1 | 1/2007 | Case, Jr. | |
| 2007/0180736 A1 | 8/2007 | Dibenedetto et al. | |
| 2007/0209234 A1 * | 9/2007 | Chou .................... | A43B 11/00 36/50.1 |
| 2007/0240334 A1 | 10/2007 | Johnson | |
| 2008/0060224 A1 | 3/2008 | Whittlesey et al. | |
| 2008/0086911 A1 * | 4/2008 | Labbe .................. | A43B 11/00 36/50.1 |
| 2009/0071805 A1 | 3/2009 | Horning et al. | |
| 2009/0102669 A1 | 4/2009 | Lin | |
| 2009/0113762 A1 | 5/2009 | Leimer et al. | |
| 2009/0272007 A1 | 11/2009 | Beers et al. | |

(56) References Cited

U.S. PATENT DOCUMENTS

| | | |
|---|---|---|
| 2010/0004566 A1 | 1/2010 | Son et al. |
| 2010/0063778 A1 | 3/2010 | Schrock et al. |
| 2010/0184563 A1 | 7/2010 | Molyneux et al. |
| 2010/0199524 A1 | 8/2010 | Grun et al. |
| 2010/0201650 A1 | 8/2010 | Son |
| 2010/0253645 A1 | 10/2010 | Bolender |
| 2011/0050251 A1 | 3/2011 | Franke et al. |
| 2011/0054359 A1 | 3/2011 | Sazonov et al. |
| 2011/0276112 A1 | 11/2011 | Simon et al. |
| 2011/0304497 A1 | 12/2011 | Molyneux et al. |
| 2012/0041767 A1 | 2/2012 | Hoffman et al. |
| 2012/0062248 A1 | 3/2012 | Lee et al. |
| 2012/0068760 A1 | 3/2012 | Caldwell et al. |
| 2012/0217982 A1 | 8/2012 | Narayanasamy et al. |
| 2012/0247919 A1 | 10/2012 | Soldner et al. |
| 2012/0291563 A1 | 11/2012 | Schrock et al. |
| 2012/0291564 A1 | 11/2012 | Amos et al. |
| 2012/0304500 A1 | 12/2012 | Bove |
| 2013/0019503 A1 | 1/2013 | Vogt |
| 2013/0086997 A1 | 4/2013 | Tanhua et al. |
| 2013/0147752 A1 | 6/2013 | Simmons et al. |
| 2013/0185961 A1 | 7/2013 | Tseng et al. |
| 2013/0190903 A1 | 7/2013 | Balakrishnan et al. |
| 2013/0213144 A1 | 8/2013 | Rice et al. |
| 2013/0293244 A1 | 11/2013 | Leek |
| 2014/0062703 A1 | 3/2014 | Purks et al. |
| 2014/0135954 A1 | 5/2014 | Vranish |
| 2014/0165427 A1 | 6/2014 | Molyneux et al. |
| 2014/0213843 A1 | 7/2014 | Pilla et al. |
| 2014/0221726 A1 | 8/2014 | Pilla et al. |
| 2014/0260689 A1* | 9/2014 | Walker .................. G01L 1/2206 73/862.625 |
| 2014/0360047 A1 | 12/2014 | Beers et al. |
| 2015/0018721 A1 | 1/2015 | Wang et al. |
| 2015/0100245 A1 | 4/2015 | Huang et al. |
| 2015/0237183 A1 | 8/2015 | Novet |
| 2015/0257679 A1 | 9/2015 | Ross |
| 2015/0272264 A1 | 10/2015 | Lee |
| 2015/0276963 A1 | 10/2015 | Casimiro et al. |
| 2015/0289594 A1 | 10/2015 | Rushbrook et al. |
| 2015/0290496 A1 | 10/2015 | Purks et al. |
| 2015/0296922 A1 | 10/2015 | Rushbrook et al. |
| 2015/0309563 A1 | 10/2015 | Connor |
| 2015/0359457 A1 | 12/2015 | Blumenthal et al. |
| 2016/0074547 A1 | 3/2016 | Dobrinsky et al. |
| 2016/0084487 A1 | 3/2016 | Chacon et al. |
| 2016/0106177 A1 | 4/2016 | De Laurentis |
| 2016/0124573 A1 | 5/2016 | Rouaissia et al. |
| 2017/0002254 A1 | 1/2017 | Haque et al. |
| 2017/0049190 A1* | 2/2017 | Maussen .............. A43C 11/165 |
| 2017/0176266 A1 | 6/2017 | Mathieu et al. |
| 2017/0265582 A1 | 9/2017 | Walker et al. |
| 2017/0265583 A1 | 9/2017 | Schneider et al. |
| 2017/0265587 A1 | 9/2017 | Walker et al. |
| 2017/0265588 A1 | 9/2017 | Walker et al. |
| 2017/0265589 A1 | 9/2017 | Walker et al. |
| 2017/0265594 A1 | 9/2017 | Walker et al. |
| 2017/0273849 A1 | 9/2017 | Oleson et al. |
| 2018/0199674 A1 | 7/2018 | Walker et al. |
| 2018/0256071 A1 | 9/2018 | Mathieu et al. |
| 2018/0289110 A1 | 10/2018 | Bock et al. |
| 2018/0368526 A1 | 12/2018 | Bock et al. |
| 2019/0166954 A1 | 6/2019 | Walker et al. |
| 2019/0174871 A1 | 6/2019 | Walker et al. |
| 2019/0208865 A1 | 7/2019 | Walker et al. |
| 2019/0373986 A1 | 12/2019 | Walker et al. |
| 2019/0387840 A1 | 12/2019 | Walker et al. |
| 2020/0046081 A1 | 2/2020 | Walker et al. |
| 2020/0077749 A1 | 3/2020 | Walker et al. |
| 2020/0352284 A1 | 11/2020 | Walker et al. |

FOREIGN PATENT DOCUMENTS

| | | |
|---|---|---|
| CN | 101951798 | 1/2011 |
| CN | 102014682 | 4/2011 |
| CN | 102308270 A | 1/2012 |
| CN | 102972100 | 3/2013 |
| CN | 103476283 A | 12/2013 |
| CN | 103476284 A | 12/2013 |
| CN | 103608752 | 2/2014 |
| CN | 203505737 | 4/2014 |
| CN | 203762364 U | 8/2014 |
| CN | 104337105 A | 2/2015 |
| CN | 104582519 | 4/2015 |
| CN | 104619207 | 5/2015 |
| CN | 204561139 U | 8/2015 |
| CN | 205568006 U | 9/2016 |
| CN | 106455747 A | 2/2017 |
| CN | 109152445 A | 1/2019 |
| CN | 109152446 A | 1/2019 |
| CN | 109152447 A | 1/2019 |
| CN | 109152448 A | 1/2019 |
| CN | 109414092 | 3/2019 |
| CN | 110621186 | 12/2019 |
| CN | 109152445 | 10/2020 |
| DE | 3900777 | 7/1990 |
| EP | 1447653 | 8/2004 |
| EP | 1457128 | 9/2004 |
| EP | 3429416 | 1/2019 |
| JP | 2004267784 | 9/2004 |
| JP | 2005279281 | 10/2005 |
| JP | 2006349478 | 12/2006 |
| JP | 2008229372 | 10/2008 |
| JP | 2008546500 A | 12/2008 |
| JP | 2009500141 | 1/2009 |
| JP | 201450760 | 5/2010 |
| JP | 2011519611 | 7/2011 |
| JP | 2015057598 | 3/2015 |
| JP | 2019508168 | 3/2019 |
| JP | 2019508178 | 3/2019 |
| JP | 2019512322 | 5/2019 |
| JP | 2019512323 | 5/2019 |
| JP | 2019512325 | 5/2019 |
| JP | 2020509875 | 4/2020 |
| JP | 2020203115 | 12/2020 |
| KR | 20190131515 | 11/2019 |
| KR | 20200075904 A | 6/2020 |
| KR | 102141214 B1 | 8/2020 |
| TW | 521593 | 2/2003 |
| TW | 201739371 | 11/2017 |
| WO | 2007008352 | 1/2007 |
| WO | 2009071652 | 6/2009 |
| WO | WO-2014100045 A1 | 6/2014 |
| WO | 2014188350 | 11/2014 |
| WO | 2015163982 | 10/2015 |
| WO | 2017160865 | 9/2017 |
| WO | 2017160969 | 9/2017 |
| WO | 2017161000 | 9/2017 |
| WO | 2017161014 | 9/2017 |
| WO | 2017161037 | 9/2017 |
| WO | 2017161000 | 8/2018 |
| WO | WO-2018170148 A2 | 9/2018 |
| WO | WO-2020186171 A1 | 9/2020 |

OTHER PUBLICATIONS

"U.S. Appl. No. 15/458,625, Examiner Interview Summary dated Mar. 27, 2019", 3 pgs.

"U.S. Appl. No. 15/460,060, Non Final Office Action dated Apr. 18, 2019", 32 pgs.

"U.S. Appl. No. 15/458,625, Respnse filed May 8, 2019 to Final Office Action dated Feb. 8, 2019", 13 pgs.

"European Application Serial No. 17767355.5, Response filed Apr. 24, 2019 to Communication Pursuant to Rules 161 and 162 dated Oct. 30, 2018", 10 pgs.

"European Application Serial No. 17767469.4, Response filed Apr. 24, 2019 to Communication Pursuant to Rules 161 and 162 dated Nov. 5, 2018", 12 pgs.

(56) References Cited

OTHER PUBLICATIONS

"U.S. Appl. No. 15/610,179, Notice of Allowance dated May 15, 2019", 12 pgs.
"European Application Serial No. 17767442.1, Response filed Apr. 26, 2019 to Communication Pursuant to Rules 161 and 162 dated Oct. 24, 2018", 11 pgs.
"European Application Serial No. 17767453.8, Response filed Apr. 26, 2019 to Communication Pursuant to Rules 161 and 162 dated Oct. 24, 2018", 13 pgs.
"U.S. Appl. No. 16/280,732, Examiner Interview Summary dated Jun. 7, 2019", 3 pgs.
"U.S. Appl. No. 15/458,625, Response filed Jun. 21, 2019 to Final Office Action dated Feb. 8, 2019", 14 pgs.
"U.S. Appl. No. 15/458,625, Advisory Action dated Jun. 26, 2019", 4 pgs.
"U.S. Appl. No. 16/280,732, Response Filed Jun. 26, 2019 to Non Final Office Action dated Mar. 27, 2019", 11 pgs.
"Chinese Application Serial No. 201780029822.4, Voluntary Amendment filed Jul. 4, 2019", w English claims, 11 pgs.
"U.S. Appl. No. 16/280,732, Notice of Allowance dated Jul. 17, 2019", 5 pgs.
"U.S. Appl. No. 15/458,625, Notice of Allowance dated Aug. 7, 2019", 12 pgs.
"Chinese Application Serial No. 201780029824.3, Voluntary Amendment filed Jul. 4, 2019", w English claims, 15 pgs.
"U.S. Appl. No. 15/610,179, 312 Amendment filed Aug. 15, 2019", 6 pgs.
Bamberg, Stacy J, "Development of a Quantitative In-Show Measurement System for Assessing Balance: Sixteen-Sensor Insoles", (2006).
Kothari, M, "Capacitive Sensors for Measuring the Pressure between the Foot and Shoe", IEEE, (1988).
Morris, Stacy J, "A Shoe-Integrated Sensor System for Wireless Gait Analysis and Real-Time Therapeutic Feedback, dissertation", Massachusetts Institute of Technology, MA, (2004), 1-314.
Sumiya, Tadashi, "Sensing Stability and Dynamic Response of the F-Scan in-Shoe Sensing System: A Technical Note", (1988).
Takahashi, Youhei, "Six-axis Force Sensing Footwear for National Walking Analysis", (2004).
Zhou, Chenming, "A Shoe-Embedded RF Sensor for Motion Detection", IEEE, (2011).
"U.S. Appl. No. 15/610,179, Response filed May 15, 2018 to Non Final Office Action dated Feb. 15, 2018", 19 pgs.
"U.S. Appl. No. 15/458,625, Response Filed May 29, 2018 to Restriction Requirement dated Apr. 5, 2018", 8 pgs.
"U.S. Appl. No. 15/458,625, Response filed Oct. 26, 2018 to Non Final Office Action dated Jul. 27, 2018", 11 pgs.
"U.S. Appl. No. 15/459,889, Examiner Interview Summary dated Oct. 9, 2018", 3 pgs.
"U.S. Appl. No. 15/459,889, Response filed Oct. 9, 2018 to Non Final Office Action dated Jun. 26, 2018", 17 pgs.
"U.S. Appl. No. 15/459,897, Restriction Requirement dated Sep. 10, 2018", 6 pgs.
"U.S. Appl. No. 15/610,179, Advisory Action dated Oct. 12, 2018", 3 pgs.
"U.S. Appl. No. 15/610,179, Response filed Oct. 4, 2018 to Final Office Action dated Aug. 6, 2018", 15 pgs.
"International Application Serial No. PCT/US2017/022489, International Preliminary Report on Patentability dated Sep. 27, 2018", 10 pgs.
"International Application Serial No. PCT/US2017/022548, International Preliminary Report on Patentability dated Sep. 27, 2018", 11 pgs.
"International Application Serial No. PCT/US2017/022576, International Preliminary Report on Patentability dated Sep. 27, 2018", 9 pgs.
"International Application Serial No. PCT/US2018/022466, International Search Report dated Oct. 16, 2018", 6 pgs.
"International Application Serial No. PCT/US2018/022466, Written Opinion dated Oct. 16, 2018", 6 pgs.
"U.S. Appl. No. 16/685,081, Non Final Office Action dated Jan. 3, 2020", 7 pgs.
"U.S. Appl. No. 15/459,897, Response filed Jan. 3, 2020 to Non Final Office Action dated Oct. 3, 2019", 15 pgs.
"U.S. Appl. No. 16/197,905, Non Final Office Action dated Jan. 6, 2020", 6 pgs.
"Korean Application Serial No. 10-2019-7030148, Office Action dated Dec. 20, 2019", w English translation, 6 pgs.
"U.S. Appl. No. 15/460,060, Response filed Jan. 30, 2020 to Non Final Office Action dated Oct. 30, 2019", 15 pgs.
"U.S. Appl. No. 16/685,081, Examiner Interview Summary dated Feb. 18, 2020".
"Japanese Application Serial No. 2019-550628, Voluntary Amendment filed Nov. 7, 2019", w English claims, voluntary amendment and PPH Request, 88 pgs.
"Korean Application Serial No. 10-2019-7030148, Voluntary Amendment filed Nov. 18, 2019", w English claims, PPH Request Voluntary Amendment, 13 pgs.
"U.S. Appl. No. 15/460,060, Non Final Office Action dated Oct. 30, 2019", 43 pgs.
"U.S. Appl. No. 15/459,897, Examiner Interview Summary dated Nov. 6, 2019", 3 pgs.
"European Application Serial No. 17767355.5, Extended European Search Report dated Nov. 7, 2019", 7 pgs.
"European Application Serial No. 17767469.4, Extended European Search Report dated Nov. 12, 2019", 8 pgs.
"European Application Serial No. 17767453.8, Extended European Search Report dated Nov. 18, 2019", 9 pgs.
"Chinese Application Serial No. 201780029824.3, Office Action dated Oct. 24, 2019", w English Translation, 13 pgs.
"U.S. Appl. No. 15/460,060, Examiner Interview Summary dated Nov. 26, 2019", 4 pgs.
"U.S. Appl. No. 16/311,813, Non Final Office Action dated Dec. 9, 2019", 16 pgs.
"U.S. Appl. No. 15/610,179, Restriction Requirement dated Sep. 11, 2017", 10 pgs.
"U.S. Appl. No. 15/610,179, Response filed Nov. 9, 2017 to Restriction Requirement dated Sep. 11, 2017", 9 pgs.
"International Application Serial No. PCT/US2017/022342, International Search Report dated Jun. 20, 2017", 4 pgs.
"International Application Serial No. PCT/US2017/022342, Written Opinion dated Jun. 20, 2017", 9 pgs.
"International Application Serial No. PCT/US2017/022489, International Search Report dated Jun. 20, 2017", 4 pgs.
"International Application Serial No. PCT/US2017/022489, Written Opinion dated Jun. 20, 2017", 8 pgs.
"International Application Serial No. PCT/US2017/022533, International Search Report dated Jun. 26, 2017", 4 pgs.
"International Application Serial No. PCT/US2017/022533, Written Opinion dated Jun. 26, 2017", 9 pgs.
"International Application Serial No. PCT/US2017/022548, International Search Report dated Jun. 28, 2017", 3 pgs.
"International Application Serial No. PCT/US2017/022548, Written Opinion dated Jun. 28, 2017", 9 pgs.
"International Application Serial No. PCT/US2017/022576, International Search Report dated Jun. 28, 2017", 3 pgs.
"International Application Serial No. PCT/US2017/022576, Written Opinion dated Jun. 28, 2017", 7 pgs.
"U.S. Appl. No. 15/458,625, Final Office Action dated Feb. 8, 2019", 16 pgs.
"U.S. Appl. No. 16/197,905, Preliminary Amendment filed Feb. 19, 2019", 6 pgs.
"European Application Serial No. 17767420.7, Response Filed Feb. 1, 2019 to Communication pursuant to Rules 161(2) and 162 EPC dated Nov. 2, 2019", 13 pgs.
"U.S. Appl. No. 15/459,889, Non Final Office Action dated Jun. 26, 2018", 12 pgs.
"International Application Serial No. PCT US2017 022533, International Preliminary Report on Patentability dated Jul. 3, 2018", 7 pgs.
"U.S. Appl. No. 15/458,625, Non Final Office Action dated Jul. 27, 2018", 15 pgs.

(56) References Cited

OTHER PUBLICATIONS

"International Application Serial No. PCT US2017 022342, International Preliminary Report on Patentability dated Jul. 3, 2018", 8 pgs.
"U.S. Appl. No. 15/610,179, Final Office Action dated Aug. 6, 2018", 32 pgs.
"U.S. Appl. No. 15/458,625, Restriction Requirement dated Apr. 5, 2018", 5 pgs.
"Taiwanese Application Serial No. 106108511, Office Action dated Dec. 5, 2017", w English translation, 16 pgs.
"U.S. Appl. No. 15/610,179, Non Final Office Action dated Feb. 15, 2018", 38 pgs.
"International Application Serial No. PCT US2018 022466, International Preliminary Report on Patentability dated Sep. 26, 2019", 8 pgs.
"U.S. Appl. No. 15/459,897, Non Final Office Action dated Oct. 3, 2019", 46 pgs.
"U.S. Appl. No. 15/459,889, Notice of Allowance dated Nov. 15, 2018",5 pgs.
"U.S. Appl. No. 15/459,897, Response filed Nov. 9, 2018to Restriction Requirement dated Sep. 10, 2018", 8 pgs.
"U.S. Appl. No. 15/460,060, Response filed Feb. 1, 2019 to Restriction Requirement dated Dec. 3, 2018", 8 pgs.
"U.S. Appl. No. 15/460,060, Restriction Requirement dated Dec. 3, 2018", 7 pgs.
"European Application Serial No. 17767420.7, Extended European Search Report dated Mar. 11, 2020", 7 pgs.
"Chinese Application Serial No. 201780029822.4, Office Action dated Feb. 14, 2020", w English Translation, 10 pgs.
"European Application Serial No. 18768014.5, Extended European Search Report dated Mar. 18, 2020", 7 pgs.
"Chinese Application Serial No. 201780029824.3, Response filed Mar. 29, 2020 to Office Action dated Oct. 24, 2019", w English claims, 66 pgs.
"Korean Application Serial No. 10-2019-7030148, Response filed Mar. 10, 2020 to Office Action dated Dec. 20, 2019", w English claims, 18 pgs.
"U.S. Appl. No. 15/459,897, Final Office Action dated Apr. 14, 2020", 49 pgs.
"U.S. Appl. No. 16/685,081, Notice of Allowance dated Apr. 15, 2020", 6 pgs.
"U.S. Appl. No. 15/921,414, Non Final Office Action dated Apr. 16, 2020", 51 pgs.
"Japanese Application Serial No. 2019-550628, Notification of Reasons for Refusal dated Apr. 21, 2020", w English translation, 4 pgs.
"U.S. Appl. No. 15/460,060, Final Office Action dated May 6, 2020", 42 pgs.
"U.S. Appl. No. 16/197,905, Response filed May 6, 2020 to Non Final Office Action dated Jan. 6, 2020", 7 pgs.
"European Application Serial No. 17767355.5, Response filed Apr. 30, 2020 to Extended European Search Report dated Nov. 7, 2019", 16 pgs.
"U.S. Appl. No. 16/311,813, Response filed May 8, 2020 to Non Final Office Action dated Dec. 9, 2019", 17 pgs.
"U.S. Appl. No. 16/311,813, Final Office Action dated May 19, 2020", 25 pgs.
"U.S. Appl. No. 16/197,905, Notice of Allowance dated May 22, 2020", 5 pgs.
"European Application Serial No. 17767453.8, Response filed May 13, 2020 to Extended European Search Report dated Nov. 18, 2019", 21 pgs.
"Chinese Application Serial No. 201780029824.3, Office Action dated May 12, 2020", w English translation, 8 pgs.
"European Application Serial No. 17767469.4, Response filed May 22, 2020 to Extended European Search Report dated Nov. 12, 2019", 14 pgs.
"U.S. Appl. No. 15/459,897, Response filed Jun. 15, 2020 to Final Office Action dated Apr. 14, 2020", 14 pgs.

"U.S. Appl. No. 15/459,897, Advisory Action dated Jun. 24, 2020", 3 pgs.
"Japanese Application Serial No. 2019-550628, Response filed Jun. 18, 2020 to Notification of Reasons for Refusal dated Apr. 21, 2020", w English claims, 15 pgs.
"U.S. Appl. No. 15/460,060, Response filed Jul. 6, 2020 to Final Office Action dated May 6, 2020", 16 pgs.
"U.S. Appl. No. 15/921,414, Response filed Nov. 3, 2020 to Final Office Action dated Sep. 3, 2020", 14 pgs.
"European Application Serial No. 18768014.5, Response flied Oct. 5, 2020 to Extended European Search Report dated Mar. 18, 2020", 14 pgs.
"U.S. Appl. No. 15/921,414, Advisory Action dated Nov. 19, 2020", 5 pgs.
"Chinese Application Serial No. 201780023316.3, Response filed Nov. 12, 2020 to Office Action dated Jul. 14, 2020", w English claims, 20 pgs.
"U.S. Appl. No. 15/921,414, Response filed Dec. 3, 2020 to Advisory Action dated Nov. 19, 2020", 14 pgs.
Morere, Clara Sanz, "MEMS Technology Sensors as a More Advantageous Technique for Measuring Foot Plantar Pressure and Balance in Humans", (Jan. 2016), 9 pgs.
"U.S. Appl. No. 16/353,739, Response filed Jan. 22, 2021 to Non Final Office Action dated Aug. 27, 2020", 15 pgs
"Korean Application Serial No. 10-2018-7029261, Notice of Preliminary Rejection dated Jan. 1, 2021", w English translation, 19 pgs.
"Korean Application Serial No. 10-2018-7029439, Notice of Preliminary Rejection dated Jan. 5, 2021", w English translation, 5 pgs.
"U.S. Appl. No. 16/311,813, Notice of Allowance dated Feb. 5, 2021", 18 pgs.
"U.S. Appl. No. 15/460,060, Advisory Action dated Jul. 15, 2020", 3 pgs.
"U.S. Appl. No. 15/921,414, Final Office Action dated Sep. 3, 2020", 54 pgs.
"U.S. Appl. No. 15/921,414, Response filed Jul. 16, 2020 to Non Final Office Action dated Apr. 16, 2020", 13 pgs.
"U.S. Appl. No. 16/311,813, Notice of Allowance dated Oct. 16, 2020", 14 pgs.
"U.S. Appl. No. 16/311,813, Pre-Appeal Brief Request filed Aug. 18, 2020".
"U.S. Appl. No. 16/353,739, Non Final Office Action dated Aug. 27, 2020", 29 pgs.
"Chinese Application Serial No. 201780028316.3, Office Action dated Jul. 14, 2020", w/ English translation, 16 pgs.
"Chinese Application Serial No. 201780029822.4, Response filed Jul. 6, 2020 to Office Action dated Feb. 14, 2020", w/ English claims, 11 pgs.
"Chinese Application Serial No. 201780029823.9, Office Action dated Jul. 9, 2020", w/ English Translation, 24 pgs.
"Chinese Application Serial No. 201780029824.3, Response filed Sep. 25, 2020 to Office Action dated May 12, 2020", w/ English claims, 61 pgs.
"Chinese Application Serial No. 201780029841.7, Office Action dated Jul. 17, 2020", w/ English translation, 24 pgs.
"European Application Serial No. 17767420.7, Response filed Sep. 22, 2020 to Extended European Search Report dated Mar. 11, 2020", 11 pgs.
"International Application Serial No. PCT/US2020/022653, International Search Report dated Jul. 16, 2020", 4 pgs.
"International Application Serial No. PCT/US2020/022653, Written Opinion dated Jul. 16, 2020", 8 pgs.
"Japanese Application Serial No. 2020-148942, Voluntary Amendment filed Oct. 1, 2020", w/ English claims, 14 pgs.
"Chinese Application Serial No. 201880031338.X, Office Action dated Feb. 23, 2021", w/ English Translation, 13 pgs.
"Japanese Application Serial No. 2018-548842, Notification of Reasons for Refusal dated Mar. 16, 2021", w/ English Translation, 8 pgs.

* cited by examiner

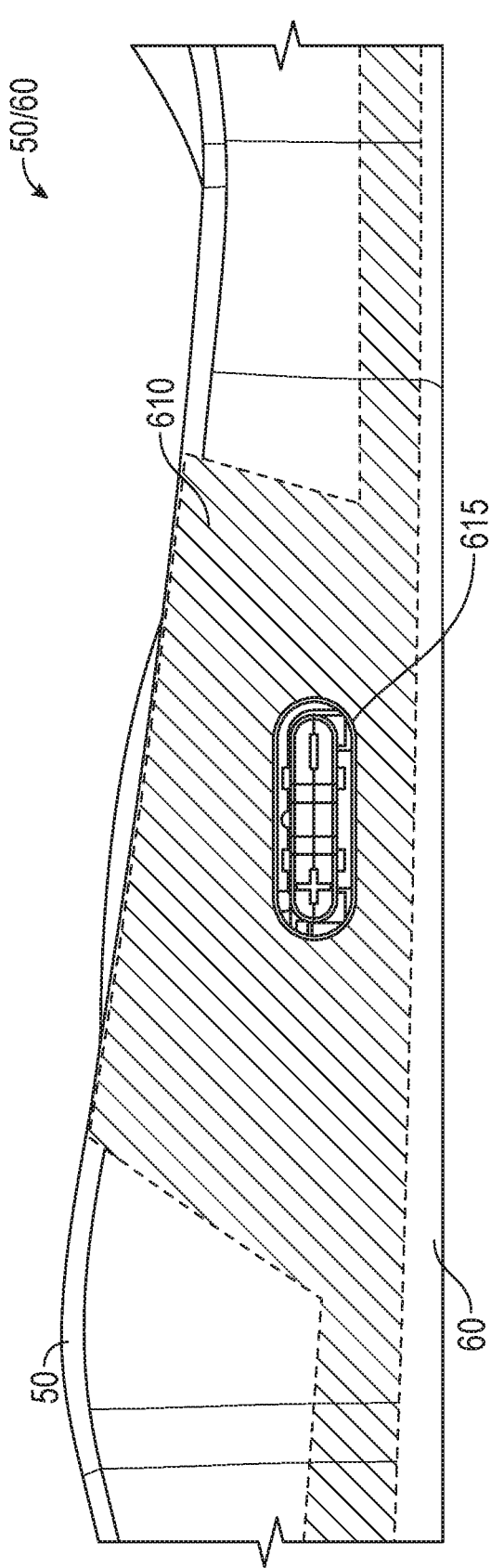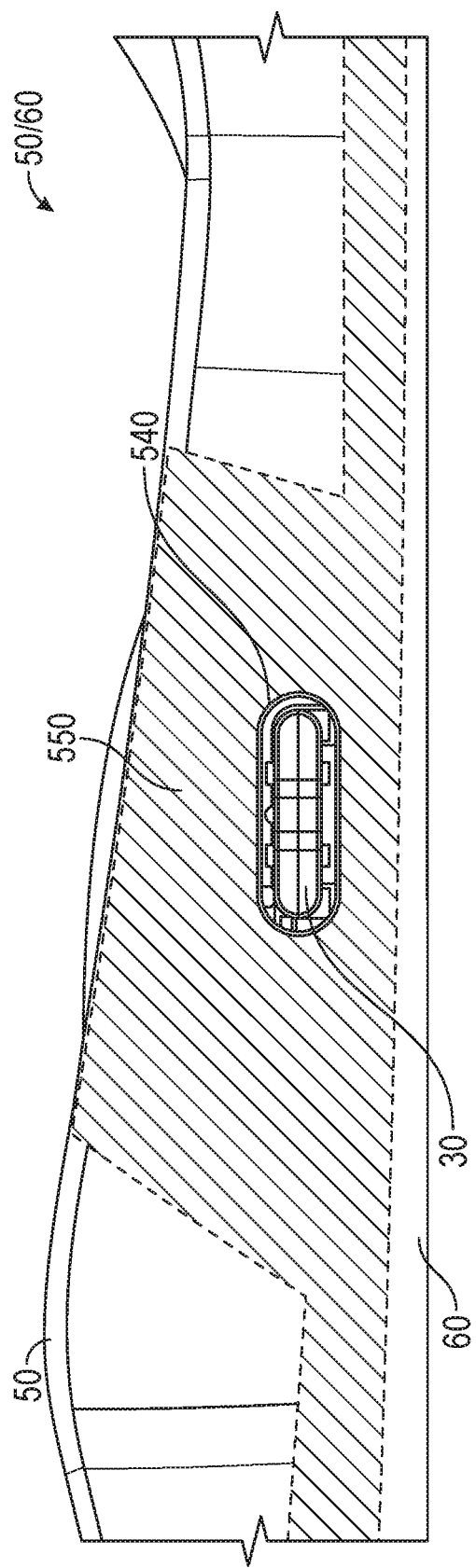

| MOVE (SPOOL) | ACCEL (DEG/S/S) | VEL (DEG/S) | DEC (DEG/S/S) | ANGLE (DEG) |
|---|---|---|---|---|
| HOME TO COMFORT | 100 | 400 | 200 | 550 |
| SEGMENT | 400 | 100 | 400 | 30 |
| COMFORT TO PERFORMANCE | 100 | 400 | 200 | 550 |
| RELAX | 50 | 5 | 50 | -5 |
| RETURN TO HOME | 100 | 400 | 200 | 550 |
| FIND HOME | 100 | 10 | | |
| UNTANGLE 1 | | | | |

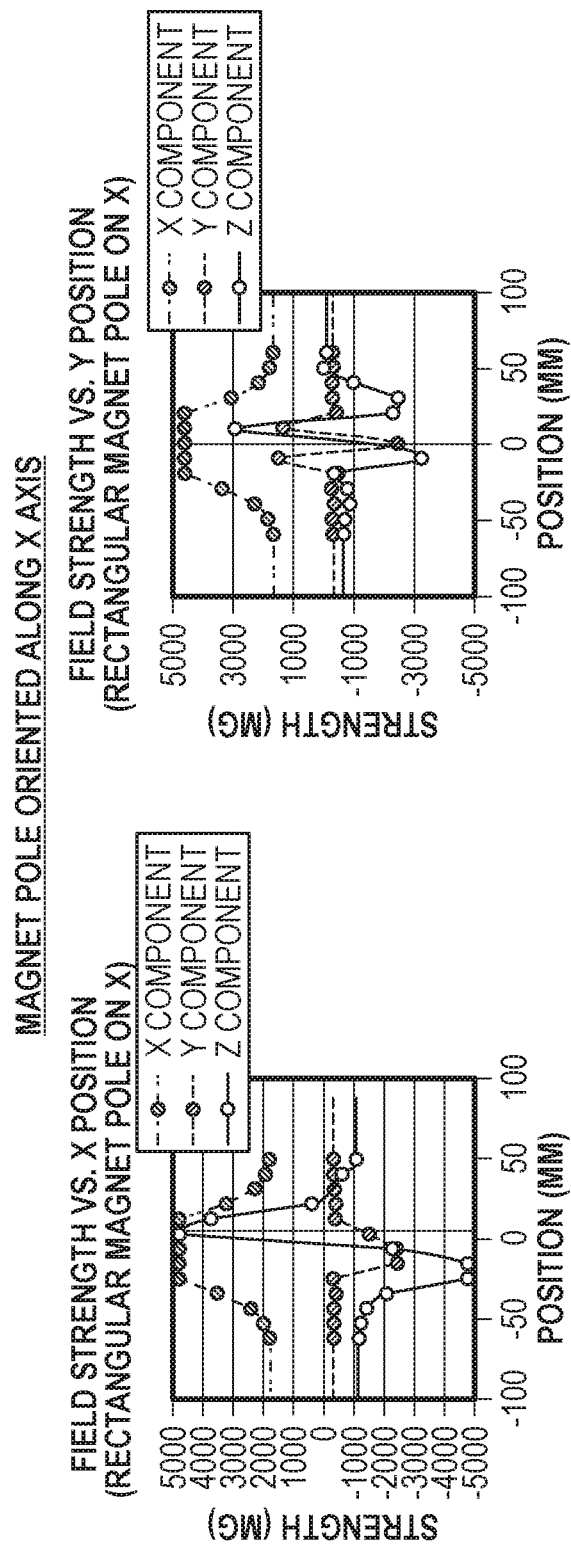
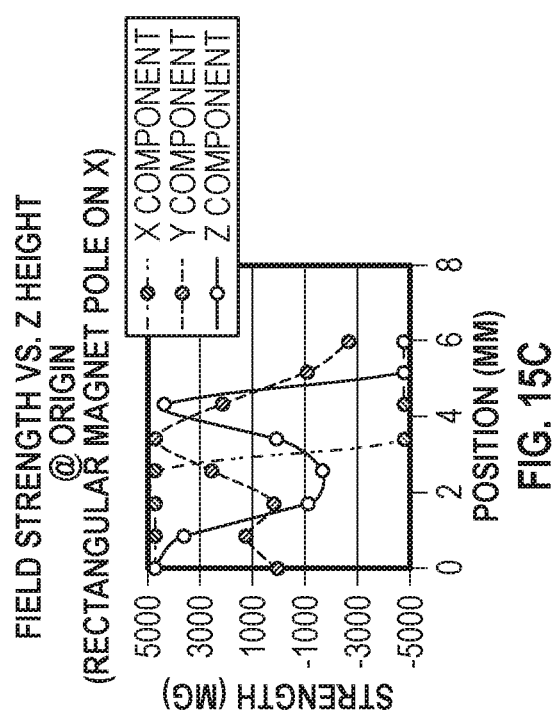

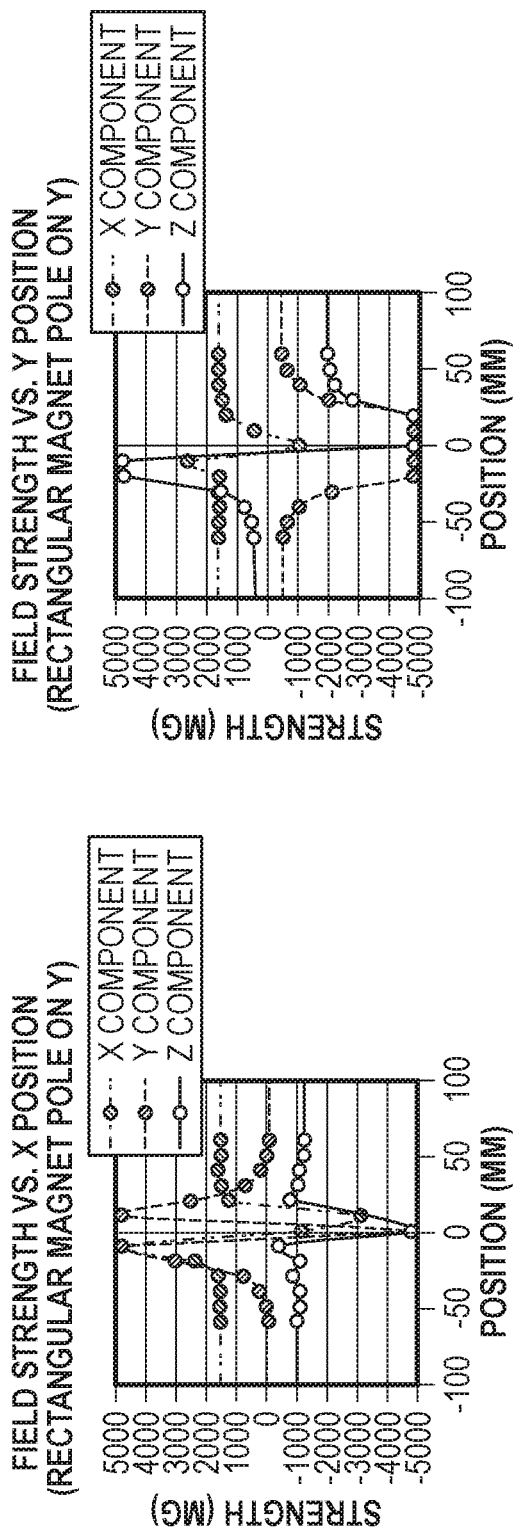
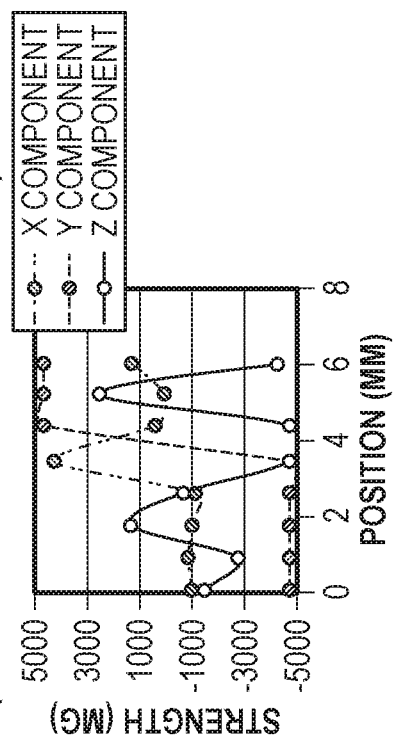

MAGNET POLE ORIENTED ALONG Z AXIS
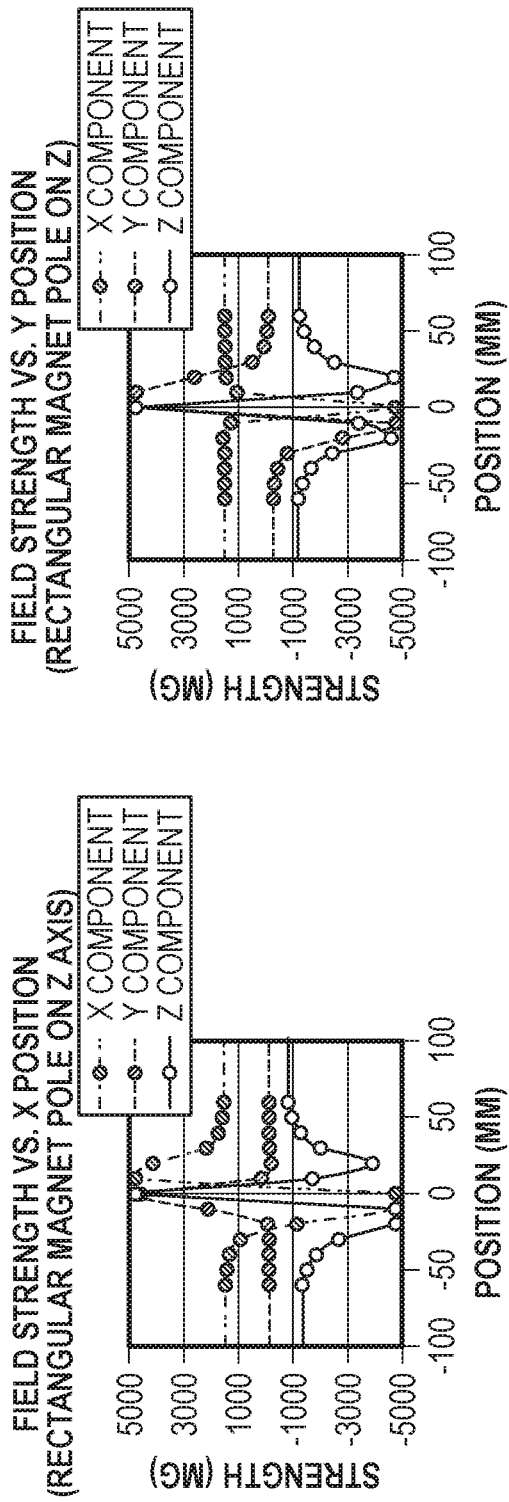
FIG. 15G
FIG. 15H
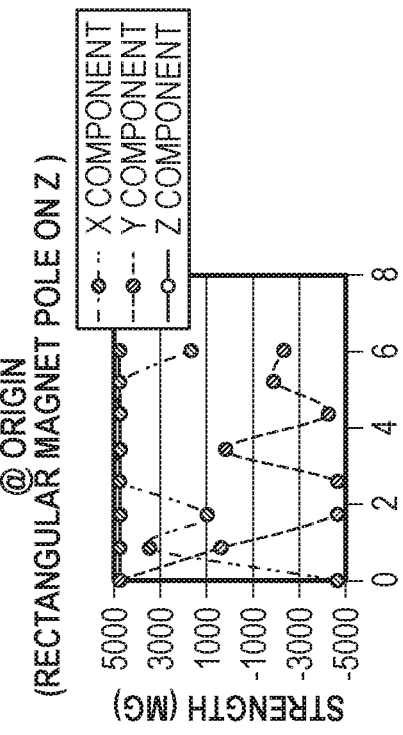
FIG. 15I

SMALL CIRCULAR MAGNET

FIELD STRENGTH VS. Z HEIGHT
@ X5MM Y5MM
(H1.1MM Ø2.5MM MAGNET POLE ON Z)

SNR VS. Z HEIGHT
@ X5MM Y5MM
(H1.1MM Ø2.5 MM MAGNET POLE ON Z)

LARGE CIRCULAR MAGNET

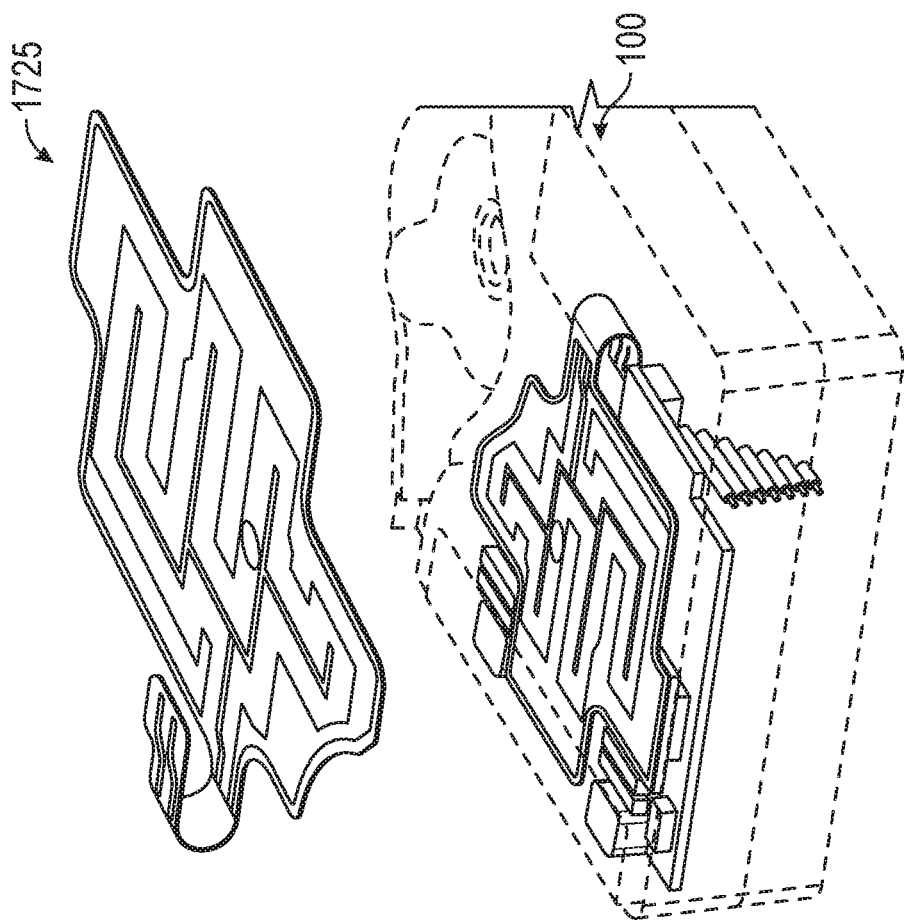
FIG. 20C
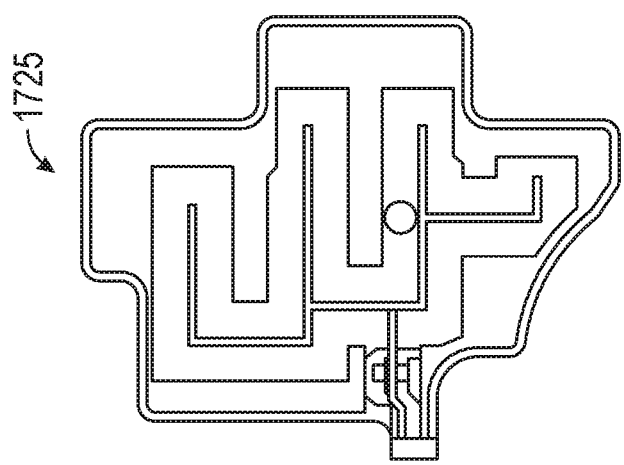

FOOT PRESENCE SENSING USING MAGNETS IN FOOTWEAR

CLAIM OF PRIORITY

This application claims the benefit of priority of Walker et al., U.S. Provisional Patent Application Ser. No. 62/308,657, entitled "MAGNETIC AND PRESSURE-BASED FOOT PRESENCE AND POSITION SENSING SYSTEMS AND METHODS FOR ACTIVE FOOTWEAR," filed on Mar. 15, 2016, and of Walker et al., U.S. Provisional Patent Application Ser. No. 62/308,667, entitled "CAPACITIVE FOOT PRESENCE AND POSITION SENSING SYSTEMS AND METHODS FOR ACTIVE FOOTWEAR," filed on Mar. 15, 2016, and of Walker, Steven H., U.S. Provisional Patent Application Ser. No. 62/424,939, entitled "CAPACITIVE FOOT PRESENCE SENSING FOR FOOTWEAR," filed on Nov. 21, 2016, and of Walker, Steven H., U.S. Provisional Patent Application Ser. No. 62/424,959, entitled "FOOT PRESENCE AND IMPACT RATE OF CHANGE FOR ACTIVE FOOTWEAR," filed on Nov. 21, 2016, each of which is herein incorporated by reference.

BACKGROUND

Various shoe-based sensors have been proposed to monitor various conditions. For example, Brown, in U.S. Pat. No. 5,929,332, titled "Sensor shoe for monitoring the condition of a foot", provides several examples of shoe-based sensors. Brown mentions a foot force sensor can include an insole made of layers of relatively thin, planar, flexible, resilient, dielectric material. The foot force sensor can include electrically conductive interconnecting means that can have an electrical resistance that decreases as a compressive force applied to it increases.

Brown further discusses a shoe to be worn by diabetic persons, or persons afflicted with various types of foot maladies, where excess pressure exerted upon a portion of the foot tends to give rise to ulceration. The shoe body can include a force sensing resistor, and a switching circuit coupled to the resistor can activate an alarm unit to warn a wearer that a threshold pressure level is reached or exceeded.

Brown also mentions a sensor disposed in a contained liquid mass of a hydrocell carried in a shoe's inner sole, the sensor being one that detects both pressure and temperature values to which a patient's feet are exposed. The sensor can include a circuit comprised of four piezoresistors arranged in diagonally arrayed pairs, the resistance of one pair of resistors increasing and the resistance of the second pair decreasing in the presence of an increase in the pressure condition in the hydrocell, and the resistance of all the resistors increasing or decreasing responsive to respective increases and decreases of temperature in the hydrocell. Outputs from the circuit can indicate respective pressure and temperature value changes. Brown mentions that a grid array sensor can detect localized pressure changes on a foot bottom by reducing the resistance between conductors present at the location of the increases in pressure. The decreased resistance can cause an increase in current flow between the conductors that is detected by a processor, and the processor in turn can provide an indication of an increased pressure condition.

Devices for automatically tightening an article of footwear have been previously proposed. Liu, in U.S. Pat. No. 6,691,433, titled "Automatic tightening shoe", provides a first fastener mounted on a shoe's upper portion, and a second fastener connected to a closure member and capable of removable engagement with the first fastener to retain the closure member at a tightened state. Liu teaches a drive unit mounted in the heel portion of the sole. The drive unit includes a housing, a spool rotatably mounted in the housing, a pair of pull strings and a motor unit. Each string has a first end connected to the spool and a second end corresponding to a string hole in the second fastener. The motor unit is coupled to the spool. Liu teaches that the motor unit is operable to drive rotation of the spool in the housing to wind the pull strings on the spool for pulling the second fastener towards the first fastener. Liu also teaches a guide tube unit that the pull strings can extend through.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 5A-5D are diagrams and drawings illustrating a mid-sole and out-sole to accommodate a lacing engine and related components, according to some example embodiments.

FIGS. 15A-15C illustrate test data associated with magnet-based foot presence sensor configurations with a magnet pole oriented along an x-axis.

FIGS. 15D-15F illustrate test data associated with magnet-based foot presence sensor configurations with a magnet pole oriented along a y-axis.

FIGS. 15G-15I illustrate test data associated with magnet-based foot presence sensor configurations with a magnet pole oriented along a z-axis.

FIGS. 20A-20C illustrate generally examples of capacitor-based foot presence sensors.

Figure 1:
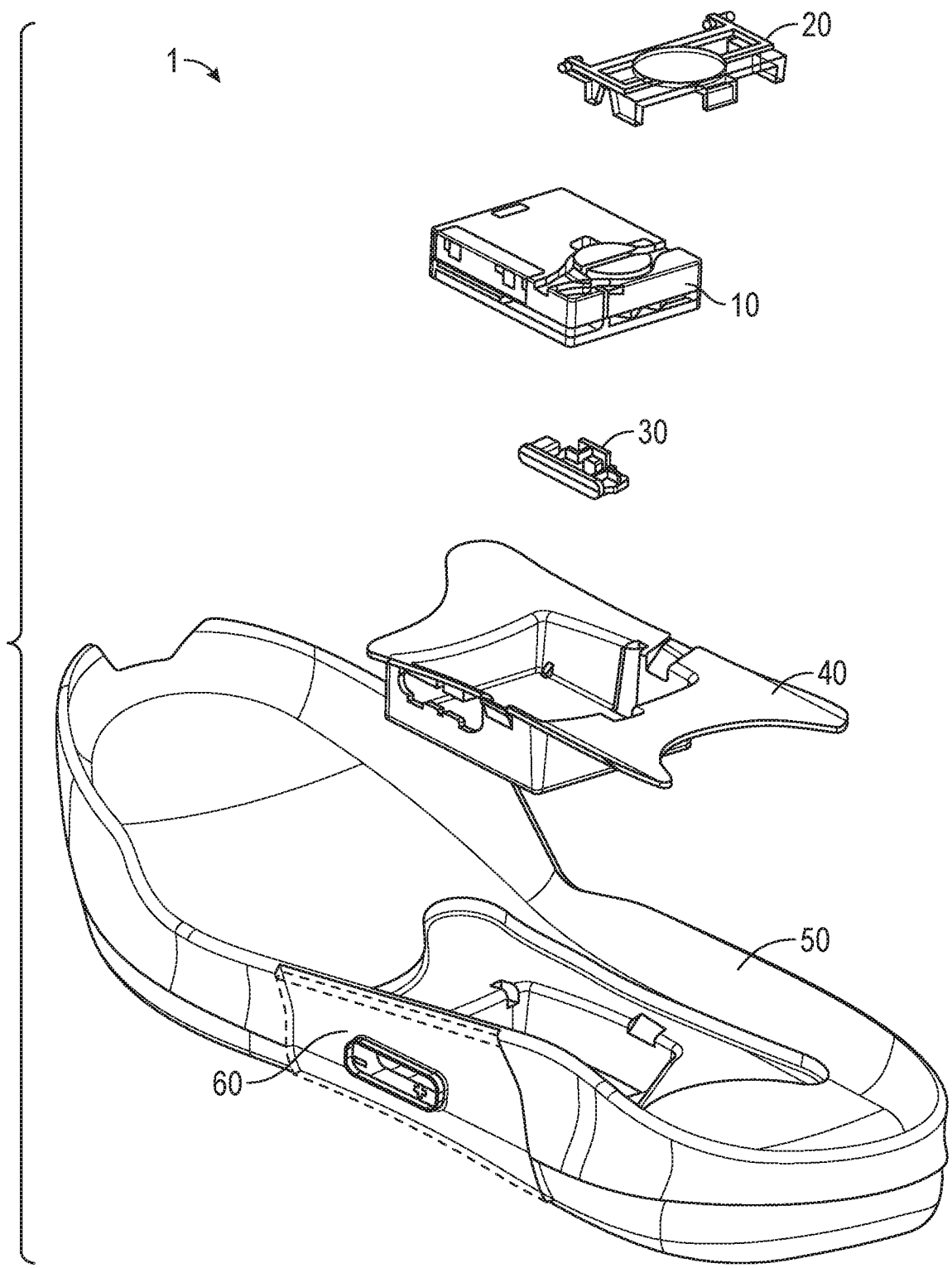
FIG. 1 is an exploded view illustration of components of a motorized lacing system, according to some example embodiments.

The headings provided herein are merely for convenience and do not necessarily affect the scope or meaning of the terms used.

DETAILED DESCRIPTION

The concept of self-tightening shoe laces was first widely popularized by the fictitious power-laced Nike® sneakers worn by Marty McFly in the movie Back to the Future II, which was released back in 1989. While Nike® has since released at least one version of power-laced sneakers similar in appearance to the movie prop version from Back to the Future II, the internal mechanical systems and surrounding footwear platform employed do not necessarily lend themselves to mass production or daily use. Additionally, previous designs for motorized lacing systems comparatively suffered from problems such as high cost of manufacture, complexity, assembly challenges, lack of serviceability, and weak or fragile mechanical mechanisms, to highlight just a few of the many issues. The present inventors have developed a modular footwear platform to accommodate motorized and non-motorized lacing engines that solves some or all of the problems discussed above, among others. The components discussed below provide various benefits including, but not limited to: serviceable components, interchangeable automated lacing engines, robust mechanical design, reliable operation, streamlined assembly processes, and retail-level customization. Various other benefits of the components described below will be evident to persons of skill in the relevant arts.

The motorized lacing engine discussed below was developed from the ground up to provide a robust, serviceable, and inter-changeable component of an automated lacing footwear platform. The lacing engine includes unique design elements that enable retail-level final assembly into a modular footwear platform. The lacing engine design allows for the majority of the footwear assembly process to leverage known assembly technologies, with unique adaptions to standard assembly processes still being able to leverage current assembly resources.

In an example, the modular automated lacing footwear platform includes a mid-sole plate secured to the mid-sole for receiving a lacing engine. The design of the mid-sole plate allows a lacing engine to be dropped into the footwear platform as late as at a point of purchase. The mid-sole plate, and other aspects of the modular automated footwear platform, allow for different types of lacing engines to be used interchangeably. For example, the motorized lacing engine discussed below could be changed out for a human-powered lacing engine. Alternatively, a fully-automatic motorized lacing engine with foot presence sensing or other optional features could be accommodated within the standard mid-sole plate.

The automated footwear platform discussed herein can include an outsole actuator interface to provide tightening control to the end user as well as visual feedback through LED lighting projected through translucent protective outsole materials. The actuator can provide tactile and visual feedback to the user to indicate status of the lacing engine or other automated footwear platform components.

This initial overview is intended to introduce the subject matter of the present patent application. It is not intended to provide an exclusive or exhaustive explanation of the various inventions disclosed in the following more detailed description.

The following discusses various components of the automated footwear platform including a motorized lacing engine, a mid-sole plate, and various other components of the platform. While much of this disclosure focuses on a motorized lacing engine, many of the mechanical aspects of the discussed designs are applicable to a human-powered lacing engine or other motorized lacing engines with additional or fewer capabilities. Accordingly, the term "automated" as used in "automated footwear platform" is not intended to only cover a system that operates without user input. Rather, the term "automated footwear platform" includes various electrically powered and human-power, automatically activated and human activated mechanisms for tightening a lacing or retention system of the footwear.

FIG. 1 is an exploded view illustration of components of a motorized lacing system for footwear, according to some example embodiments. The motorized lacing system 1 illustrated in FIG. 1 includes a lacing engine 10, a lid 20, an actuator 30, a mid-sole plate 40, a mid-sole 50, and an outsole 60. FIG. 1 illustrates the basic assembly sequence of components of an automated lacing footwear platform. The motorized lacing system 1 starts with the mid-sole plate 40 being secured within the mid-sole. Next, the actuator 30 is inserted into an opening in the lateral side of the mid-sole plate opposite to interface buttons that can be embedded in the outsole 60. Next, the lacing engine 10 is dropped into the mid-sole plate 40. In an example, the lacing system 1 is inserted under a continuous loop of lacing cable and the lacing cable is aligned with a spool in the lacing engine 10 (discussed below). Finally, the lid 20 is inserted into grooves in the mid-sole plate 40, secured into a closed position, and latched into a recess in the mid-sole plate 40. The lid 20 can capture the lacing engine 10 and can assist in maintaining alignment of a lacing cable during operation.

In an example, the footwear article or the motorized lacing system 1 includes or is configured to interface with one or more sensors that can monitor or determine a foot presence characteristic. Based on information from one or more foot presence sensors, the footwear including the motorized lacing system 1 can be configured to perform various functions. For example, a foot presence sensor can be configured to provide binary information about whether a foot is present or not present in the footwear. If a binary signal from the foot presence sensor indicates that a foot is present, then the motorized lacing system 1 can be activated, such as to automatically tighten or relax (i.e., loosen) a footwear lacing cable. In an example, the footwear article includes a processor circuit that can receive or interpret signals from a foot presence sensor. The processor circuit can optionally be embedded in or with the lacing engine 10, such as in a sole of the footwear article.

In an example, a foot presence sensor can be configured to provide information about a location of a foot as it enters footwear. The motorized lacing system 1 can generally be activated, such as to tighten a lacing cable, only when a foot is appropriately positioned or seated in the footwear, such as against all or a portion of the footwear article's sole. A foot presence sensor that senses information about a foot travel or location can provide information about whether a foot is fully or partially seated, such as relative to a sole or relative to some other feature of the footwear article. Automated lacing procedures can be interrupted or delayed until information from the sensor indicates that a foot is in a proper position.

In an example, a foot presence sensor can be configured to provide information about a relative location of a foot inside of footwear. For example, the foot presence sensor can be configured to sense whether the footwear is a good "fit" for a given foot, such as by determining a relative position of one or more of a foot's arch, heel, toe, or other component, such as relative to the corresponding portions of the footwear that are configured to receive such foot components. In an example, the foot presence sensor can be configured to sense whether a position of a foot or a foot component has changed relative to some reference, such as due to loosening of a lacing cable over time, or due to natural expansion and contraction of a foot itself.

In an example, a foot presence sensor can include an electrical, magnetic, thermal, capacitive, pressure, optical, or other sensor device that can be configured to sense or receive information about a presence of a body. For example, an electrical sensor can include an impedance sensor that is configured to measure an impedance characteristic between at least two electrodes. When a body such as a foot is located proximal or adjacent to the electrodes, the electrical sensor can provide a sensor signal having a first value, and when a body is located remotely from the electrodes, the electrical sensor can provide a sensor signal having a different second value. For example, a first impedance value can be associated with an empty footwear condition, and a lesser second impedance value can be associated with an occupied footwear condition. In an example, the electrical sensor can be configured to provide a binary signal or interrupt signal when a foot is determined to be, or determined to be likely to be, present within the footwear. For example, when a measured electrical characteristic (e.g., capacitance, resistance, impedance, etc.) exceeds a specified threshold or reference value, the binary signal or interrupt signal can be asserted.

An electrical sensor can include an AC signal generator circuit and an antenna that is configured to emit or receive radio frequency information. Based on proximity of a body relative to the antenna, one or more electrical signal characteristics, such as impedance, frequency, or signal amplitude, can be received and analyzed to determine whether a body is present. In an example, a received signal strength indicator (RSSI) provides information about a power level in a received radio signal. Changes in the RSSI, such as relative to some baseline or reference value, can be used to identify a presence or absence of a body. In an example, WiFi frequencies can be used, for example in one or more of 2.4 GHz, 3.6 GHz, 4.9 GHz, 5 GHz, and 5.9 GHz bands. In an example, frequencies in the kilohertz range can be used, for example, around 400 kHz. In an example, power signal changes can be detected in milliwatt or microwatt ranges.

A foot presence sensor can include a magnetic sensor. A first agnetic sensor can include a magnet and a magnetometer, or a magnetometer and a material that can be sensed by the magnetometer. In an example, a magnetometer can be positioned in or near the lacing engine 10. A magnet, or other material that evokes a response by the magnetometer, can be located remotely from the lacing engine 10, such as in a secondary sole, or insole, that is configured to be worn above the outsole 60. In an example, the magnet is embedded in a foam or other compressible material of the secondary sole. As a user depresses the secondary sole such as when standing or walking, corresponding changes in the location of the magnet relative to the magnetometer can be sensed and reported via a sensor signal.

A second magnetic sensor can include a magnetic field sensor that is configured to sense changes or interruptions (e.g., via the Hall effect) in a magnetic field. When a body is proximal to the second magnetic sensor, the sensor can generate a signal that indicates a change to an ambient magnetic field. For example, the second magnetic sensor can include a Hall effect sensor that varies a voltage output signal in response to variations in a detected magnetic field. Voltage changes at the output signal can be due to production of a voltage difference across an electric signal conductor, such as transverse to an electric current in the conductor and a magnetic field perpendicular to the current.

In an example, the second magnetic sensor is configured to receive an electromagnetic field signal from a body. For example, Varshaysky et al., in U.S. Pat. No. 8,752,200, titled "Devices, systems and methods for security using magnetic field based identification", teaches using a body's unique electromagnetic signature for authentication. In an example, a magnetic sensor in a footwear article can be used to authenticate or verify that a present user is a shoe's owner via a detected electromagnetic signature, and that the article should lace automatically, such as according to one or more specified lacing preferences (e.g., tightness profile) of the owner.

In an example, a foot presence sensor includes a thermal sensor that is configured to sense a change in temperature in or near a portion of the footwear. When a wearer's foot enters a footwear article, the article's internal temperature changes when the wearer's own body temperature differs from an ambient temperature of the footwear article. Thus the thermal sensor can provide an indication that a foot is likely to present or not based on a temperature change.

In an example, a foot presence sensor includes a capacitive sensor that is configured to sense a change in capacitance. The capacitive sensor can include a single plate or electrode, or the capacitive sensor can include a multiple-plate or multiple-electrode configuration. Capacitive-type foot presence sensors are described at length below.

In an example, a foot presence sensor includes an optical sensor. The optical sensor can be configured to determine whether a line-of-sight is interrupted, such as between opposite sides of a footwear cavity. In an example, the optical sensor includes a light sensor that can be covered by a foot when the foot is inserted into the footwear. When the sensor indicates a change in a sensed lightness condition, an indication of a foot presence or position can be provided.

In an example, the motorized lacing system 1 of FIG. 1 includes the mid-sole 50, and the lacing engine 10. The system 1 can include an insole over the mid-sole and/or the lacing engine 10, such as to improve comfort or fit for a wearer of the footwear. A plurality of straps or laces can be adjusted by the lacing engine 10, such as to adjust a tightness or looseness characteristic of the article about a foot when the article is worn. That is, the plurality of straps or laces can be configured to move between tightened and loosened positions in response to activity of a motor in the lacing engine 10. In an example, the system 1 includes a ferromagnetic body disposed in the article, and at least one sensor configured to sense a location change of the ferromagnetic body in response to compression of the insole by a foot when the article is worn. The ferromagnetic body can be disposed, for example, in or on the insole such that when a wearer takes a step or stands, a compressive force of the wearer's foot on the insole moves the ferromagnetic body. Although referred to herein as a ferromagnetic body, the body can be any material that is detectable by, or whose movement is detectable by, the sensor. In an example, the lacing engine 10 can be coupled to the sensor and the lacing engine 10 can be configured to respond to a sensed change in the location of the ferromagnetic body by adjusting a tension of the straps or laces.

The sensor can include a magnetometer that is configured to sense a change in a magnetic field. The magnetic field change can be due at least in part to a location change of the ferromagnetic body, such as in response to movement of the footwear or of a foot within the footwear. In an example, one of the ferromagnetic body and the magnetometer is substantially fixed relative to a housing or wall of the article, and the other one of the ferromagnetic body and the magnetometer is movable with respect to the housing or wall of the article. For example, the ferromagnetic body can be disposed in the insole and movable in response to compressive foot forces, and a position of the magnetometer can be substantially fixed in the mid-sole or in the lacing engine 10.

In an example, information about the change in the location of the ferromagnetic body can be sensed and used to determine various characteristics of circumstances of the article's use. For example, information about a changing magnetic field can be sensed by the magnetometer in response to movement of the ferromagnetic body. Large or rapid changes in the magnetic field can indicate the ferromagnetic body is moving quickly or by a great distance, thus indicating that a wearer is exerting a substantial force on the footwear such as due to a running or jumping activity. Timing information about the sensed magnetic field or location changes of the ferromagnetic body can be used to determine a foot strike timing, such as to count steps or to determine how quickly the wearer is moving (e.g., when stride information is known or discernable).

Figure 2A:
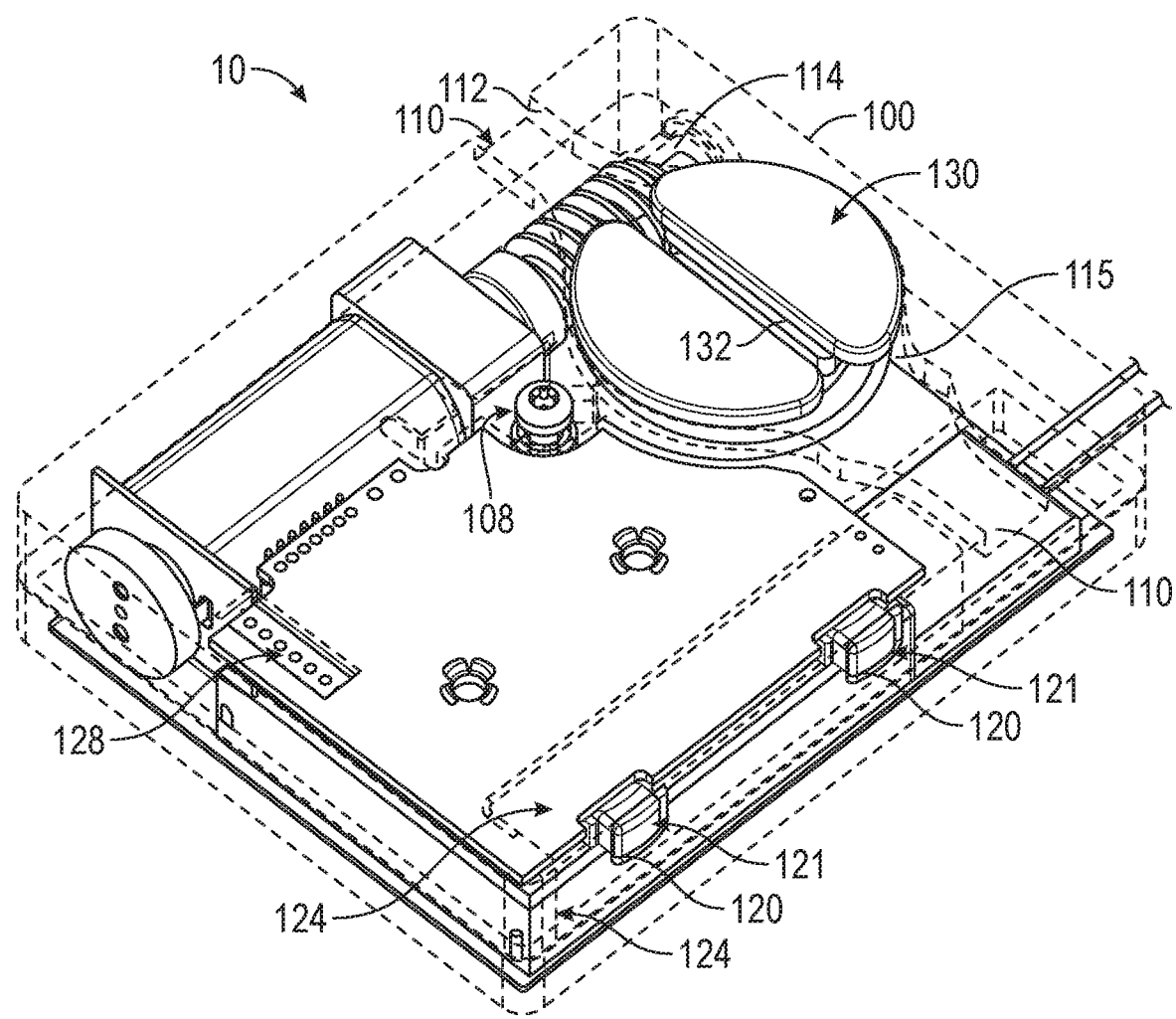
FIGS. 2A-2N are diagrams and drawings illustrating a motorized lacing engine, according to some example embodiments.
Figure 2B:
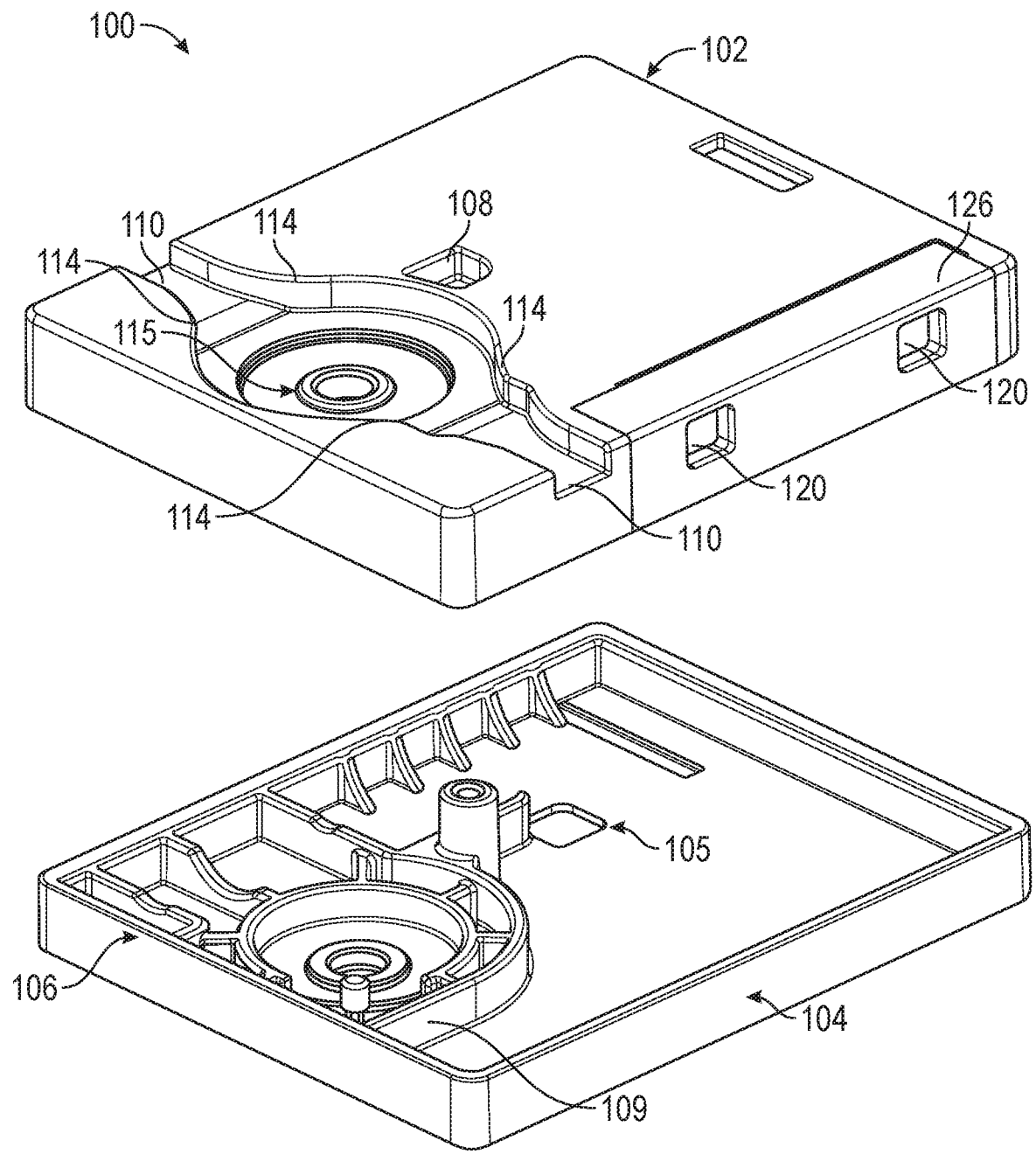
Figure 2C:
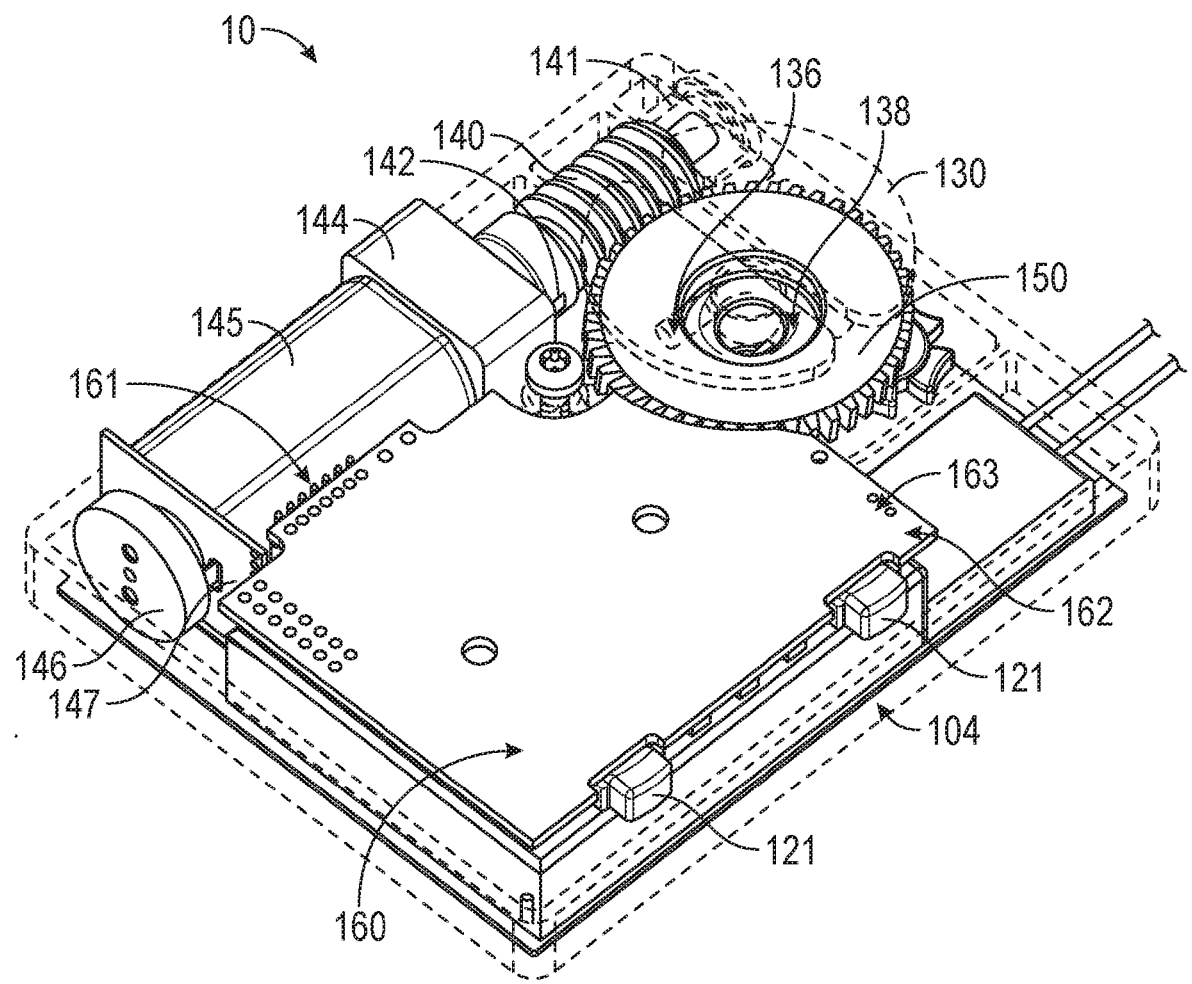
Figure 2D:
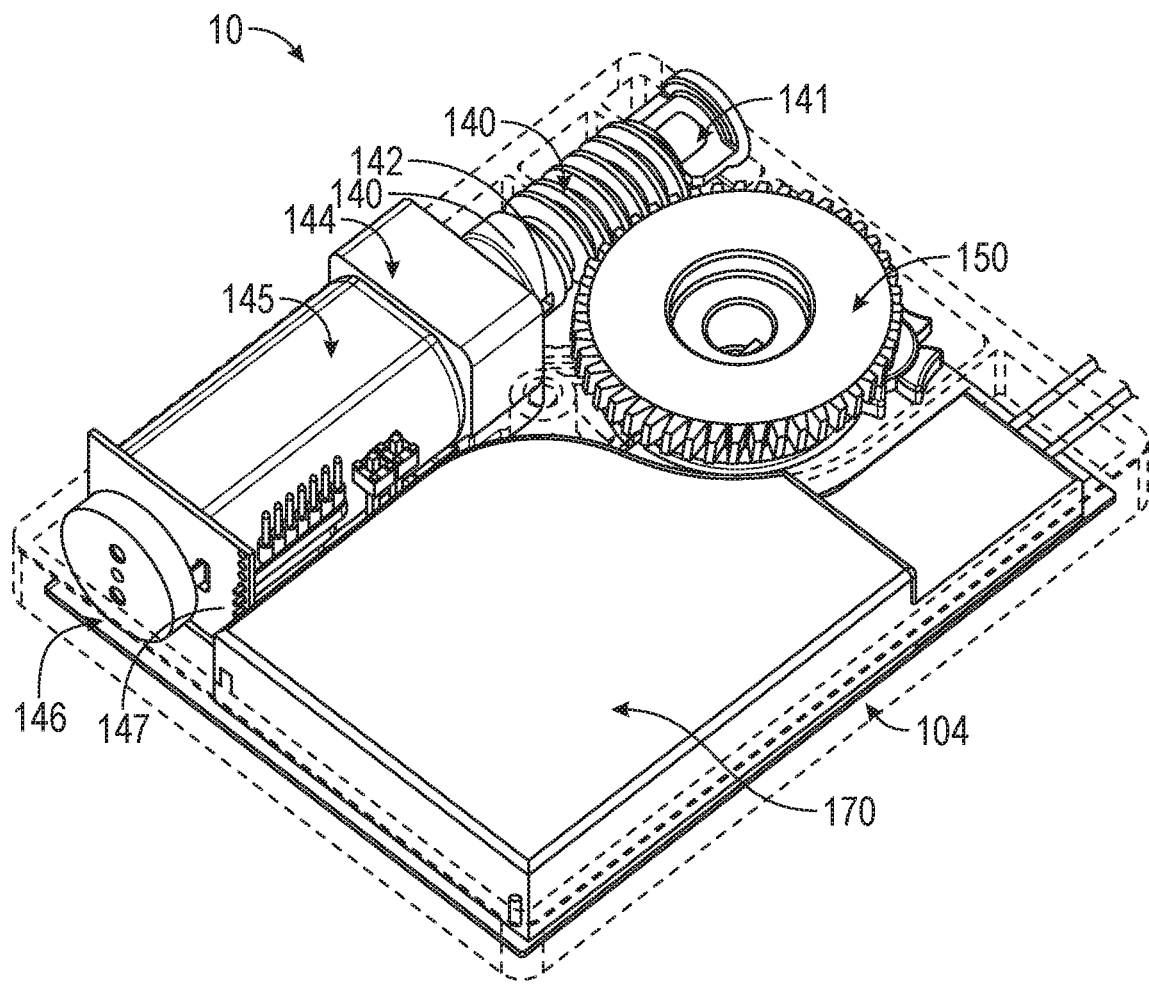
Figure 2E:
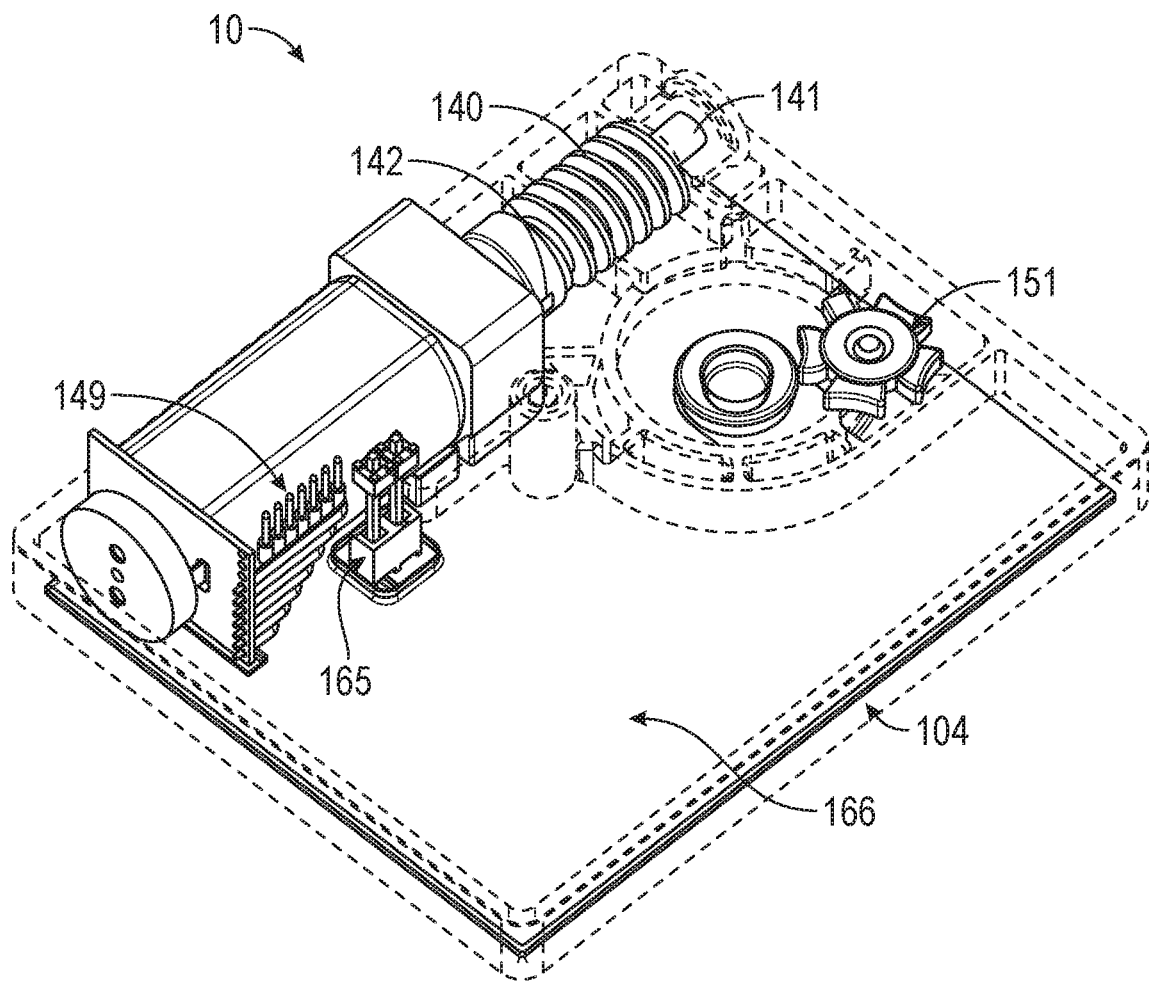
Figure 2F:
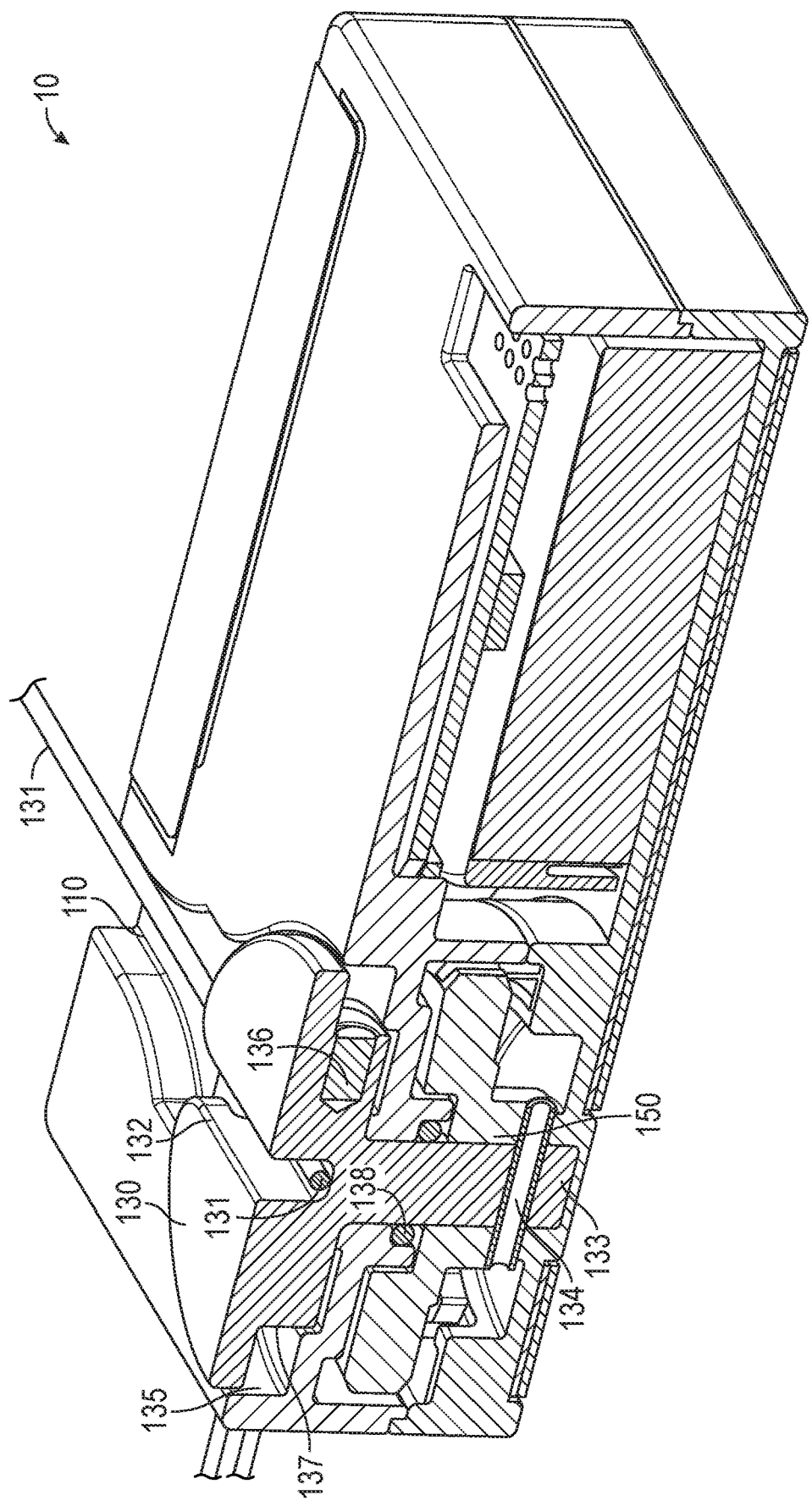
Figure 2G:
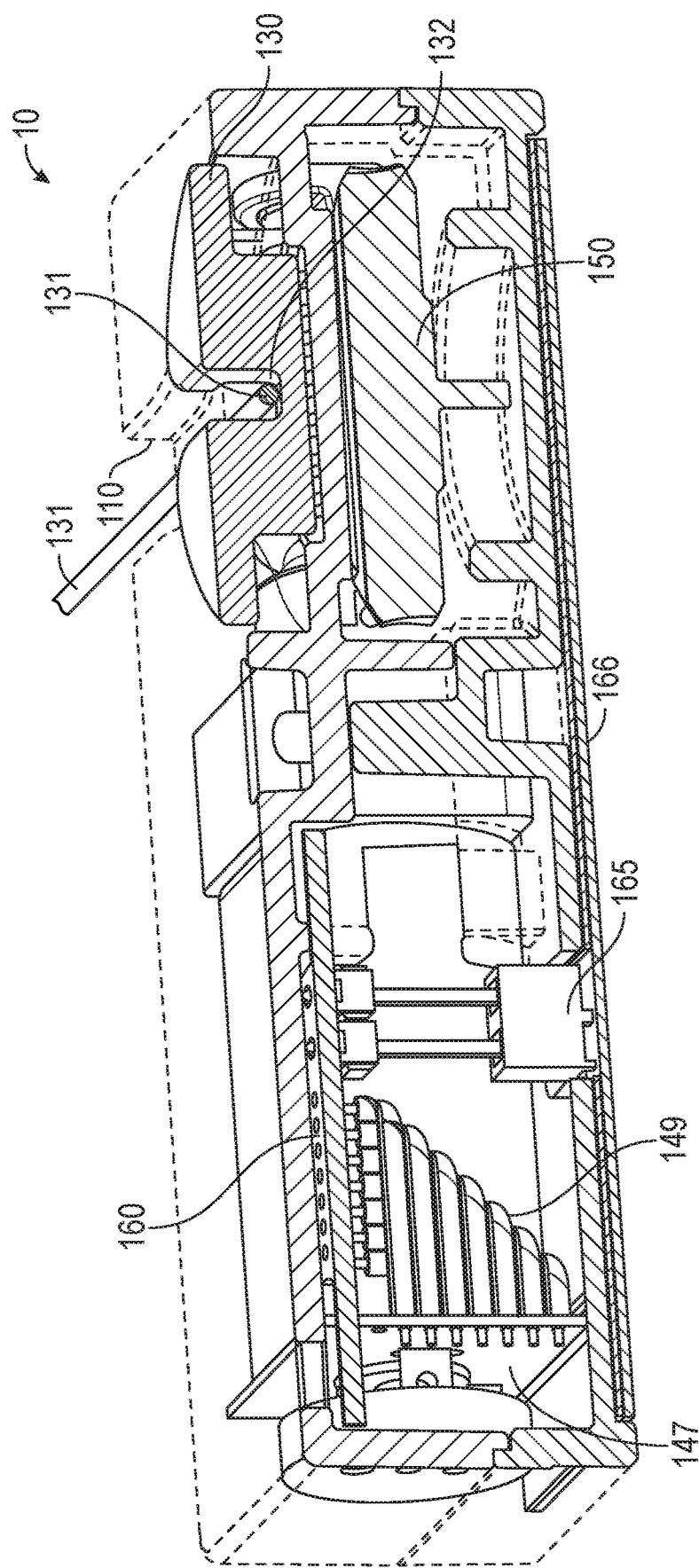
Figure 2H:
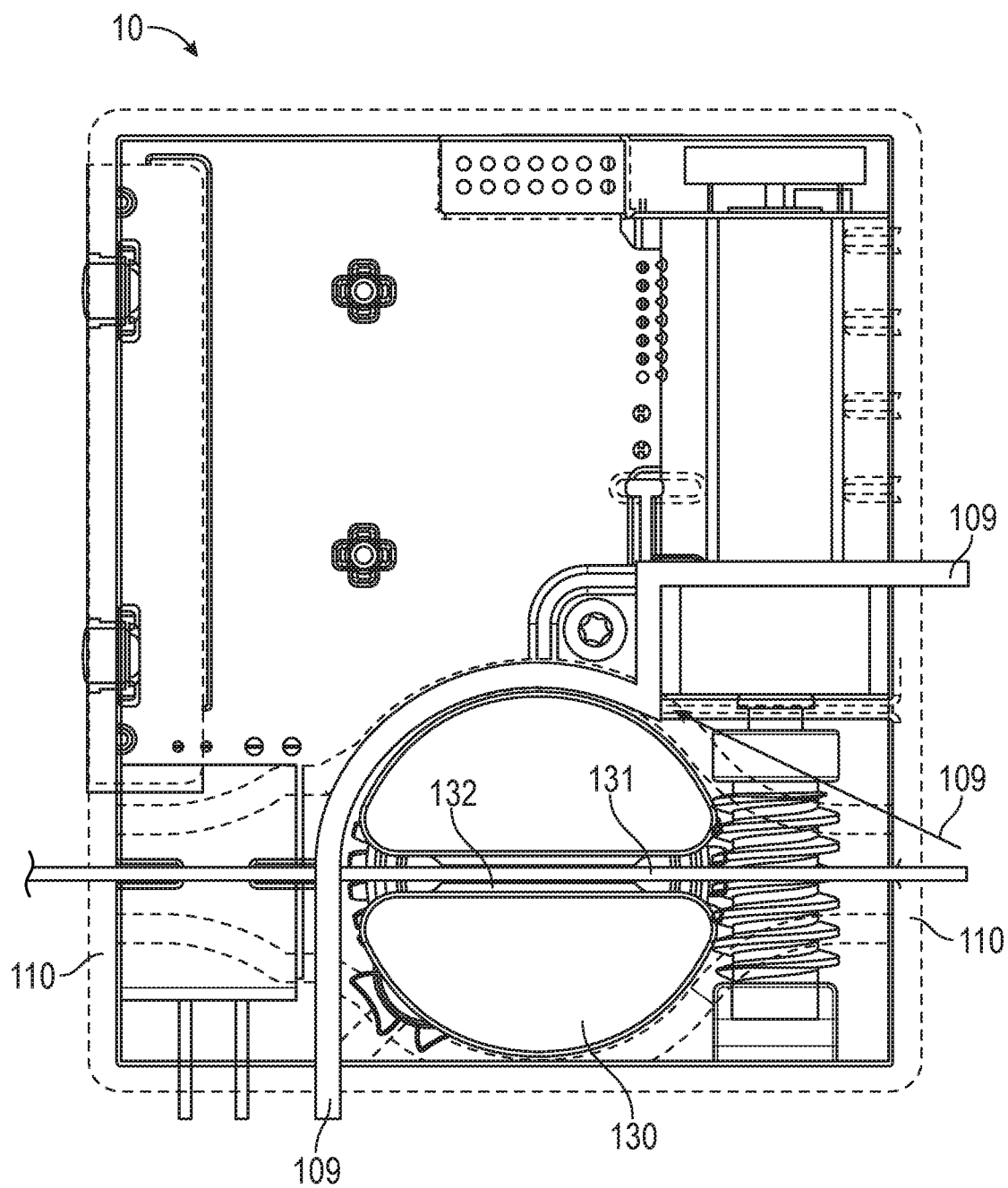
Figure 2I:
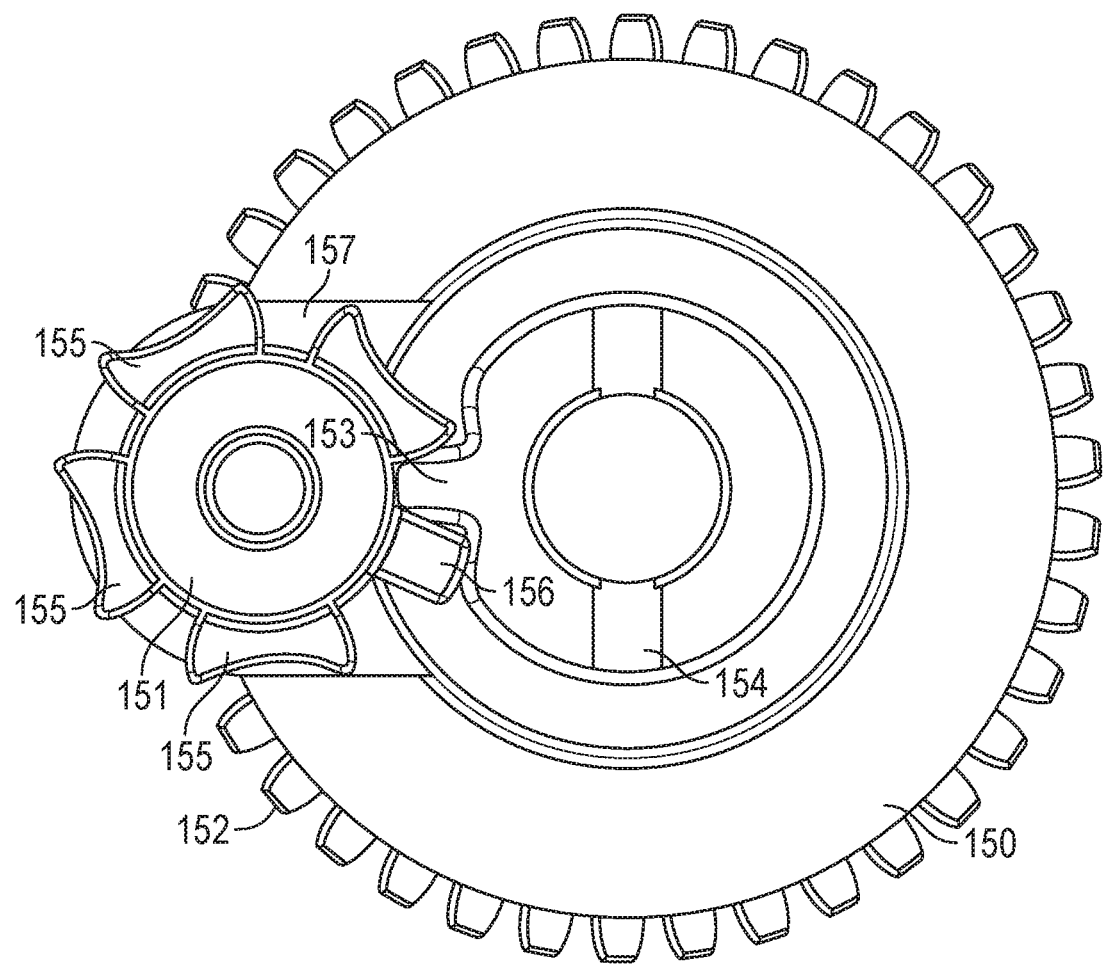
Figure 2J:
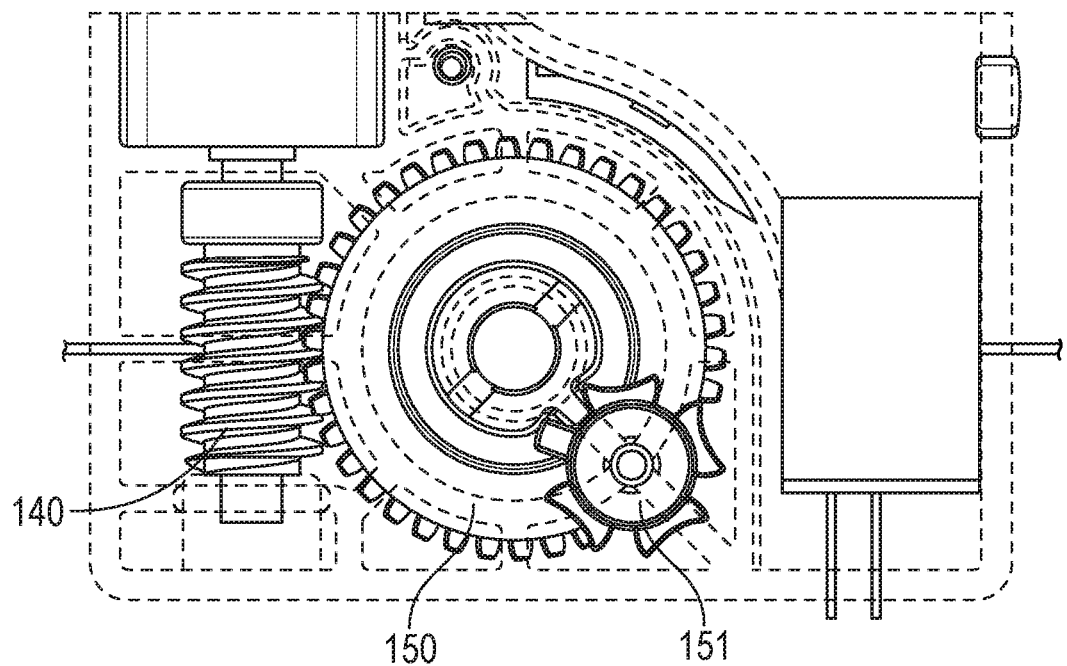
Figure 2K:
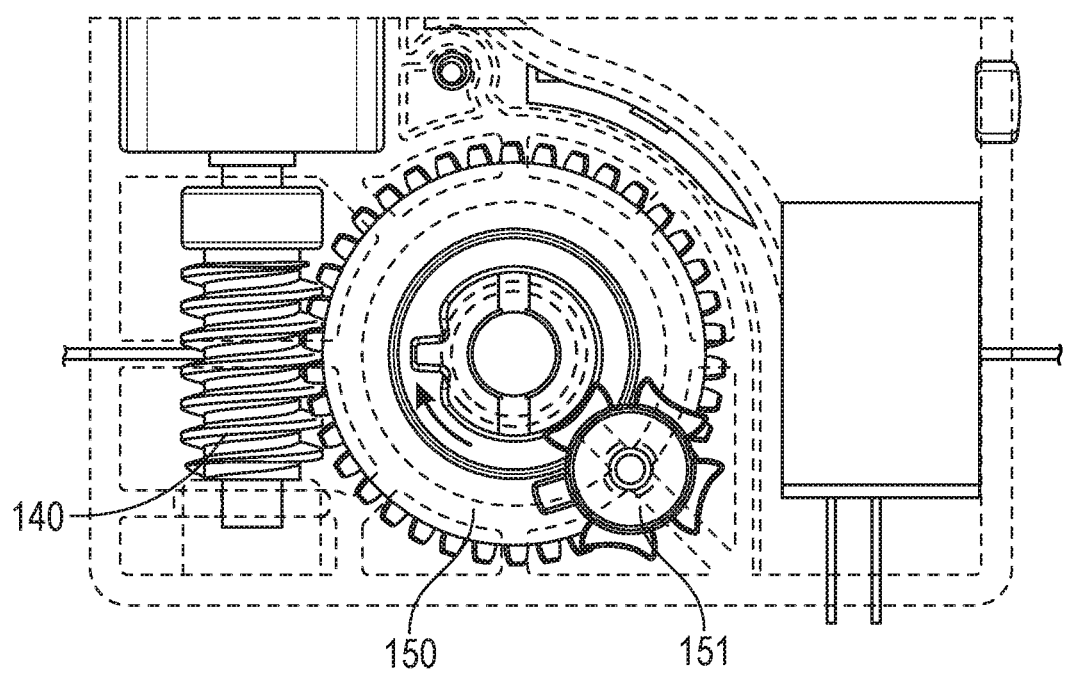
Figure 2L:
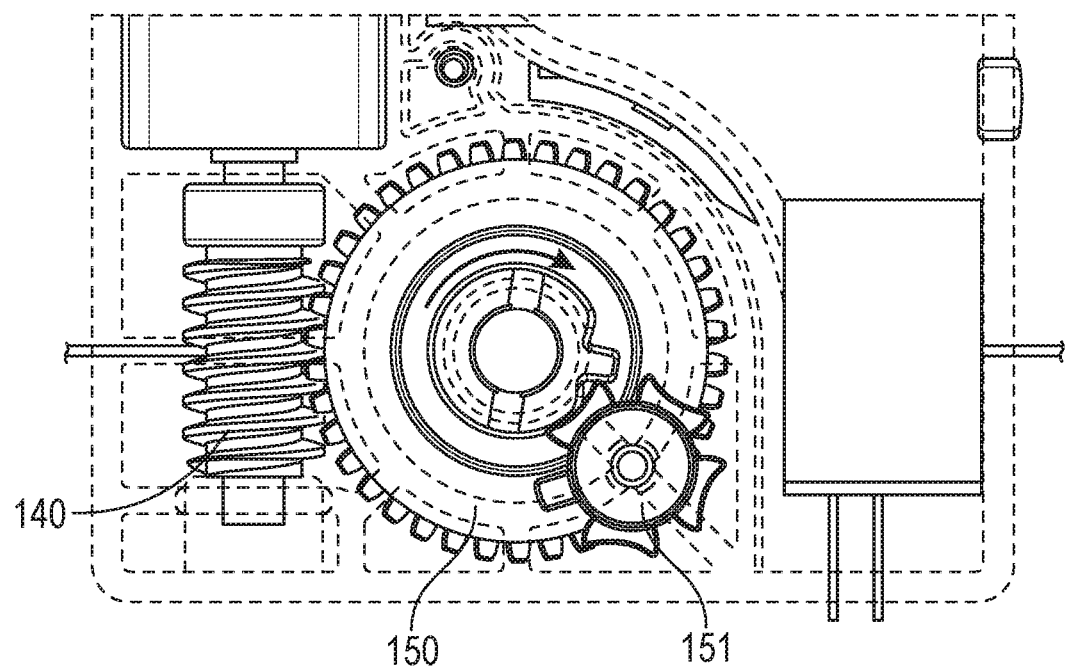
Figure 2M:
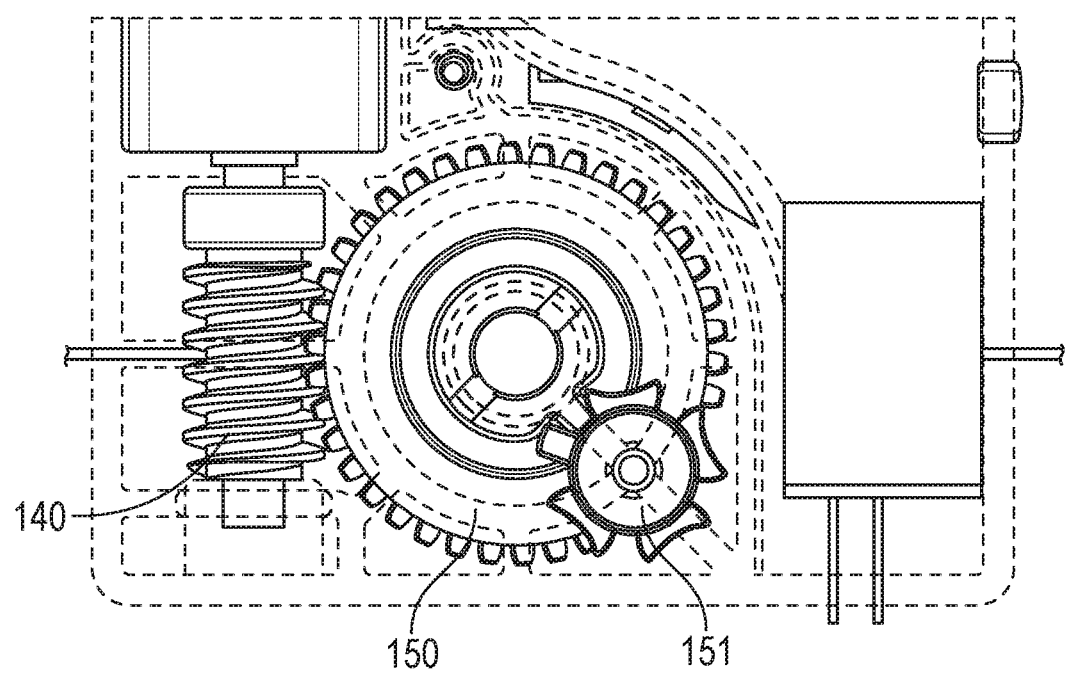
Figure 2N:
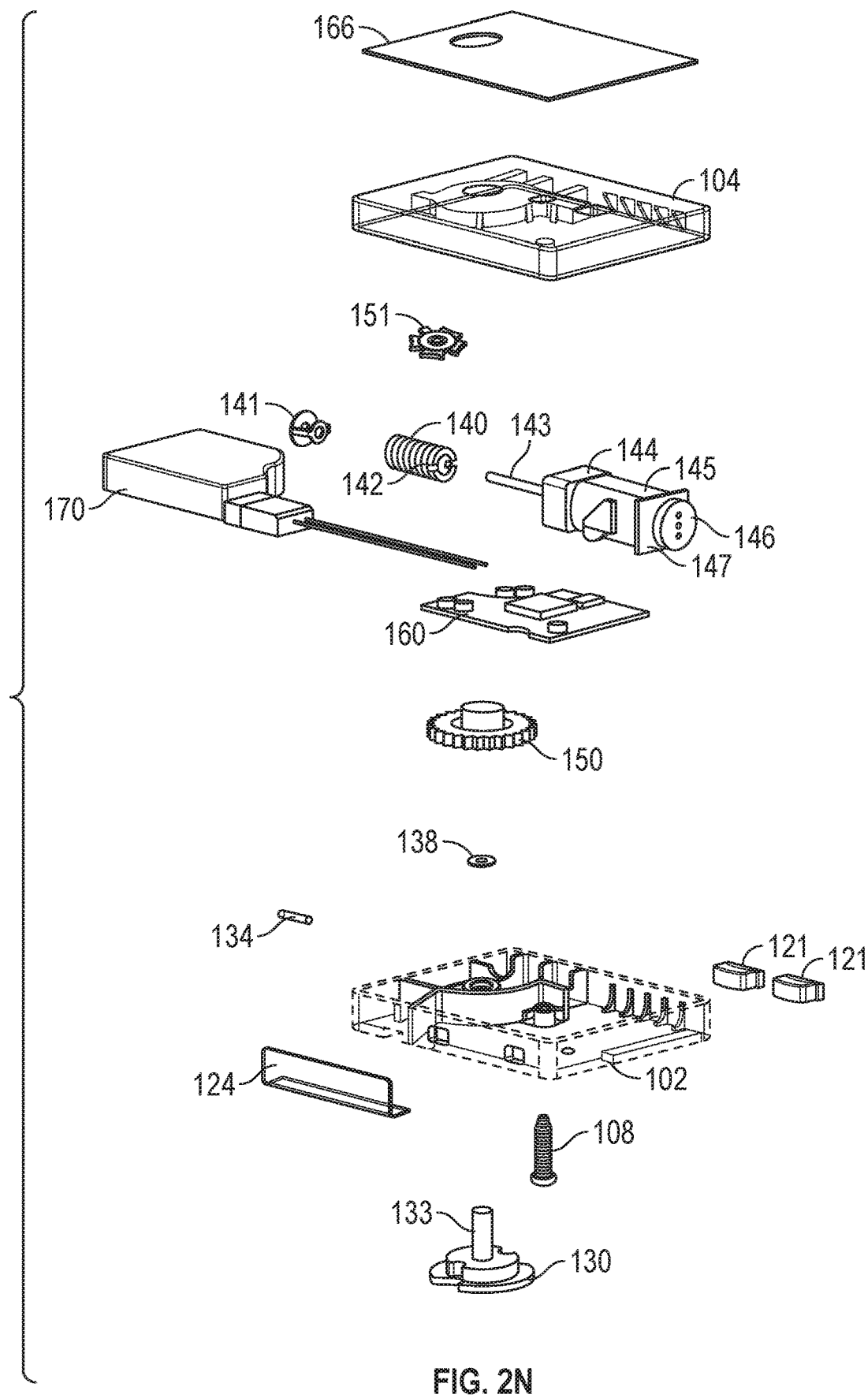

Examples of the lacing engine 10 are described in detail in reference to FIGS. 2A-2N. Examples of the actuator 30 are described in detail in reference to FIGS. 3A-3D, Examples of the mid-sole plate 40 are described in detail in reference to FIGS. 4A-4D. Various additional details of the motorized lacing system 1 are discussed throughout the remainder of the description.

FIGS. 2A-2N are diagrams and drawings illustrating a motorized lacing engine, according to some example embodiments. FIG. 2A introduces various external features of an example lacing engine 10, including a housing structure 100, case screw 108, lace channel 110 (also referred to as lace guide relief 110), lace channel wall 112, lace channel transition 114, spool recess 115, button openings 120, buttons 121, button membrane seal 124, programming header 128, spool 130, and lace grove 132. Additional details of the housing structure 100 are discussed below in reference to FIG. 2B.

In an example, the lacing engine 10 is held together by one or more screws, such as the case screw 108. The case screw 108 is positioned near the primary drive mechanisms to enhance structural integrity of the lacing engine 10. The case screw 108 also functions to assist the assembly process, such as holding the case together for ultra-sonic welding of exterior seams.

In this example, the lacing engine 10 includes a lace channel 110 to receive a lace or lace cable once assembled into the automated footwear platform. The lace channel 110 can include a lace channel wall 112. The lace channel wall 112 can include chamfered edges to provide a smooth guiding surface for a lace cable to run in during operation. Part of the smooth guiding surface of the lace channel 110 can include a channel transition 114, which is a widened portion of the lace channel 110 leading into the spool recess 115. The spool recess 115 transitions from the channel transition 114 into generally circular sections that conform closely to the profile of the spool 130. The spool recess 115 assists in retaining the spooled lace cable, as well as in retaining position of the spool 130. However, other aspects of the design provide primary retention of the spool 130. In this example, the spool 130 is shaped similarly to half of a yo-yo with a lace grove 132 running through a flat top surface and a spool shaft 133 (not shown in FIG. 2A) extending inferiorly from the opposite side. The spool 130 is described in further detail below in reference of additional figures.

The lateral side of the lacing engine 10 includes button openings 120 that enable buttons 121 for activation of the mechanism to extend through the housing structure 100. The buttons 121 provide an external interface for activation of switches 122, illustrated in additional figures discussed below. In some examples, the housing structure 100 includes button membrane seal 124 to provide protection from dirt and water. In this example, the button membrane seal 124 is up to a few mils (thousandth of an inch) thick clear plastic (or similar material) adhered from a superior surface of the housing structure 100 over a corner and down a lateral side. In another example, the button membrane seal 124 is a 2 mil thick vinyl adhesive backed membrane covering the buttons 121 and button openings 120.

FIG. 2B is an illustration of housing structure 100 including top section 102 and bottom section 104. In this example, the top section 102 includes features such as the case screw 108, lace channel 110, lace channel transition 114, spool recess 115, button openings 120, and button seal recess 126. The button seal recess 126 is a portion of the top section 102 relieved to provide an inset for the button membrane seal 124. In this example, the button seal recess 126 is a couple mil recessed portion on the lateral side of the superior surface of the top section 104 transitioning over a portion of the lateral edge of the superior surface and down the length of a portion of the lateral side of the top section 104.

In this example, the bottom section 104 includes features such as wireless charger access 105, joint 106, and grease isolation wall 109. Also illustrated, but not specifically identified, is the case screw base for receiving case screw 108 as well as various features within the grease isolation wall 109 for holding portions of a drive mechanism. The grease isolation wall 109 is designed to retain grease or similar compounds surrounding the drive mechanism away from the electrical components of the lacing engine 10 including the gear motor and enclosed gear box.

FIG. 2C is an illustration of various internal components of lacing engine 10, according to example embodiments. In this example, the lacing engine 10 further includes spool magnet 136, O-ring seal 138, worm drive 140, bushing 141, worm drive key 142, gear box 144, gear motor 145, motor encoder 146, motor circuit board 147, worm gear 150, circuit board 160, motor header 161, battery connection 162, and wired charging header 163. The spool magnet 136 assists in tracking movement of the spool 130 though detection by a magnetometer (not shown in FIG. 2C). The o-ring seal 138 functions to seal out dirt and moisture that could migrate into the lacing engine 10 around the spool shaft 133.

In this example, major drive components of the lacing engine 10 include worm drive 140, worm gear 150, gear motor 145 and gear box 144. The worm gear 150 is designed to inhibit back driving of worm drive 140 and gear motor 145, which means the major input forces coming in from the lacing cable via the spool 130 are resolved on the comparatively large worm gear and worm drive teeth. This arrangement protects the gear box 144 from needing to include gears of sufficient strength to withstand both the dynamic loading from active use of the footwear platform or tightening loading from tightening the lacing system. The worm drive 140 includes additional features to assist in protecting the more fragile portions of the drive system, such as the worm drive key 142. In this example, the worm drive key 142 is a radial slot in the motor end of the worm drive 140 that interfaces with a pin through the drive shaft coming out of the gear box 144. This arrangement prevents the worm drive 140 from imparting any axial forces on the gear box 144 or gear motor 145 by allowing the worm drive 140 to move freely in an axial direction (away from the gear box 144) transferring those axial loads onto bushing 141 and the housing structure 100.

FIG. 2D is an illustration depicting additional internal components of the lacing engine 10. In this example, the lacing engine 10 includes drive components such as worm drive 140, bushing 141, gear box 144, gear motor 145, motor encoder 146, motor circuit board 147 and worm gear 150. FIG. 2D adds illustration of battery 170 as well as a better view of some of the drive components discussed above.

FIG. 2E is another illustration depicting internal components of the lacing engine 10. In FIG. 2E the worm gear 150 is removed to better illustrate the indexing wheel 151 (also referred to as the Geneva wheel 151). The indexing wheel 151, as described in further detail below, provides a mechanism to home the drive mechanism in case of electrical or mechanical failure and loss of position. In this example, the lacing engine 10 also includes a wireless charging interconnect 165 and a wireless charging coil 166, which are located inferior to the battery 170 (which is not shown in this figure). In this example, the wireless charging coil 166 is mounted on an external inferior surface of the bottom section 104 of the lacing engine 10.

FIG. 2F is a cross-section illustration of the lacing engine 10, according to example embodiments. FIG. 2F assists in illustrating the structure of the spool 130 as well as how the lace grove 132 and lace channel 110 interface with lace cable 131. As shown in this example, lace 131 runs continuously through the lace channel 110 and into the lace grove 132 of the spool 130. The cross-section illustration also depicts lace recess 135, which is where the lace 131 will build up as it is taken up by rotation of the spool 130. The lace 131 is captured by the lace groove 132 as it runs across the lacing engine 10, so that when the spool 130 is turned, the lace 131 is rotated onto a body of the spool 130 within the lace recess 135.

As illustrated by the cross-section of lacing engine 10, the spool 130 includes a spool shaft 133 that couples with worm gear 150 after running through an O-ring 138. In this example, the spool shaft 133 is coupled to the worm gear via keyed connection pin 134. In some examples, the keyed connection pin 134 only extends from the spool shaft 133 in one axial direction, and is contacted by a key on the worm gear in such a way as to allow for an almost complete revolution of the worm gear 150 before the keyed connection pin 134 is contacted when the direction of worm gear 150 is reversed. A clutch system could also be implemented to couple the spool 130 to the worm gear 150. In such an example, the clutch mechanism could be deactivated to allow the spool 130 to run free upon de-lacing (loosening). In the example of the keyed connection pin 134 only extending is one axial direction from the spool shaft 133, the spool is allowed to move freely upon initial activation of a de-lacing process, while the worm gear 150 is driven backward. Allowing the spool 130 to move freely during the initial portion of a de-lacing process assists in preventing tangles in the lace 131 as it provides time for the user to begin loosening the footwear, which in turn will tension the lace 131 in the loosening direction prior to being driven by the worm gear 150.

FIG. 2G is another cross-section illustration of the lacing engine 10, according to example embodiments. FIG. 2G illustrates a more medial cross-section of the lacing engine 10, as compared to FIG. 2F, which illustrates additional components such as circuit board 160, wireless charging interconnect 165, and wireless charging coil 166. FIG. 2G is also used to depict additional detail surround the spool 130 and lace 131 interface.

FIG. 2H is a top view of the lacing engine 10, according to example embodiments. FIG. 2H emphasizes the grease isolation wall 109 and illustrates how the grease isolation wall 109 surrounds certain portions of the drive mechanism, including spool 130, worm gear 150, worm drive 140, and gear box 145. In certain examples, the grease isolation wall 109 separates worm drive 140 from gear box 145. FIG. 2H also provides a top view of the interface between spool 130 and lace cable 131, with the lace cable 131 running in a medial-lateral direction through lace groove 132 in spool 130.

FIG. 2I is a top view illustration of the worm gear 150 and index wheel 151 portions of lacing engine 10, according to example embodiments. The index wheel 151 is a variation on the well-known Geneva wheel used in watchmaking and film projectors. A typical Geneva wheel or drive mechanism provides a method of translating continuous rotational movement into intermittent motion, such as is needed in a film projector or to make the second hand of a watch move intermittently. Watchmakers used a different type of Geneva wheel to prevent over-winding of a mechanical watch spring, but using a Geneva wheel with a missing slot (e.g., one of the Geneva slots 157 would be missing). The missing slot would prevent further indexing of the Geneva wheel, which was responsible for winding the spring and prevents over-winding. In the illustrated example, the lacing engine 10 includes a variation on the Geneva wheel, indexing wheel 151, which includes a small stop tooth 156 that acts as a stopping mechanism in a homing operation. As illustrated in FIGS. 2J-2M, the standard Geneva teeth 155 simply index for each rotation of the worm gear 150 when the index tooth 152 engages the Geneva slot 157 next to one of the Geneva teeth 155. However, when the index tooth 152 engages the Geneva slot 157 next to the stop tooth 156 a larger force is generated, which can be used to stall the drive mechanism in a homing operation. The stop tooth 156 can be used to create a known location of the mechanism for homing in case of loss of other positioning information, such as the motor encoder 146.

FIG. 2J-2M are illustrations of the worm gear 150 and index wheel 151 moving through an index operation, according to example embodiments. As discussed above, these figures illustrate what happens during a single full revolution of the worm gear 150 starting with FIG. 2J though FIG. 2M. In FIG. 2J, the index tooth 153 of the worm gear 150 is engaged in the Geneva slot 157 between a first Geneva tooth 155a of the Geneva teeth 155 and the stop tooth 156. FIG. 2K illustrates the index wheel 151 in a first index position, which is maintained as the index tooth 153 starts its revolution with the worm gear 150, In FIG. 2L, the index tooth 153 begins to engage the Geneva slot 157 on the opposite side of the first Geneva tooth 155a. Finally, in FIG. 2M the index tooth 153 is fully engaged within a Geneva lot 157 between the first Geneva tooth 155a and a second Geneva tooth 155b. The process shown in FIGS. 2J-2M continues with each revolution of the worm gear 150 until the index tooth 153 engages the stop tooth 156. As discussed above, wen the index tooth 153 engages the stop tooth 156, the increased forces can stall the drive mechanism.

FIG. 2N is an exploded view of lacing engine 10, according to example embodiments. The exploded view of the lacing engine 10 provides an illustration of how all the various components fit together. FIG. 2N shows the lacing engine 10 upside down, with the bottom section 104 at the top of the page and the top section 102 near the bottom. In this example, the wireless charging coil 166 is shown as being adhered to the outside (bottom) of the bottom section 104. The exploded view also provide a good illustration of how the worm drive 140 is assembled with the bushing 141, drive shaft 143, gear box 144 and gear motor 145. The illustration does not include a drive shaft pin that is received within the worm drive key 142 on a first end of the worm drive 140. As discussed above, the worm drive 140 slides over the drive shaft 143 to engage a drive shaft pin in the worm drive key 142, which is essentially a slot running transverse to the drive shaft 143 in a first end of the worm drive 140.

In an example, the housing structure 100 provides an air tight or hermetic seal around the components that are enclosed by the housing structure 100. In an example, the housing structure 100 encloses a separate, hermetically sealed cavity in which a pressure sensor can be disposed. See FIG. 17 and the corresponding discussion below regarding a pressure sensor disposed in a sealed cavity.

Figure 3A:
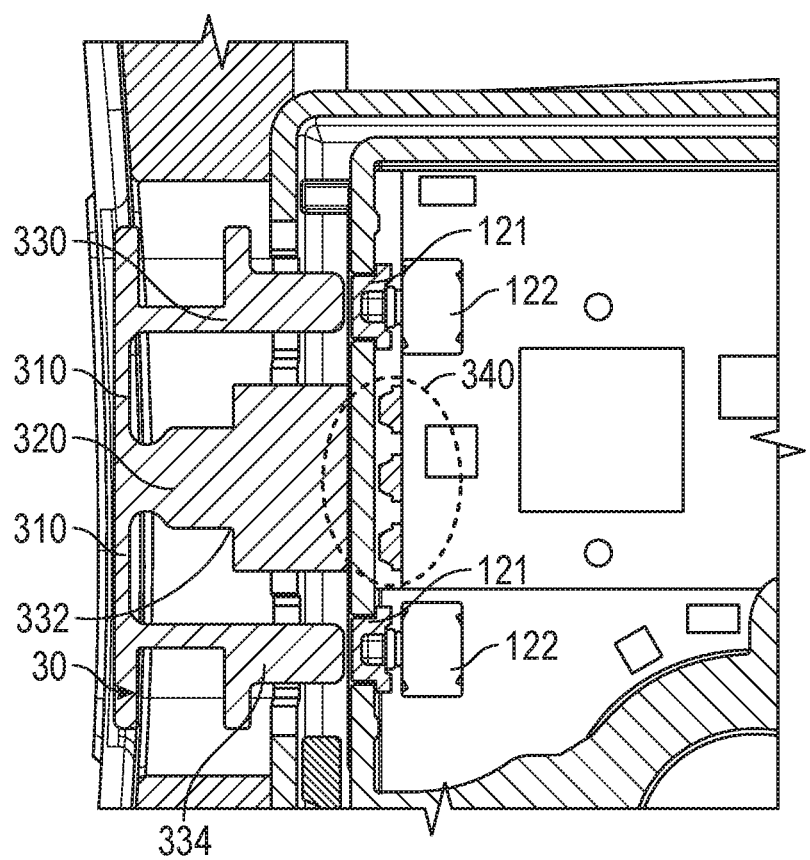
FIGS. 3A-3D are diagrams and drawings illustrating an actuator for interfacing with a motorized lacing engine, according to some example embodiments.

FIGS. 3A-3D illustrate generally examples of an actuator 30 for interfacing with a motorized lacing engine, according to an example embodiment. In this example, the actuator 30 includes features such as bridge 310, light pipe 320, posterior arm 330, central arm 332, and anterior arm 334. FIG. 3A also illustrates related features of lacing engine 10, such as LEDs 340 (also referenced as LED 340), buttons 121 and switches 122, In this example, the posterior arm 330 and anterior arm 334 each can separately activate one of the switches 122 through buttons 121. The actuator 30 is also designed to enable activation of both switches 122 simultaneously, for things like reset or other functions. The primary function of the actuator 30 is to provide tightening and loosening commands to the lacing engine 10. The actuator 30 also includes a light pipe 320 that directs light from LEDs 340 out to the external portion of the footwear platform (e.g., outsole 60). The light pipe 320 is structured to disperse light from multiple individual LED sources evening across the face of actuator 30.

In this example, the arms of the actuator 30, posterior arm 330 and anterior arm 334, include flanges to prevent over activation of switches 122 providing a measure of safety against impacts against the side of the footwear platform. The large central arm 332 is also designed to carry impact loads against the side of the lacing engine 10, instead of allowing transmission of these loads against the buttons 121.

Figure 3B:
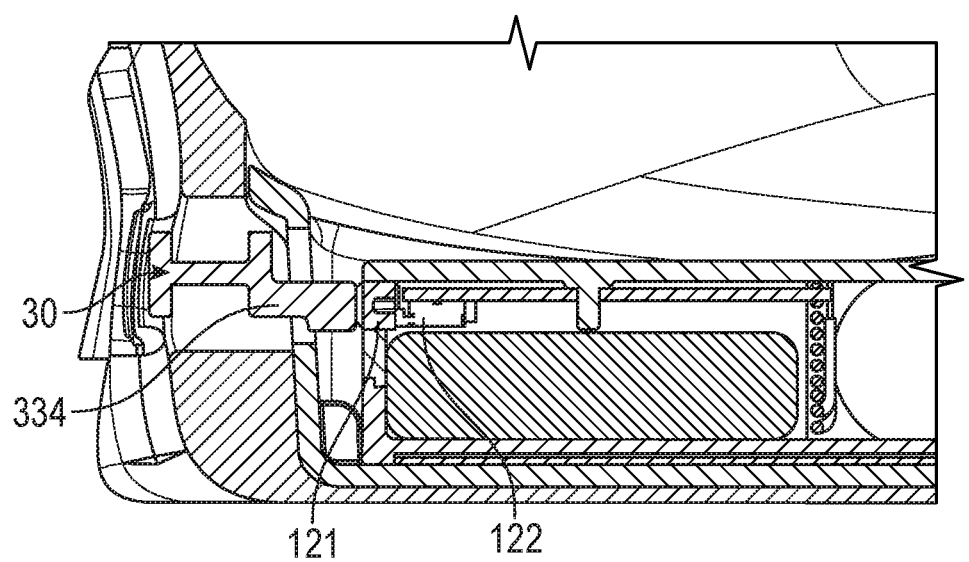
Figure 3C:
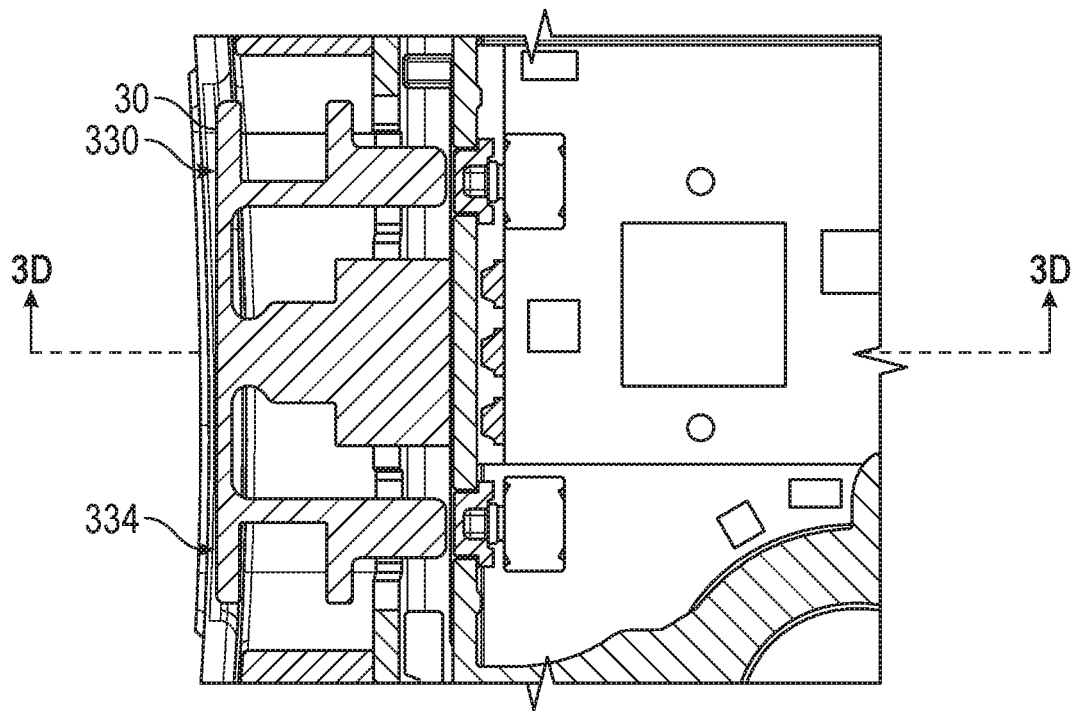
Figure 3D:
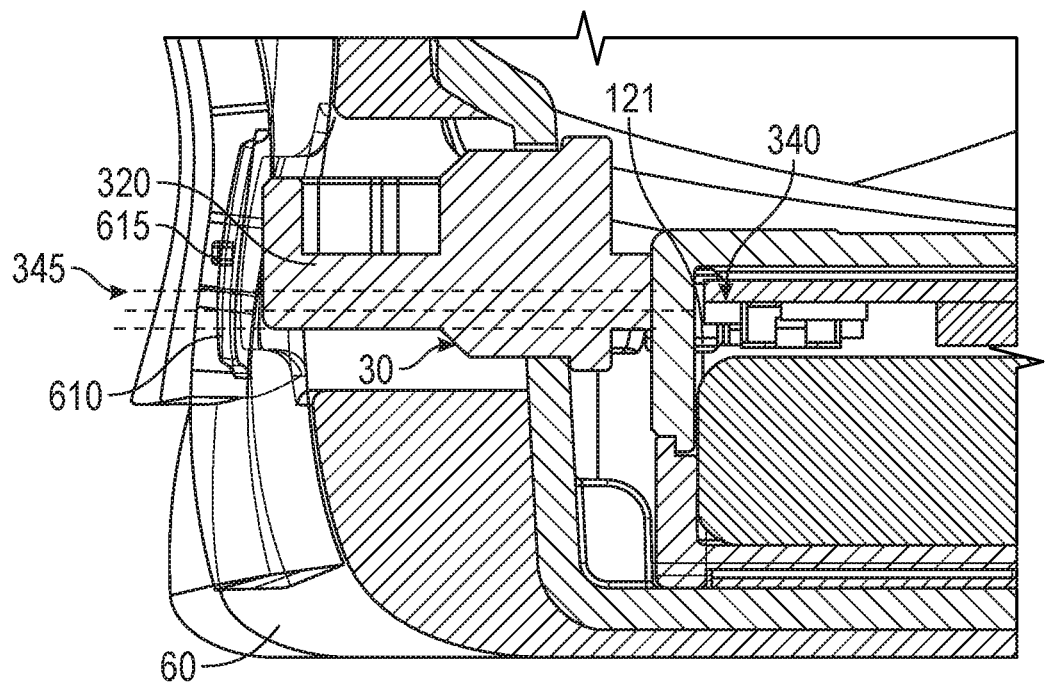

FIG. 3B provides a side view of the actuator 30, which further illustrates an example structure of anterior arm 334 and engagement with button 121. FIG. 3C is an additional top view of actuator 30 illustrating activation paths through posterior arm 330 and anterior arm 334. FIG. 3C also depicts section line A-A, which corresponds to the cross-section illustrated in FIG. 3D. In FIG. 3D, the actuator 30 is illustrated in cross-section with transmitted light 345 shown in dotted lines. The light pipe 320 provides a transmission medium for transmitted light 345 from LEDs 340. FIG. 3D also illustrates aspects of outsole 60, such as actuator cover 610 and raised actuator interface 615.

FIGS. 4A-4D are diagrams and drawings illustrating a mid-sole plate 40 for holding lacing engine 10, according to some example embodiments. In this example, the mid-sole plate 40 includes features such as lacing engine cavity 410, medial lace guide 420, lateral lace guide 421, lid slot 430, anterior flange 440, posterior flange 450, a superior surface 460, an inferior surface 470, and an actuator cutout 480. The lacing engine cavity 410 is designed to receive lacing engine 10. In this example, the lacing engine cavity 410 retains the lacing engine 10 is lateral and anterior/posterior directions, but does not include any built in feature to lock the lacing engine 10 in to the pocket. Optionally, the lacing engine cavity 410 can include detests, tabs, or similar mechanical features along one or more sidewalk that could positively retain the lacing engine 10 within the lacing engine cavity 410.

The medial lace guide 420 and lateral lace guide 421 assist in guiding lace cable into the lace engine pocket 410 and over lacing engine 10 (when present). The medial/lateral lace guides 420, 421 can include chamfered edges and inferiorly slated ramps to assist in guiding the lace cable into the desired position over the lacing engine 10. In this example, the medial/lateral lace guides 420, 421 include openings in the sides of the mid-sole plate 40 that are many times wider than the typical lacing cable diameter, in other examples the openings for the medial/lateral lace guides 420, 421 may only be a couple times wider than the lacing cable diameter.

In this example, the mid-sole plate 40 includes a sculpted or contoured anterior flange 440 that extends much further on the medial side of the mid-sole plate 40. The example anterior flange 440 is designed to provide additional support under the arch of the footwear platform. However, in other examples the anterior flange 440 may be less pronounced in on the medial side. In this example, the posterior flange 450 also includes a particular contour with extended portions on both the medial and lateral sides. The illustrated posterior flange 450 shape provides enhanced lateral stability for the lacing engine 10.

Figure 4A:
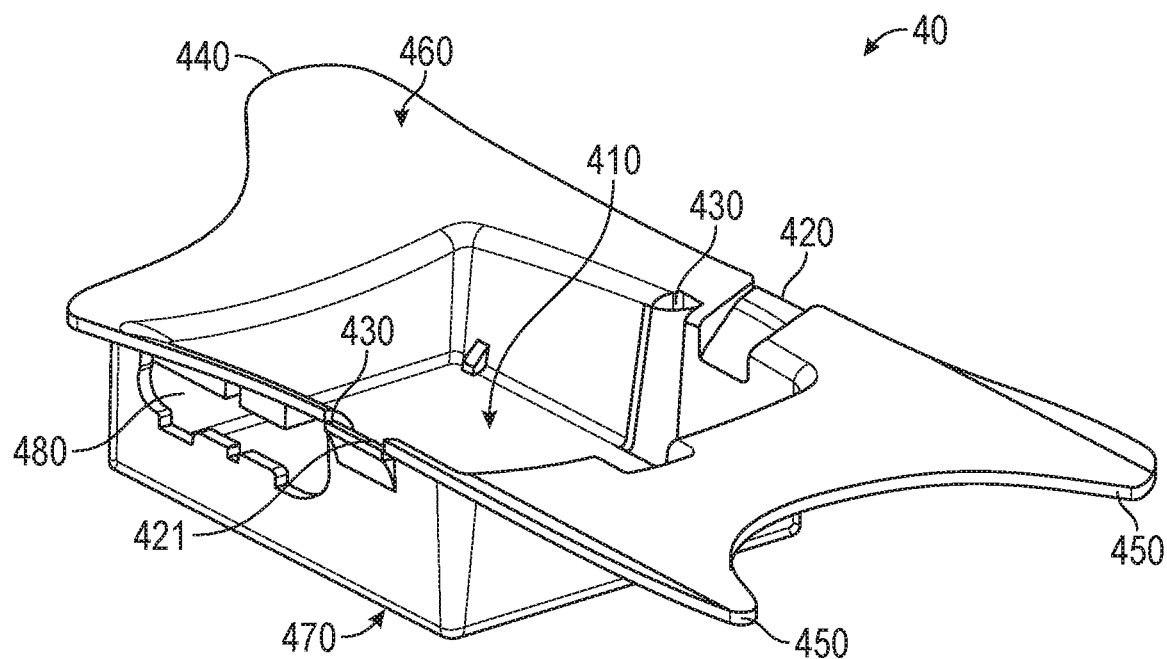
FIGS. 4A-4D are diagrams and drawings illustrating a mid-sole plate for holding a lacing engine, according to some example embodiments.
Figure 4B:
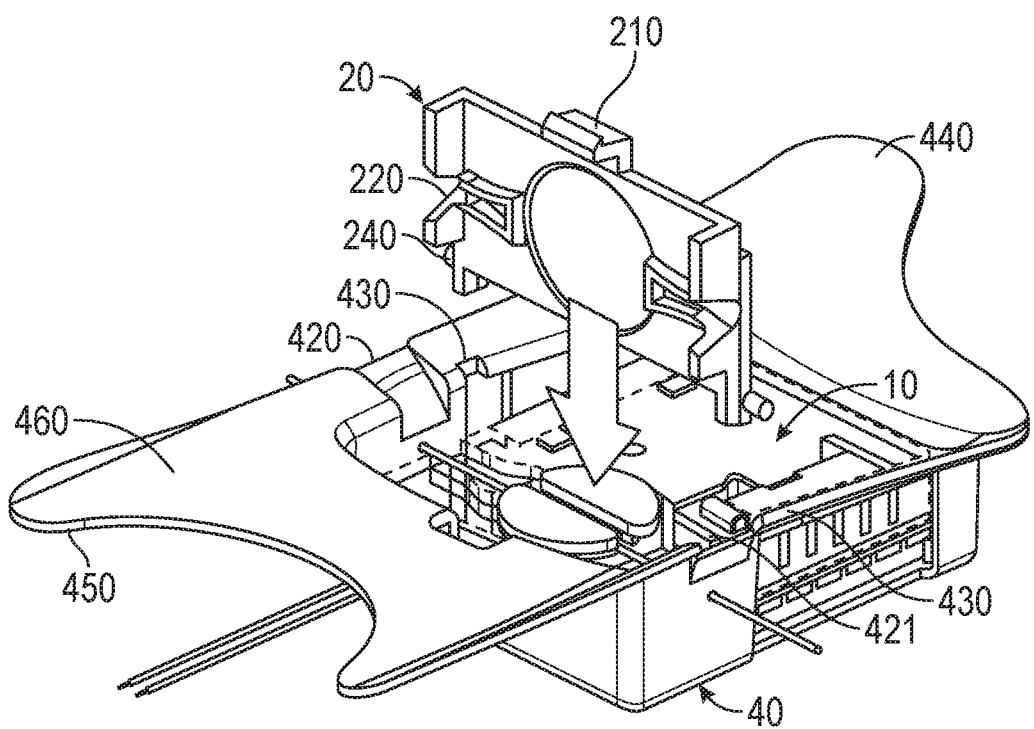
Figure 4C:
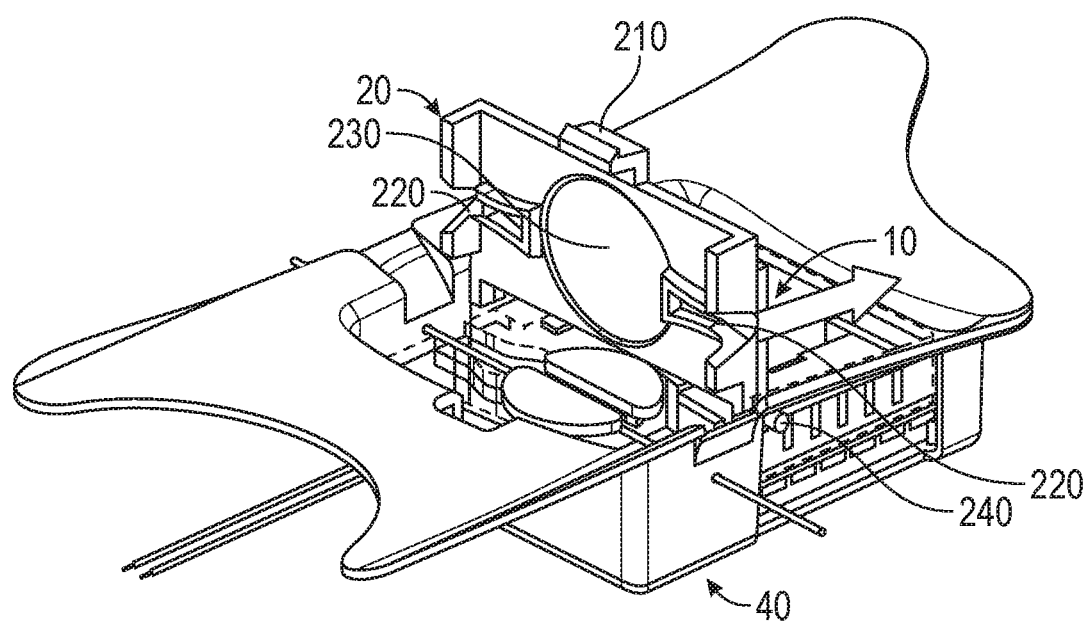
Figure 4D:
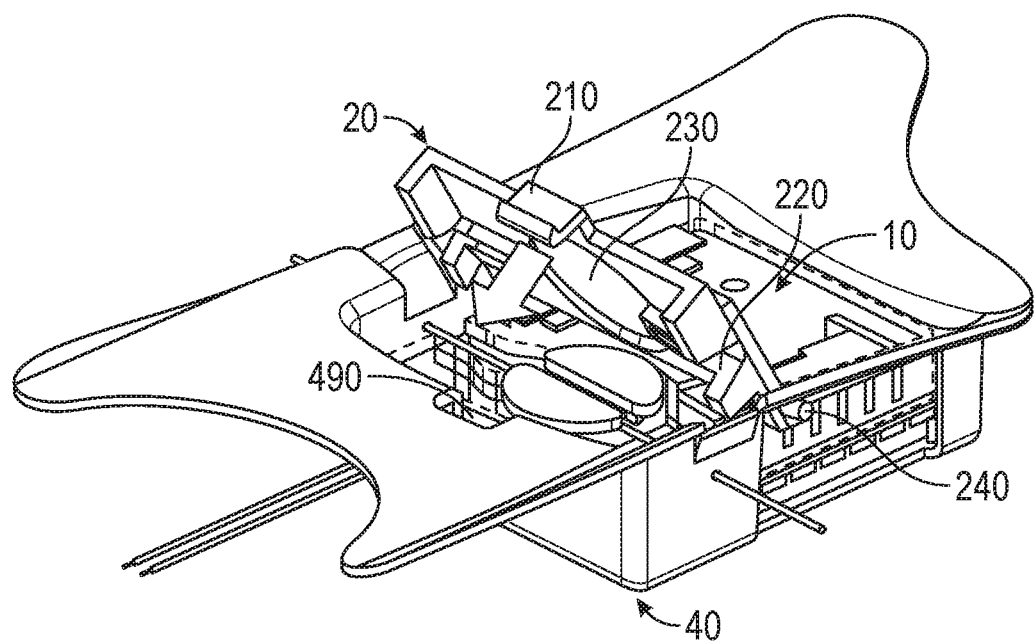

FIGS. 4B-4D illustrate insertion of the lid 20 into the mid-sole plate 40 to retain the lacing engine 10 and capture lace cable 131. In this example, the lid 20 includes features such as latch 210, lid lace guides 220, lid spool recess 230, and lid clips 240. The lid lace guides 220 can include both medial and lateral lid lace guides 220. The lid lace guides 220 assist in maintaining alignment of the lace cable 131 through the proper portion of the lacing engine 10. The lid clips 240 can also include both medial and lateral lid clips 240. The lid clips 240 provide a pivot point for attachment of the lid 20 to the mid-sole plate 40. As illustrated in FIG. 4B, the lid 20 is inserted straight down into the mid-sole plate 40 with the lid clips 240 entering the mid-sole plate 40 via the lid slots 430.

As illustrated in FIG. 4C, once the lid clips 240 are inserted through the lid slots 430, the lid 20 is shifted anteriorly to keep the lid clips 240 from disengaging from the mid-sole plate 40. FIG. 4D illustrates rotation or pivoting of the lid 20 about the lid clips 240 to secure the lacing engine 10 and lace cable 131 by engagement of the latch 210 with a lid latch recess 490 in the mid-sole plate 40. Once snapped into position, the lid 20 secures the lacing engine 10 within the mid-sole plate 40.

Figure 5A:
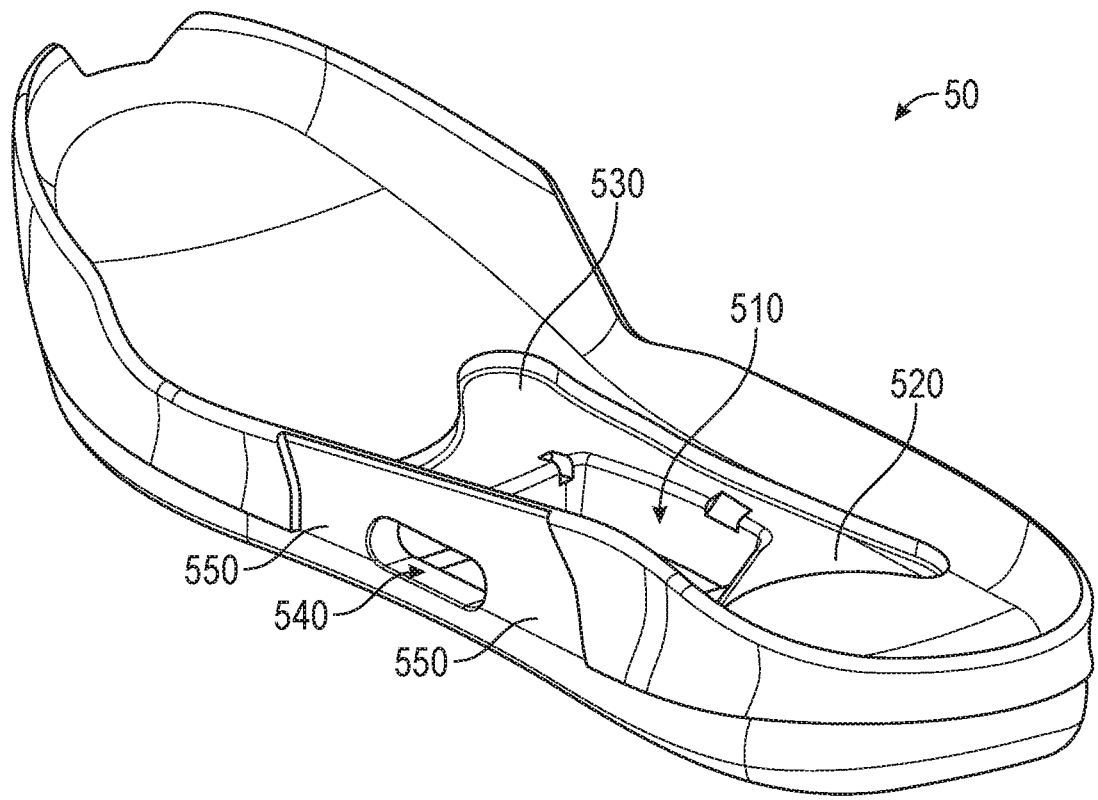
Figure 5B:
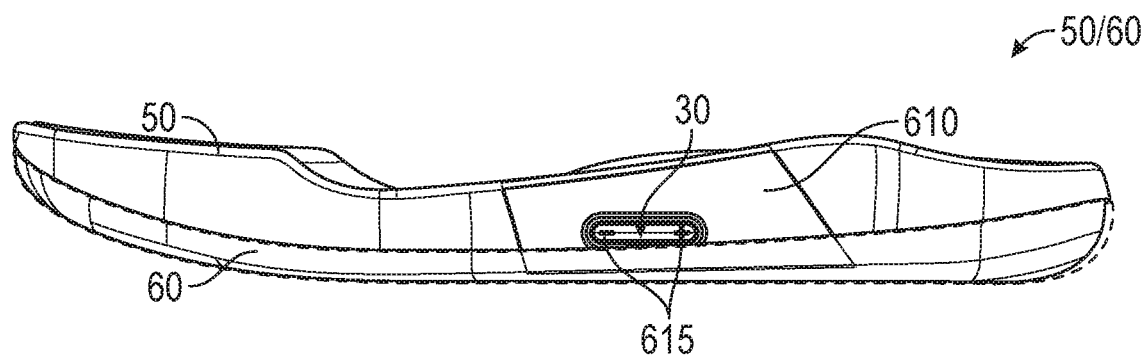

FIGS. 5A-5D are diagrams and drawings illustrating a mid-sole 50 and out-sole 60 configured to accommodate lacing engine 10 and related components, according to some example embodiments. The mid-sole 50 can be formed from any suitable footwear material and includes various features to accommodate the mid-sole plate 40 and related components. In this example, the mid-sole 50 includes features such as plate recess 510, anterior flange recess 520, posterior flange recess 530, actuator opening 540 and actuator cover recess 550. The plate recess 510 includes various cutouts and similar features to match corresponding features of the mid-sole plate 40. The actuator opening 540 is sized and positioned to provide access to the actuator 30 from the lateral side of the footwear platform 1. The actuator cover recess 550 is a recessed portion of the mid-sole 50 adapted to accommodate a molded covering to protect the actuator 30 and provide a particular tactile and visual look for the primary user interface to the lacing engine 10, as illustrated in FIGS. 5B and 5C.

FIGS. 5B and 5C illustrate portions of the mid-sole 50 and out-sole 60, according to example embodiments. FIG. 5B includes illustration of exemplary actuator cover 610 and raised actuator interface 615, which is molded or otherwise formed into the actuator cover 610. FIG. 5C illustrates an additional example of actuator 610 and raised actuator interface 615 including horizontal striping to disperse portions of the light transmitted to the out-sole 60 through the light pipe 320 portion of actuator 30.

FIG. 5D further illustrates actuator cover recess 550 on mid-sole 50 as well as positioning of actuator 30 within actuator opening 540 prior to application of actuator cover 610. In this example, the actuator cover recess 550 is designed to receive adhesive to adhere actuator cover 610 to the mid-sole 50 and out-sole 60.

Figure 6A:
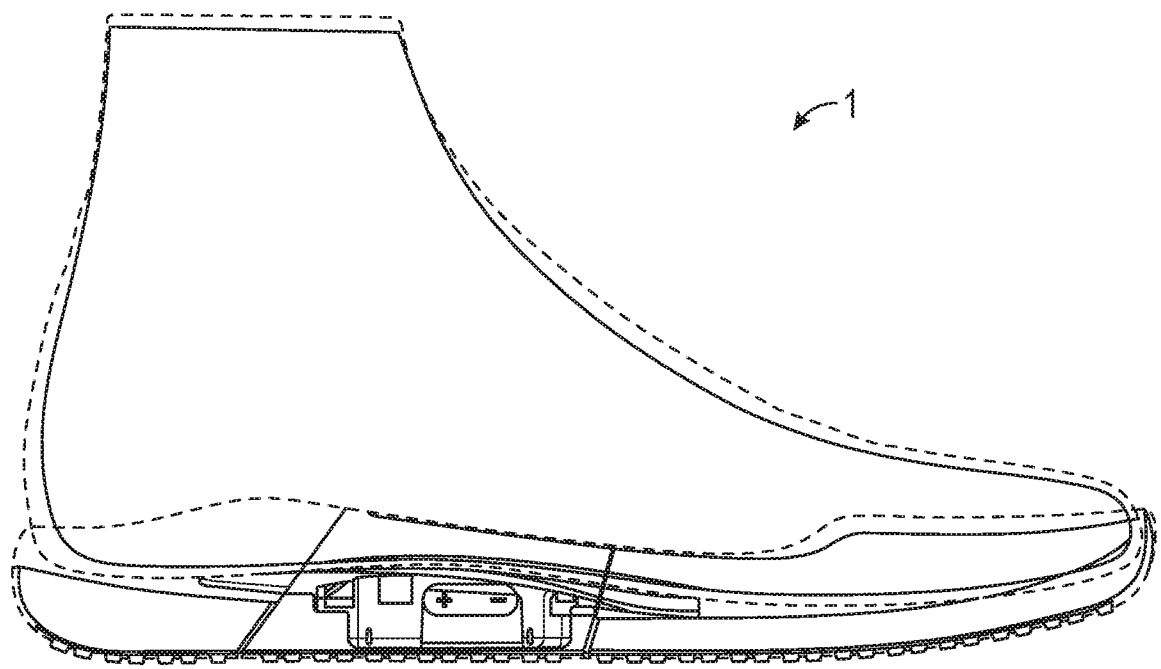
FIGS. 6A-6D are illustrations of a footwear assembly including a motorized lacing engine, according to some example embodiments.
Figure 6B:
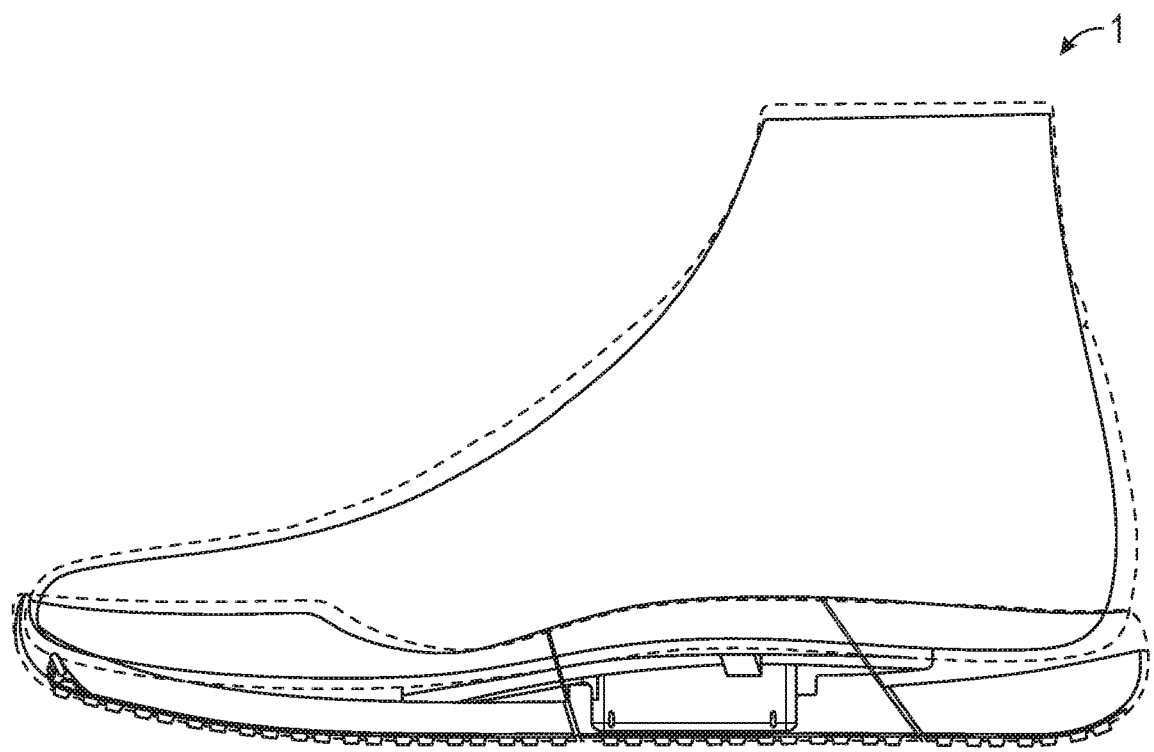
Figure 6C:
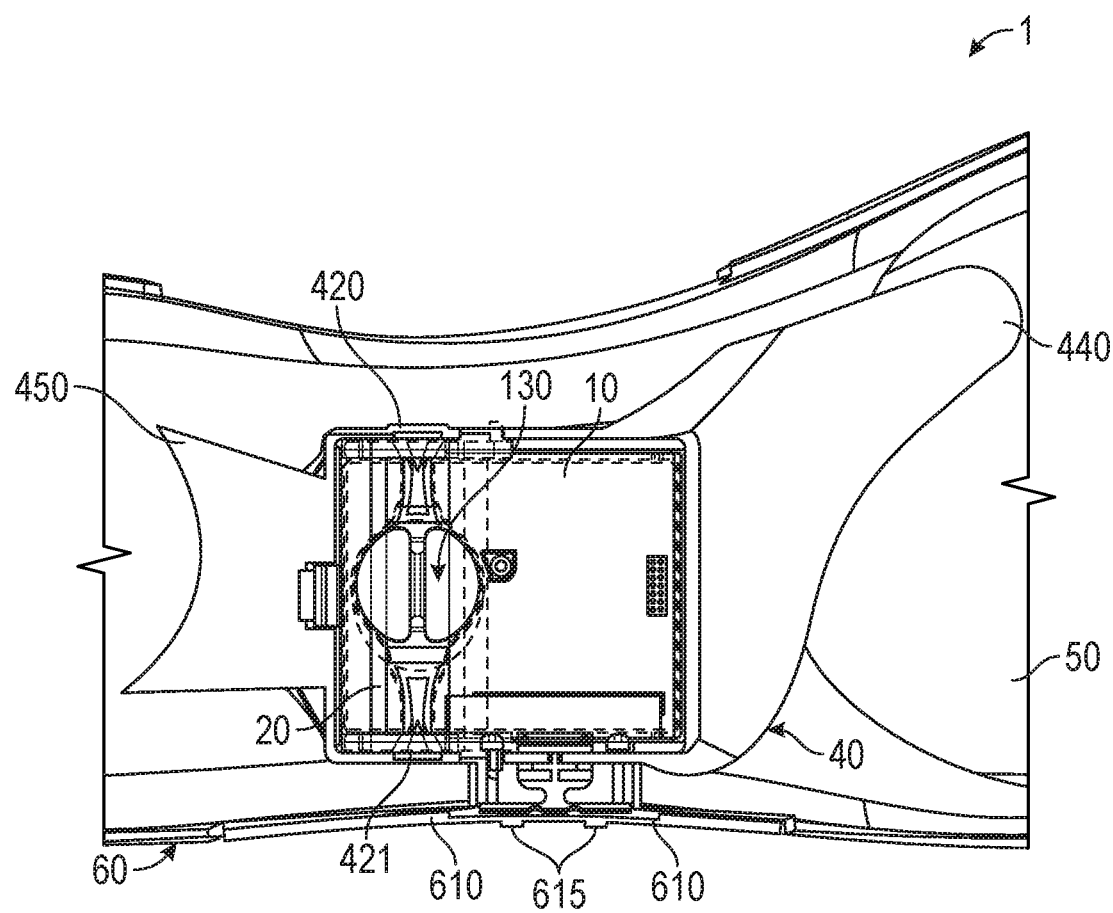

FIGS. 6A-6C are illustrations of a footwear assembly 1 including a motorized lacing engine 10, according to some example embodiments. In this example, FIGS. 6A-6C depict semi-transparent examples of an assembled automated footwear platform 1 including a lacing engine 10, a mid-sole plate 40, a mid-sole 50, and an out-sole 60. FIG. 6A is a lateral side view of the automated footwear platform 1. FIG. 6B is a medial side view of the automated footwear platform 1. FIG. 6C is a top view, with the upper portion removed, of the automated footwear platform 1. The top view demonstrates relative positioning of the lacing engine 10, the lid 20, the actuator 30, the mid-sole plate 40, the mid-sole 50, and the out-sole 60. In this example, the top view also illustrates the spool 130, the medial lace guide 420 the lateral lace guide 421, the anterior flange 440, the posterior flange 450, the actuator cover 610, and the raised actuator interface 615.

Figure 6D:
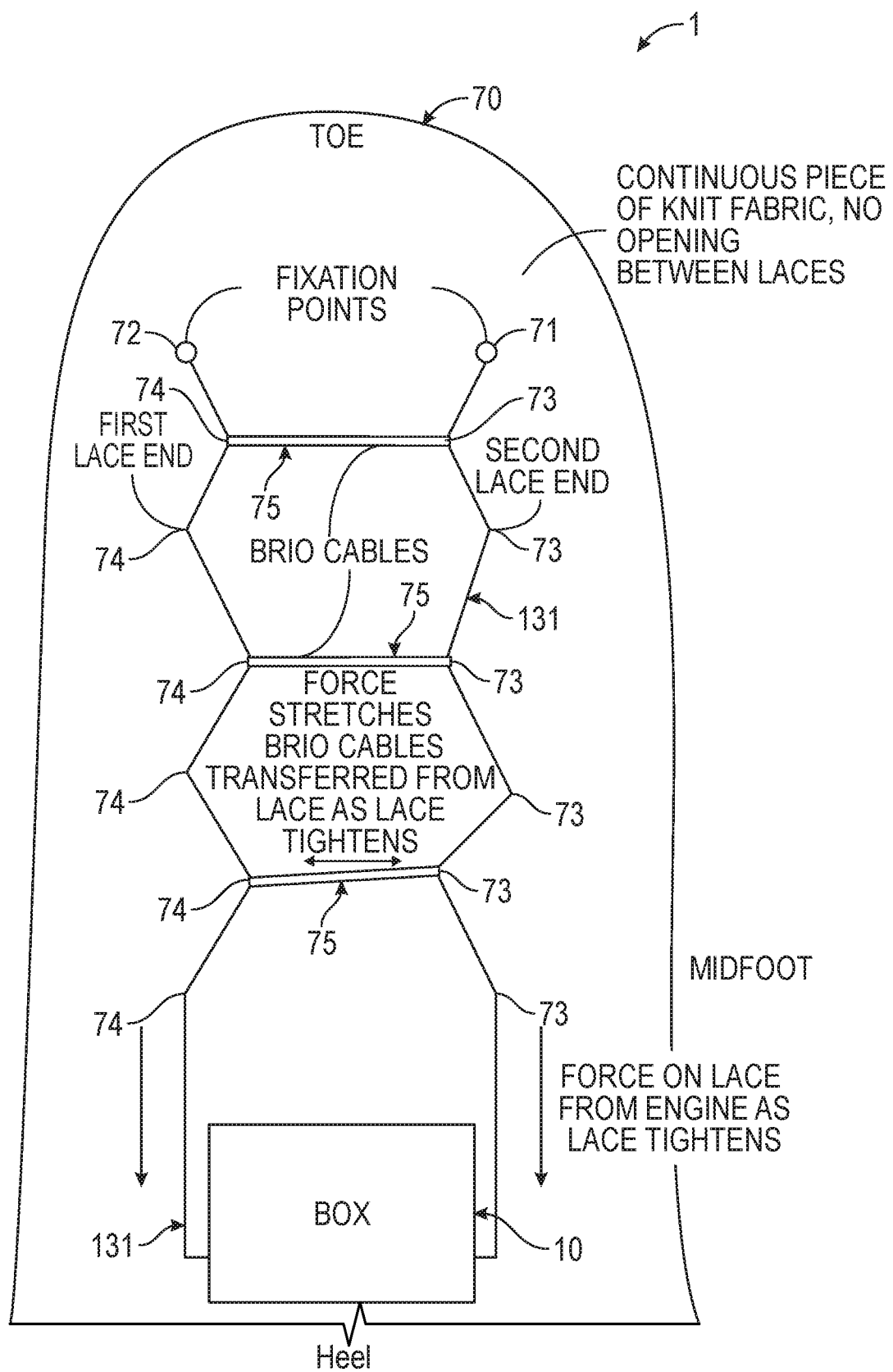

FIG. 6D is a top view diagram of upper 70 illustrating an example lacing configuration, according to some example embodiments. In this example, the upper 70 includes lateral lace fixation 71, medial lace fixation 72, lateral lace guides 73, medial lace guides 74, and brio cables 75, in additional to lace 131 and lacing engine 10. The example illustrated in FIG. 6D includes a continuous knit fabric upper 70 with diagonal lacing pattern involving non-overlapping medial and lateral lacing paths. The lacing paths are created starting at the lateral lace fixation running through the lateral lace guides 73 through the lacing engine 10 up through the medial lace guides 74 back to the medial lace fixation 72. In this example, lace 131 forms a continuous loop from lateral lace fixation 71 to medial lace fixation 72. Medial to lateral tightening is transmitted through brio cables 75 in this example. In other examples, the lacing path may crisscross or incorporate additional features to transmit tightening forces in a medial-lateral direction across the upper 70. Additionally, the continuous lace loop concept can be incorporated into a more traditional upper with a central (medial) gap and lace 131 crisscrossing back and forth across the central gap.

Figure 7:
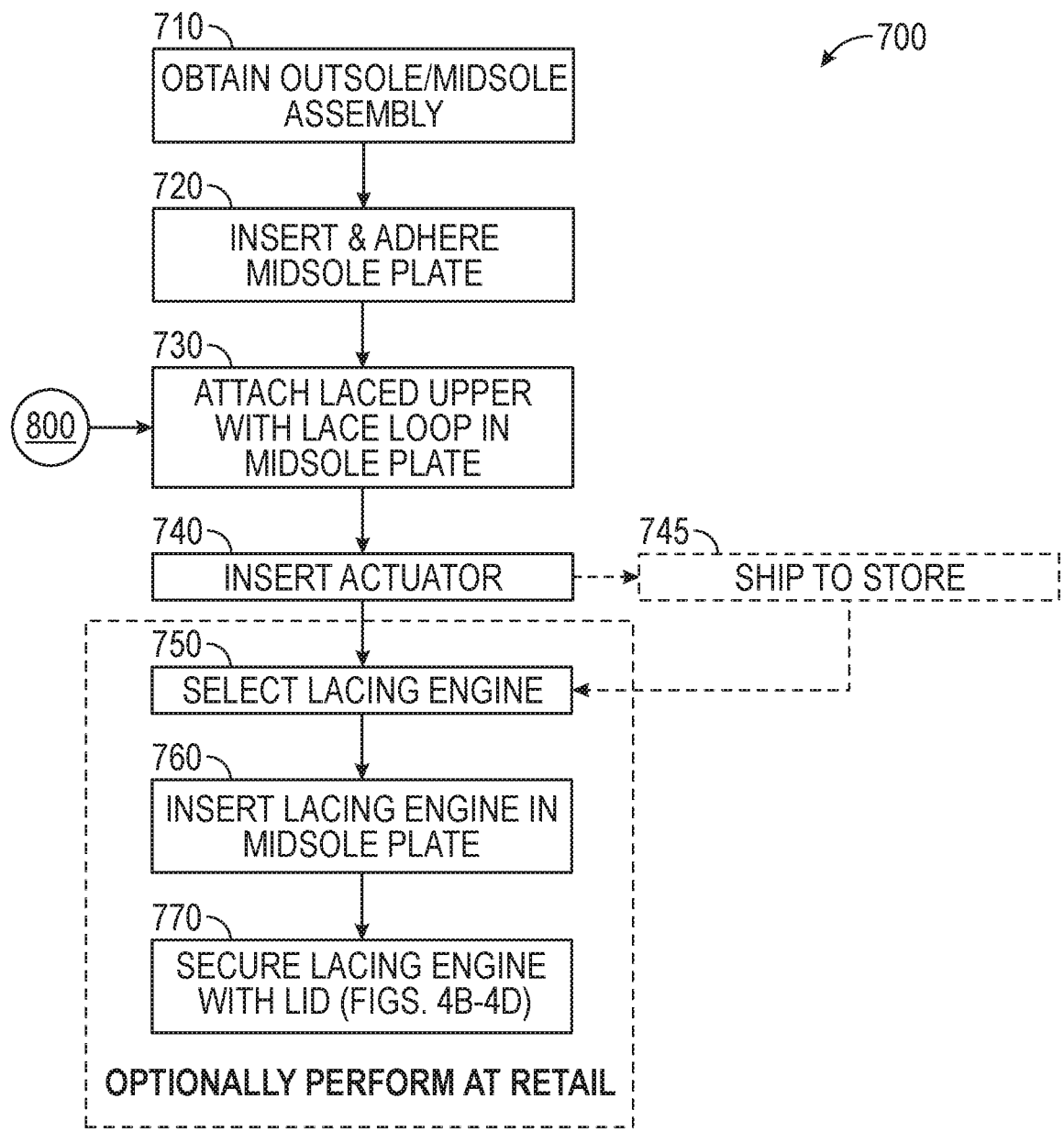
FIG. 7 is a flowchart illustrating a footwear assembly process for assembly of footwear including a lacing engine, according to some example embodiments.

FIG. 7 is a flowchart illustrating a footwear assembly process for assembly of an automated footwear platform 1 including lacing engine 10, according to some example embodiments. In this example, the assembly process includes operations such as: obtaining an outsole/midsole assembly at 710, inserting and adhering a mid-sole plate at 720, attaching laced upper at 730, inserting actuator at 740, optionally shipping the subassembly to a retail store at 745, selecting a lacing engine at 750, inserting a lacing engine into the mid-sole plate at 760, and securing the lacing engine at 770. The process 700 described in further detail below can include some or all of the process operations described and at least some of the process operations can occur at various locations (e.g., manufacturing plant versus retail store). In certain examples, all of the process operations discussed in reference to process 700 can be completed within a manufacturing location with a completed automated footwear platform delivered directly to a consumer or to a retain location for purchase.

In this example, the process 700 begins at 710 with obtaining an out-sole and mid-sole assembly, such as mid-sole 50 adhered to out-sole 60. At 720, the process 700 continues with insertion of a mid-sole plate, such as mid-sole plate 40, into a plate recess 510. In some examples, the mid-sole plate 40 includes a layer of adhesive on the inferior surface to adhere the mid-sole plate into the mid-sole. In other examples, adhesive is applied to the mid-sole prior to insertion of a mid-sole plate. In still other examples, the mid-sole is designed with an interference fit with the mid-sole plate, which does not require adhesive to secure the two components of the automated footwear platform.

At 730, the process 700 continues with a laced upper portion of the automated footwear platform being attached to the mid-sole. Attachment of the laced upper portion is done through any known footwear manufacturing process, with the addition of positioning a lower lace loop into the mid-sole plate for subsequent engagement with a lacing engine, such as lacing engine 10. For example, attaching a laced upper to mid-sole 50 with mid-sole plate 40 inserted, the lower lace loop is positioned to align with medial lace guide 420 and lateral lace guide 421, which position the lace loop properly to engage with lacing engine 10 when inserted later in the assembly process. Assembly of the upper portion is discussed in greater detail in reference to FIGS. 8A-8B below.

At 740, the process 700 continues with insertion of an actuator, such as actuator 30, into the mid-sole plate. Optionally, insertion of the actuator can be done prior to attachment of the upper portion at operation 730. In an example, insertion of actuator 30 into the actuator cutout 480 of mid-sole plate 40 involves a snap fit between actuator 30 and actuator cutout 480. Optionally, process 700 continues at 745 with shipment of the subassembly of the automated footwear platform to a retail location or similar point of sale. The remaining operations within process 700 can be performed without special tools or materials, which allows for flexible customization of the product sold at the retail level without the need to manufacture and inventory every combination of automated footwear subassembly and lacing engine options.

At 750, the process 700 continues with selection of a lacing engine, which may be an optional operation in cases where only one lacing engine is available. In an example, lacing engine 10, a motorized lacing engine, is chosen for assembly into the subassembly from operations 710-740. However, as noted above, the automated footwear platform is designed to accommodate various types of lacing engines from fully automatic motorized lacing engines to human-power manually activated lacing engines. The subassembly built up in operations 710-740, with components such as out-sole 60, mid-sole 50, and mid-sole plate 40, provides a modular platform to accommodate a wide range of optional automation components.

At 760, the process 700 continues with insertion of the selected lacing engine into the mid-sole plate. For example, lacing engine 10 can be inserted into mid-sole plate 40, with the lacing engine 10 slipped underneath the lace loop running through the lacing engine cavity 410. With the lacing engine 10 in place and the lace cable engaged within the spool of the lacing engine, such as spool 130, a lid (or similar component) can be installed into the mid-sole plate to secure the lacing engine 10 and lace. An example of install of lid 20 into mid-sole plate 40 to secure lacing engine 10 is illustrated in FIGS. 4B-4D and discussed above. With the lid secured over the lacing engine, the automated footwear platform is complete and ready for active use.

Figure 8A:
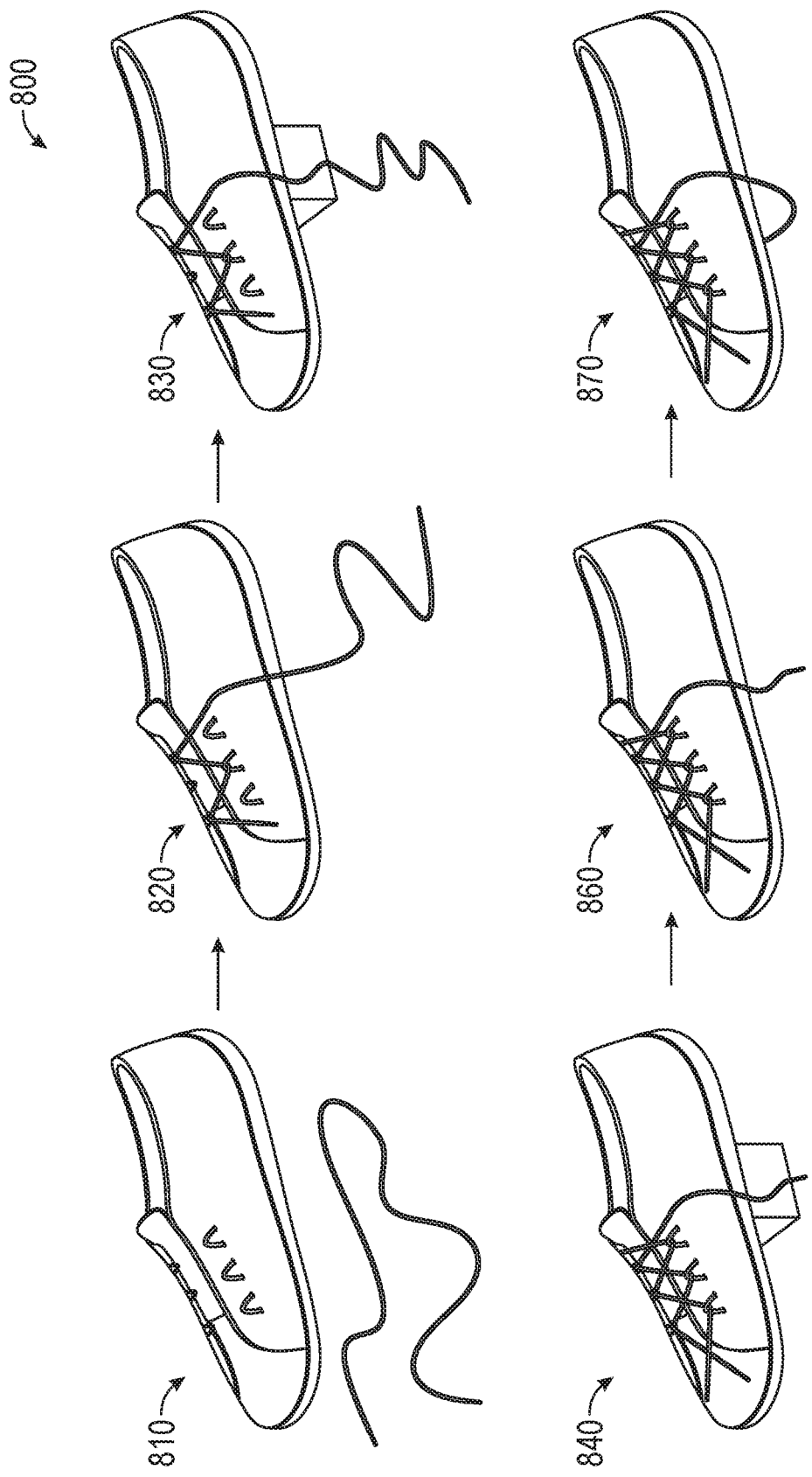
FIGS. 8A-8B is a drawing and a flowchart illustrating an assembly process for assembly of a footwear upper in preparation for assembly to mid-sole, according to some example embodiments.
Figure 8B:
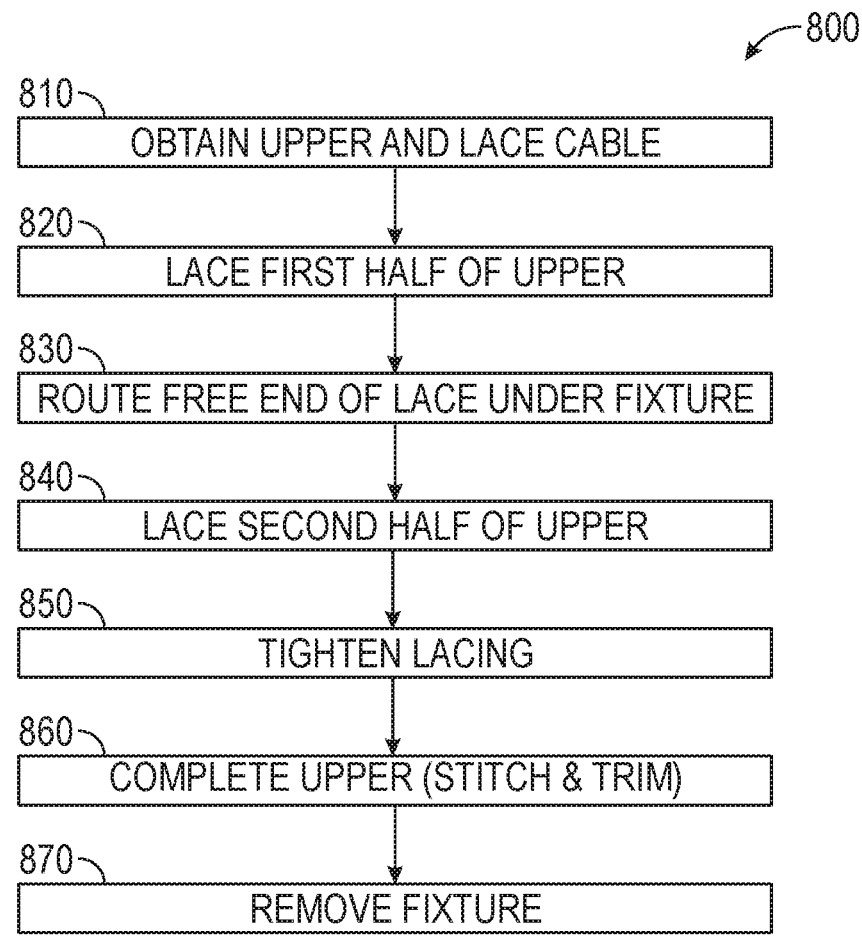

FIGS. 8A-8B include flowcharts illustrating generally an assembly process 800 for assembly of a footwear upper in preparation for assembly to a mid-sole, according to some example embodiments.

FIG. 8A visually depicts a series of assembly operations to assembly a laced upper portion of a footwear assembly for eventual assembly into an automated footwear platform, such as though process 700 discussed above. Process 800 illustrated in FIG. 8A starts with operation 1, which involves obtaining a knit upper and a lace (lace cable). Next, a first half of the knit upper is laced with the lace. In this example, lacing the upper involves threading the lace cable through a number of eyelets and securing one end to an anterior section of the upper. Next, the lace cable is routed under a fixture supporting the upper and around to the opposite side. Then, at operation 2.6, the other half of the upper is laced, while maintaining a lower loop of lace around the fixture. At 2.7, the lace is secured and trimmed and at 3.0 the fixture is removed to leave a laced knit upper with a lower lace loop under the upper portion.

FIG. 8B is a flowchart illustrating another example of process 800 for assembly of a footwear upper. In this example, the process 800 includes operations such as obtaining an upper and lace cable at 810, lacing the first half of the upper at 820, routing the lace under a lacing fixture at 830, lacing the second half of the upper at 840, tightening the lacing at 850, completing upper at 860, and removing the lacing fixture at 870.

The process 800 begins at 810 by obtaining an upper and a lace cable to being assembly. Obtaining the upper can include placing the upper on a lacing fixture used through other operations of process 800. At 820, the process 800 continues by lacing a first half of the upper with the lace cable. Lacing operation can include routing the lace cable through a series of eyelets or similar features built into the upper. The lacing operation at 820 can also include securing one end of the lace cable to a portion of the upper. Securing the lace cable can include sewing, tying off, or otherwise terminating a first end of the lace cable to a fixed portion of the upper.

At 830, the process 800 continues with routing the free end of the lace cable under the upper and around the lacing fixture. In this example, the lacing fixture is used to create a proper lace loop under the upper for eventual engagement with a lacing engine after the upper is joined with a mid-sole/out-sole assembly (see discussion of FIG. 7 above). The lacing fixture can include a groove or similar feature to at least partially retain the lace cable during the sequent operations of process 800.

At 840, the process 800 continues with lacing the second half of the upper with the free end of the lace cable. Lacing the second half can include routing the lace cable through a second series of eyelets or similar features on the second half of the upper. At 850, the process 800 continues by tightening the lace cable through the various eyelets and around the lacing fixture to ensure that the lower lace loop is properly formed for proper engagement with a lacing engine. The lacing fixture assists in obtaining a proper lace loop length, and different lacing fixtures can be used for different size or styles of footwear. The lacing process is completed at 860 with the free end of the lace cable being secured to the second half of the upper. Completion of the upper can also include additional trimming or stitching operations. Finally, at 870, the process 800 completes with removal of the upper from the lacing fixture.

Figure 9:
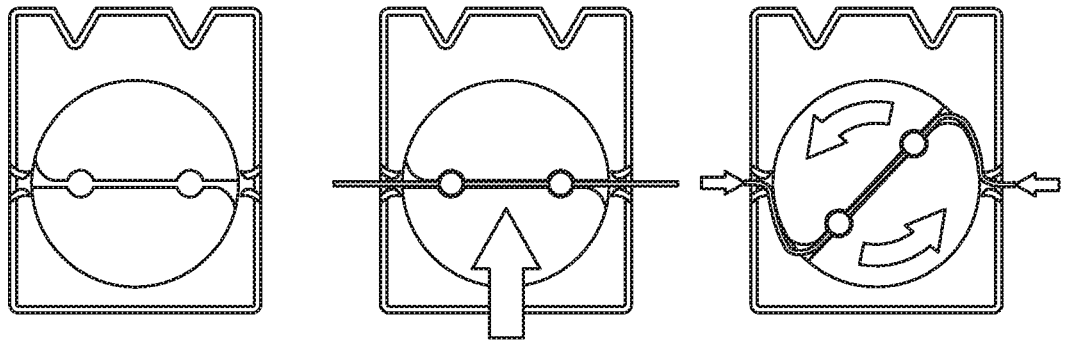
FIG. 9 is a drawing illustrating a mechanism for securing a lace within a spool of a lacing engine, according to some example embodiments.

FIG. 9 is a drawing illustrating a mechanism for securing a lace within a spool of a lacing engine, according to some example embodiments. In this example, spool 130 of lacing engine 10 receives lace cable 131 within lace grove 132. FIG. 9 includes a lace cable with ferrules and a spool with a lace groove that include recesses to receive the ferrules. In this example, the ferrules snap (e.g., interference fit) into recesses to assist in retaining the lace cable within the spool. Other example spools, such as spool 130, do not include recesses and other components of the automated footwear platform are used to retain the lace cable in the lace groove of the spool.

Figure 10A:
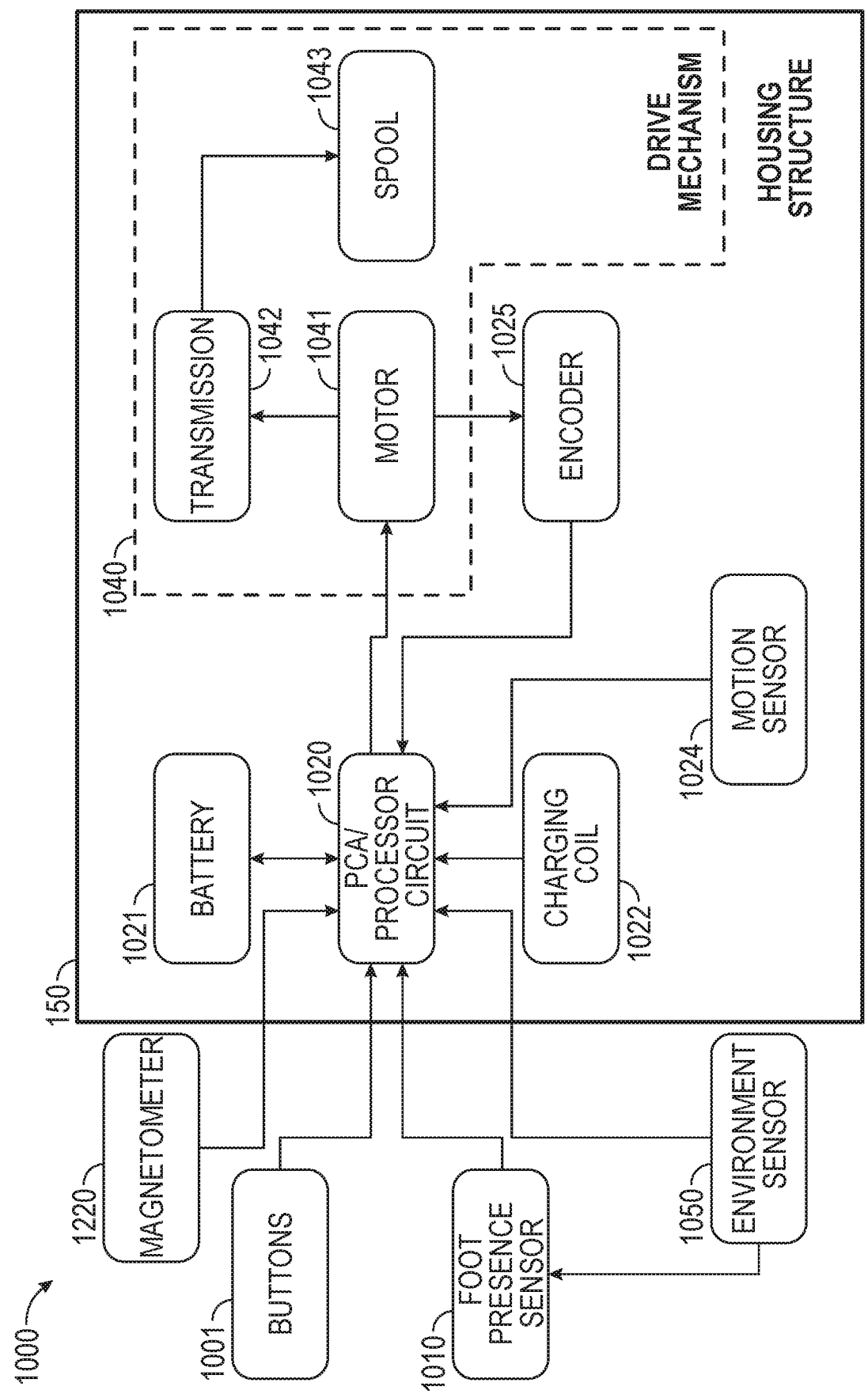
FIG. 10A is a block diagram illustrating components of a motorized lacing system, according to some example embodiments.

FIG. 10A illustrates generally a block diagram of components of a motorized lacing system 1000, according to an example embodiment. The system 1000 includes some, but not necessarily all, components of a motorized lacing system such as including interface buttons 1001 (e.g., corresponding to the buttons 121 in the example of FIG. 2A), a foot presence sensor 1010, and the housing structure 100 enclosing a printed circuit board assembly (PCA) with a processor circuit 1020, a battery 1021, a charging coil 1022, an encoder 1025, a motion sensor 1024, and a drive mechanism 1040. The drive mechanism 1040 can include, among other things, a motor 1041, a transmission 1042, and a lace spool 1043. The motion sensor 1024 can include, among other things, a single or multiple axis accelerometer, a magnetometer, a pyrometer, or other sensor or device configured to sense motion of the housing structure 150, or of one or more components within or coupled to the housing structure 150. In an example, the system 1000 includes a magnetometer 1220 coupled to the processor circuit 1020.

In the example of FIG. 10A, the processor circuit 1020 is in data or power signal communication with one or more of the interface buttons 1001, foot presence sensor 1010, battery 1021, charging coil 1022, and drive mechanism 1040. The transmission 1042 couples the motor 1041 to the spool 1043 to form the drive mechanism 1040. In the example of FIG. 10A, the buttons 1001, foot presence sensor 1010, and environment sensor 1050 are shown outside of, or partially outside of, the housing structure 100.

In alternative embodiments, one or more of the buttons 1001, foot presence sensor 1010, and environment sensor 1050 can be enclosed in the housing structure 100. In an example, the foot presence sensor 1010 is preferably disposed inside of the housing structure 100 to protect the sensor from perspiration and dirt or debris. Minimizing or eliminating connections through the walls of the housing structure 100 can help increase durability and reliability of the assembly.

In an example, the processor circuit 1020 controls one or more aspects of the drive mechanism 1040. For example, the processor circuit 1020 can be configured to receive information from the buttons 1001 and/or from the foot presence sensor 1010 and/or from the motion sensor 1024 and, in response, control the drive mechanism 1040, such as to tighten or loosen footwear about a foot. In an example, the processor circuit 1020 is additionally or alternatively configured to issue commands to obtain or record sensor information, from the foot presence sensor 1010 or other sensor, among other functions. In an example, the processor circuit 1020 conditions operation of the drive mechanism 1040 on (1) detecting a foot presence using the foot presence sensor 1010 and (2) detecting a specified gesture using the motion sensor 1024.

In an example, the system 1000 includes an environment sensor 1050. Information from the environment sensor 1050 can be used to update or adjust a baseline or reference value for the foot presence sensor 1010. As further explained below, capacitance values measured by a capacitive foot presence sensor can vary over time, such as in response to ambient conditions near the sensor. Using information from the environment sensor 1050, the processor circuit 1020 and/or the foot presence sensor 1010 can update or adjust a measured or sensed capacitance value.

In an example, the system 1000 includes sensors configured to collect different types of data. In an example, the sensor(s) collect data regarding a number, sequence, and/or frequency of compressions of the insole 1201 (see, e.g., discussion of FIGS. 12A-12G). For example, the system 1000 can record a number or frequency of steps, jumps, cuts, kicks, or other compressive forces incurred while a wearer wears the footwear, as well as other parameters, such as contact time and flight time. Both quantitative sensors and binary on/off type sensors can gather this data. In another example, the system 1000 can record a sequence of compressive forces incurred by the footwear, which can be used for purposes such as determining foot pronation or supination, weight transfer, foot strike patterns, or other such applications. In another embodiment the sensor(s) can quantitatively measure compressive forces on different portions of the footwear (e.g., using the array of magnets 1250-1252 discussed below) and the measured information can include quantitative compressive force and/or impact information. Relative differences in the forces on different portions of the footwear can be used, for example, to determine a wearer's weight distribution, or "center of pressure". The weight distribution and/or center of pressure can be calculated independently for one or both articles of footwear used by a wearer, or can be calculated over both shoes together, such as to find a center of pressure or center of weight distribution for a wearer's entire body. In an example, the sensor(s) can measure rates of change in compressive forces (see, e.g., FIGS. 12E and 12F), contact time, flight time or time between impacts (such as for jumping or running), and/or other temporally-dependent parameters. It is understood that, in any embodiment, the sensors can use or require a specified threshold force or impact before registering a given force/impact as an event.

Figure 10B:
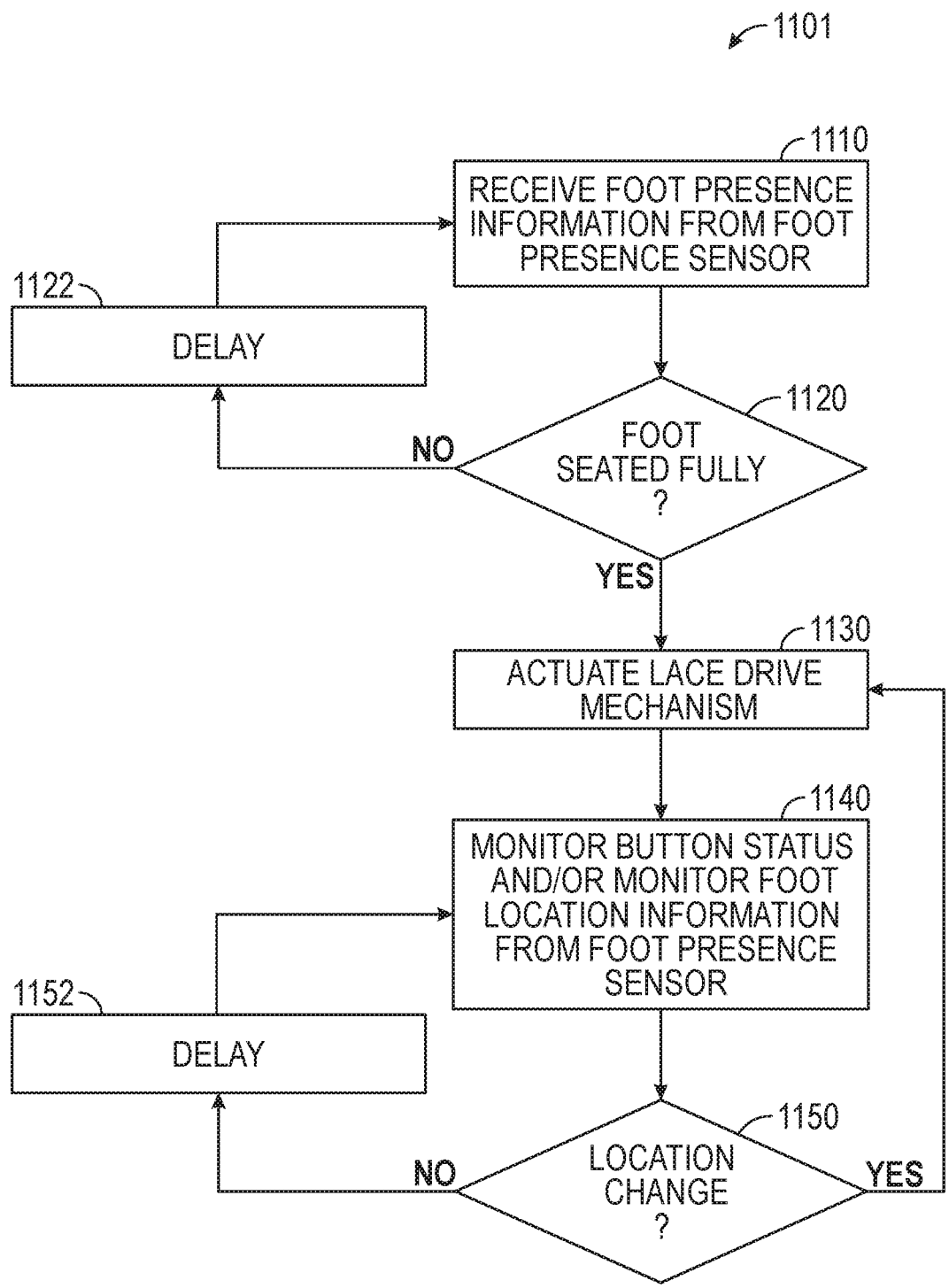
FIG. 10B is a flowchart illustrating an example of using foot presence information from a sensor.

FIG. 10B illustrates a flowchart showing an example of a method 1100 that includes using foot presence information from a footwear sensor. At operation 1110, the example includes receiving foot presence information from the foot presence sensor 1010. The foot presence information can include binary information about whether or not a foot is present in footwear, or can include an indication of a likelihood that a foot is present in a footwear article. The information can include an electrical signal provided from the foot presence sensor 1010 to the processor circuit 1050. In an example, the foot presence information includes qualitative information about a location of a foot relative to one or more sensors in the footwear.

At operation 1120, the example includes determining whether a foot is fully seated in the footwear. If the sensor signal indicates that the foot is fully seated, then the example can continue at operation 1130 with actuating the drive mechanism 1040. For example, when a foot is determined to be fully seated at operation 1120, such as based on information from the foot presence sensor 1010, the drive mechanism 1040 can be engaged to tighten footwear laces via the spool 1031, as described above. If the sensor signal indicates that the foot is not fully seated, then the example can continue at operation 1122 by delaying or idling for some specified interval (e.g., 1-2 seconds, or more). After the specified delay elapses, the example can return to operation 1110, and the processor circuit 1050 can re-sample information from the foot presence sensor 1010 to determine again whether the foot is fully seated.

After the drive mechanism 1040 is actuated at operation 1130, the processor circuit 1050 can be configured to monitor foot location information at operation 1140. For example, the processor circuit can be configured to periodically or intermittently monitor information from the foot presence sensor 1010 about an absolute or relative position of a foot in the footwear. In an example, monitoring foot location information at operation 1140 and receiving foot presence information at operation 1110 can include receiving information from the same or different foot presence sensor 1010. For example, different electrodes can be used to monitor foot presence or position information at operations 1110 and 1140.

At operation 1140, the example includes monitoring information from one or more buttons associated with the footwear, such as the buttons 121. Based on information from the buttons 121, the drive mechanism 1040 can be instructed to disengage or loosen laces, such as when a user wishes to remove the footwear.

In an example, lace tension information can be additionally or alternatively monitored or used as feedback information for actuating the drive mechanism 1040, or for tensioning laces. For example, lace tension information can be monitored by measuring a drive current supplied to the motor 1041. The tension can be characterized at a point of manufacture or can be preset or adjusted by a user, and can be correlated to a monitored or measured drive current level.

At operation 1150, the example includes determining whether a foot location has changed in the footwear. If no change in foot location is detected by the foot presence sensor 1010 and the processor circuit 1050, then the example can continue with a delay at operation 1152. After a specified delay interval at operation 1152, the example can return to operation 1140 to re-sample information from the foot presence sensor 1010 to again determine whether a foot position has changed. The delay at operation 1152 can be in the range of several milliseconds to several seconds, and can optionally be specified by a user.

In an example, the delay at operation 1152 can be determined automatically by the processor circuit 1050, such as in response to determining a footwear use characteristic. For example, if the processor circuit 1050 determines that a wearer is engaged in strenuous activity (e.g., running, jumping, etc.), then the processor circuit 1050 can decrease a delay duration provided at operation 1152. If the processor circuit determines that the wearer is engaged in non-strenuous activity (e.g., walking or sitting), then the processor circuit can increase the delay duration provided at operation 1152. By increasing a delay duration, battery life can be preserved by deferring sensor sampling events and corresponding consumption of power by the processor circuit 1050 and/or by the foot presence sensor 1010. In an example, if a location change is detected at operation 1150, then the example can continue by returning to operation 1130, for example, to actuate the drive mechanism 1040 to tighten or loosen the footwear about the foot. In an example, the processor circuit 1050 includes or incorporates a hysteretic controller for the drive mechanism 1040 to help avoid unwanted lace spooling in the event of, e.g., minor detected changes in foot position.

Figure 11A:
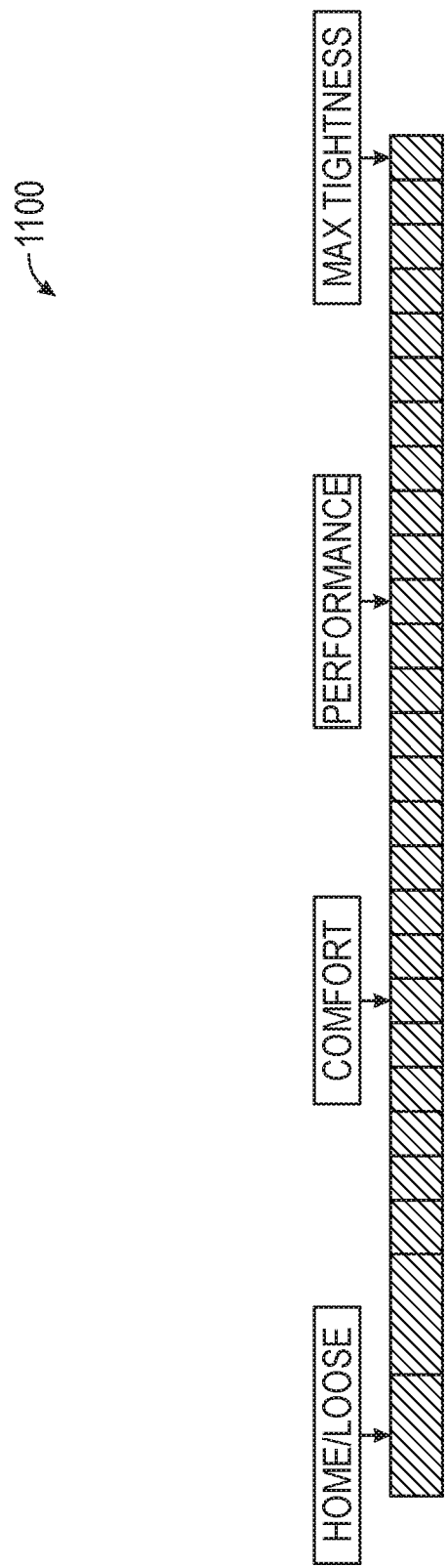
FIG. 11A-11D are diagrams illustrating a motor control scheme for a motorized lacing engine, according to some example embodiments.

FIGS. 11A-11D are diagrams illustrating a motor control scheme for a motorized lacing engine, according to some example embodiments. In an example, the motor control scheme involves dividing up a total travel, in terms of lace take-up, into segments, with the segments varying in size based on position on a continuum of lace travel (e.g., between home/loose position on one end and max tightness on the other). As the motor is controlling a radial spool and will be controlled, primarily, via a radial encoder on the motor shaft, the segments can be sized in terms of degrees of spool travel (which can also be viewed in terms of encoder counts). On the loose side of the continuum, the segments can be larger, such as 10 degrees of spool travel, as the amount of lace movement is less critical. However, as the laces are tightened each increment of lace travel becomes more and more critical to obtain the desired amount of lace tightness. Other parameters, such as motor current, can be used as secondary measures of lace tightness or continuum position. FIG. 11A includes an illustration of different segment sizes based on position along a tightness continuum.

In FIG. 11A, a total lace travel can be divided into a fixed number of segments. A segment can be an amount of spool travel, and can be fixed or variable. For example, a segment length can depend on where the lacing engine is on the scale in terms of lace take-up. The example of FIG. 11A includes a graphical representation of a total lace travel 1100 divided into multiple, serially-arranged segments. For example, one or more segments can correspond to about 10 degrees of rotational spool travel, such as when the lacing engine or footwear is at a first or loose end of a tightness scale. At an opposite second or tight end of the scale, a segment can correspond to about 2 degrees of rotational spool travel. Other values can similarly be used. In an example, a rotational position of the spool can be a primary input for a tightness setting, and a motor current can be used secondarily or as a safety check.

Figures 11B, 11C:
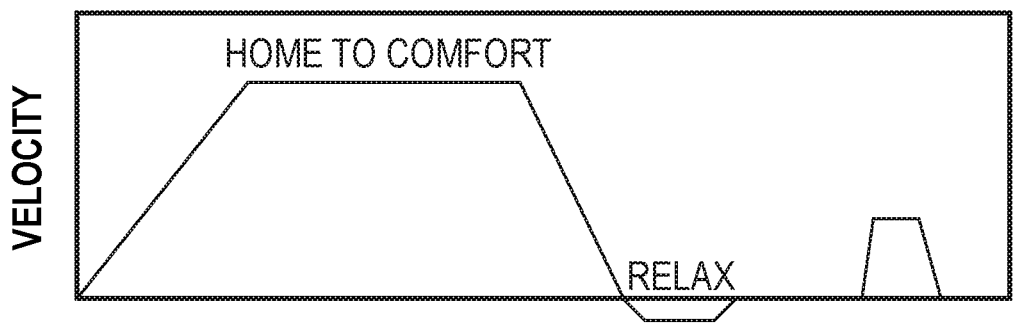

FIG. 11B illustrates using a tightness continuum position to build a table of motion profiles based on current tightness continuum position and desired end position. The motion profiles can be translated into specific inputs, such as from user input buttons or gesture information received from various sensors. The motion profile can include parameters of spool motion, such as acceleration (Accel (deg/s/s)), velocity (Vel (deg/s)), deceleration (Dec (deg/s/s)), and angle of movement (Angle (deg)).

FIG. 11B includes an example of a first table 1101 of spool motion or location characteristics. A motion profile can be any combination of one or more moves or location characteristics. In an example, an autolace event, a button press, a gesture-based input, or other input can initiate or trigger a motion profile. In an example, a processor circuit receives the trigger input and then updates a motor current supply to support the motion requested defined by the input. Multipliers or factors for a gear reduction can be provided, such as can be used for quickly updating or changing one or more entries in the first table 1101. The first table 1101 is an example only and the values shown can change, for example, based on user settings, preferences, or default settings.

FIG. 11C depicts an example motion profile chart 1103, The chart 1103 includes an x-axis representing time and a y-axis representing velocity. The velocity axis corresponds to a lace or spool travel velocity. In the example of FIG. 11C, a "Home to Comfort" motion profile can be used to spool and unspool a lace, followed by a "Relax" motion profile.

Figure 11D:
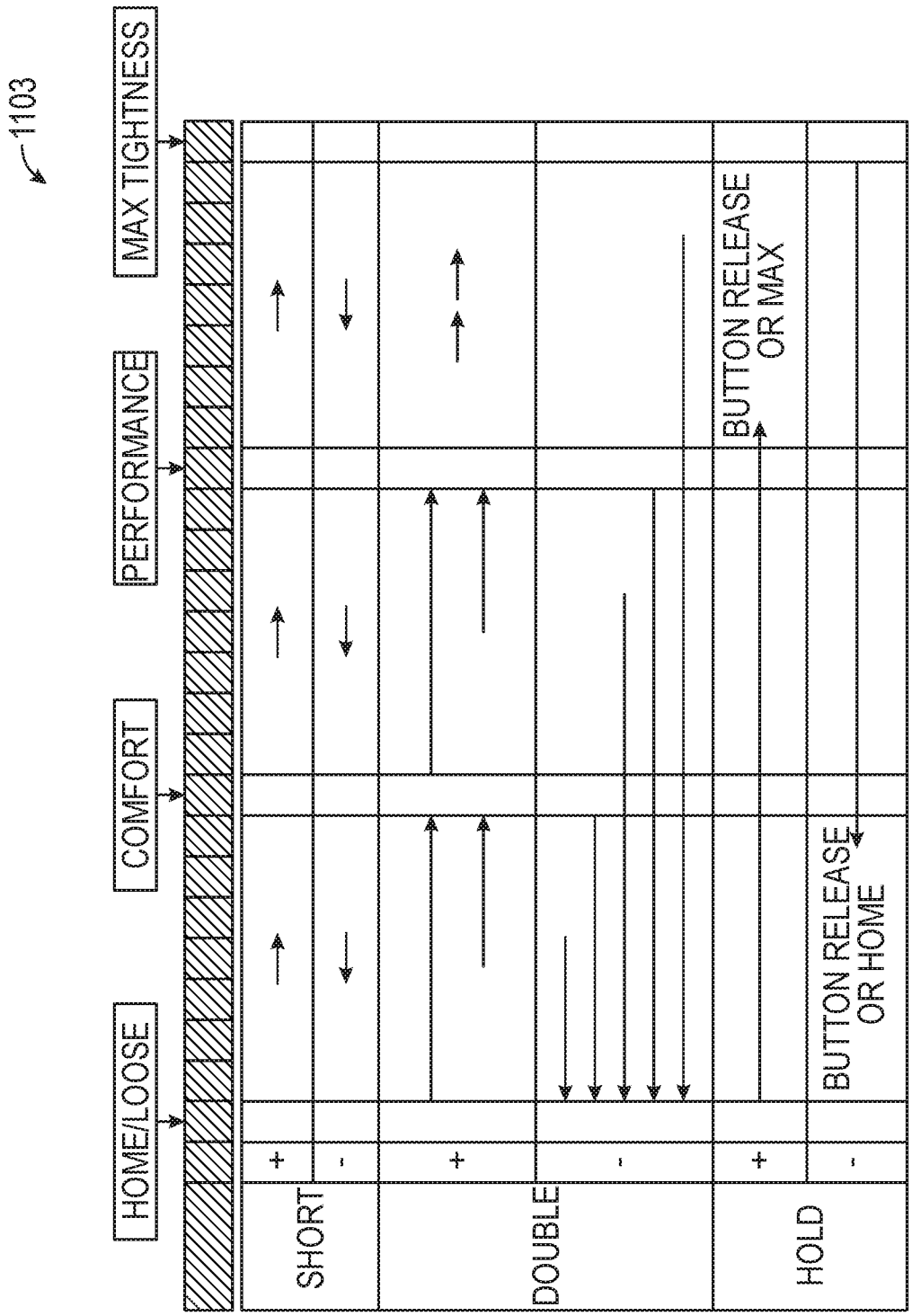

FIG. 11D illustrates generally a second table 1103 that includes an example of various user inputs that can activate various motion profiles along a footwear tightness continuum. In an example, footwear or a lacing engine can include or use various factory default settings for baseline comfort and performance. However, in response to a user input, such as a button push, the lacing engine can be caused to perform one or more different profile or movement changes. For example, in response to a "Short" press, the lacing engine can be caused to move incrementally among the various segments. In response to a "Double" press, the lacing engine can be caused to move between adjacent pre-defined or specified motion profiles. In response to a button "Hold" (e.g., a hold greater than about 250 ms), the lacing engine can be caused to move between fully tightened or fully relaxed profiles. In an example, any user input to the button or other input can stop the lacing engine.

Figure 12A:
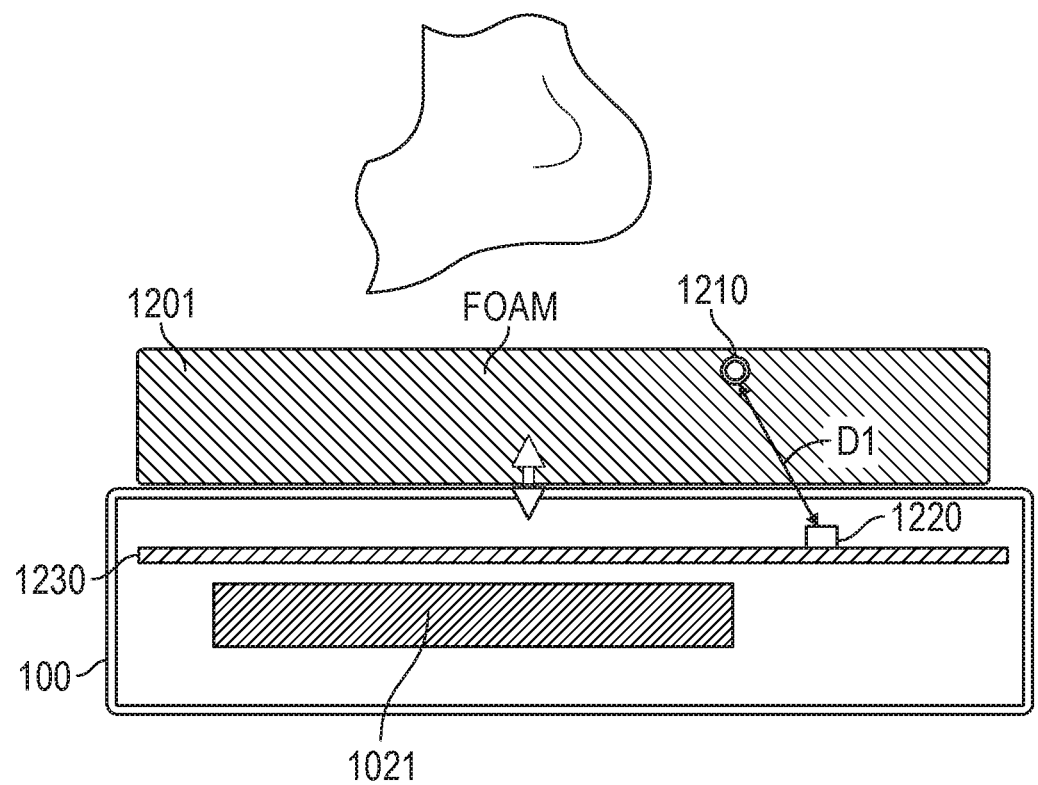
FIGS. 12A-12D are block diagrams illustrating magnet-based foot presence sensor configurations.

FIG. 12A is a block diagram illustrating footwear components that can include a magnetic foot presence sensor. The example in FIG. 12A includes a magnetometer 1220 and a first magnet 1210 that is spaced apart from the magnetometer 1220. Although generally referred to herein as a "magnet", various materials or components can be used and sensed by the magnetometer 1220. In an example, the first magnet 1210 itself isn't sensed by the magnetometer 1220, and instead an influence of the first magnet 1210 on a magnetic field at or near the magnetometer 1220 is sensed by the magnetometer 1220. Thus references herein to the first magnet 1210 (or to other magnets or magnetic bodies) can be understood to include other materials, or an effect of the first magnet 1210 or other materials, that are detectable by the magnetometer 1220.

The magnetometer 1220 can be surface mounted or otherwise coupled to a main PC assembly 1230, and the PC assembly 1230 can be included in the housing structure 100. In the example, the first magnet 1210 is positioned laterally offset from a vertical axis of the magnetometer 1220. For example, the first magnet 1210 can be disposed in a foam insole 1201, and the foam insole 1201 can be configured to be used or won adjacent the housing structure 100, such as inside a footwear article.

In an example, the magnetometer 1220 includes an ST Microelectronics LSM303AGR (e.g., a combination accelerometer and magnetometer) or similar device. In an example, under normal use conditions, foot pressure from a foot displaces the magnet 1210 (e.g., within the foam insole 1201) by about 0.5-1 mm. In an example, the foam insole 1201 can be included in a recess above the housing structure 100 or can be included as part of another insole. Other examples can include using a bridge to hold the magnet 1210, as further discussed below. A bridge can help to increase an area onto which an applied pressure or force (e.g., from a foot) displaces the magnet 1210. The foam insole 1201 can be selectively coupled or responsive to the applied pressure by, e.g., placing a film on top of the foam insole 1201 and magnet. The film can vary in stiffness, shape, and/or area, for example, depending on which region underfoot is targeted. That is, a single or unitary film can have different regions corresponding to different foot regions to thereby adjust a sensitivity of the sensor system.

The magnet 1210 and the magnetometer 1220 need not be located such that the magnet 1210 is positioned vertically above the magnetometer 1220. In an example, the magnet 1210 can be offset to one side or the other of the magnetometer 1220, such as illustrated in the example of FIG. 12A.

Although labeled in the example of FIG. 12A as "foam", the compressible layer of the foam insole 1201 can be any compressible material such as foam, rubber, silicone, cloth, or a polymer-based material or other material. In an example, the compressible layer is about 3 to 10 mm thick.

In an example, the lacing engine 10 includes the housing structure 100, and the magnetometer 1220 is included inside of or atop the housing structure 100. In an example, the housing structure is a polycarbonate structure having a wall thickness of about 1 mm. In other examples, the housing structure can be made of aluminum, steel, or other non-conducting materials including glass, porcelain, rubber, or various polymers or plastics.

Figure 12B:
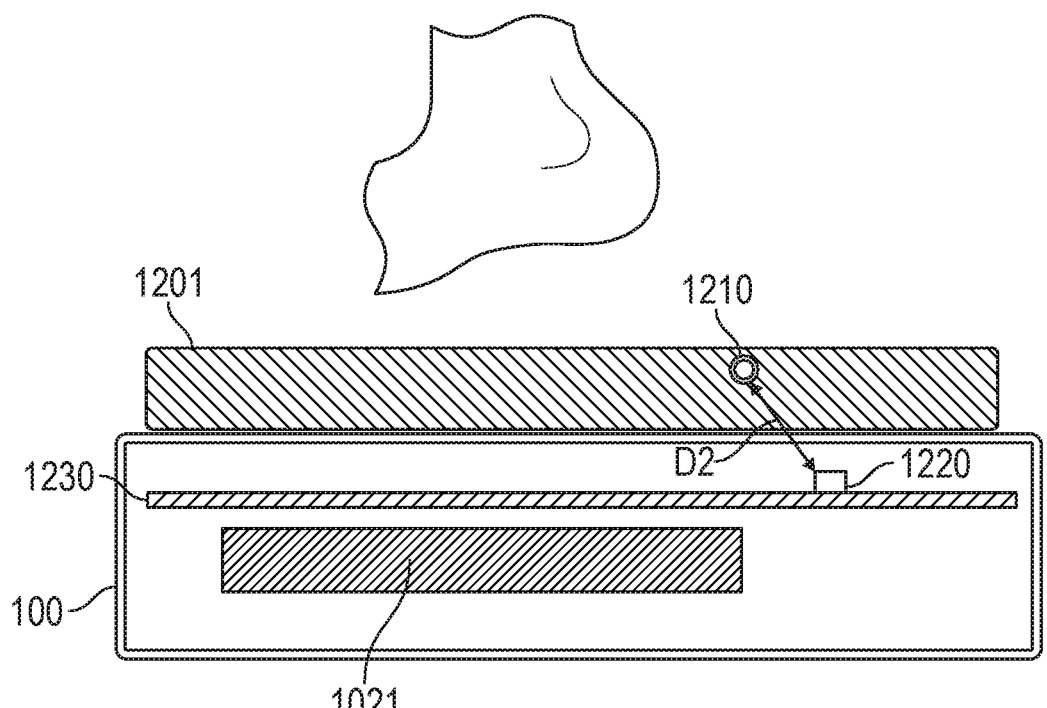

FIG. 12A shows the insole 1201 in a first compression state such that the magnet 1210 and magnetometer 1220 are separated by a first distance D1. FIG. 12B shows the insole 1201 in a second, more-compressed state such that the magnet 1210 and magnetometer 1220 are separated by a lesser second distance D2. In an example, the magnetometer 1220 provides the distance information to the processor circuit 1020, and the processor circuit 1020 is configured to identify or use information about the distances or about a rate of change between consecutive distance information. For example, the processor circuit 1020 can be configured to determine a foot impact characteristic, such as an impact force, or impact timing or frequency, based on the distance information.

Figure 12C:
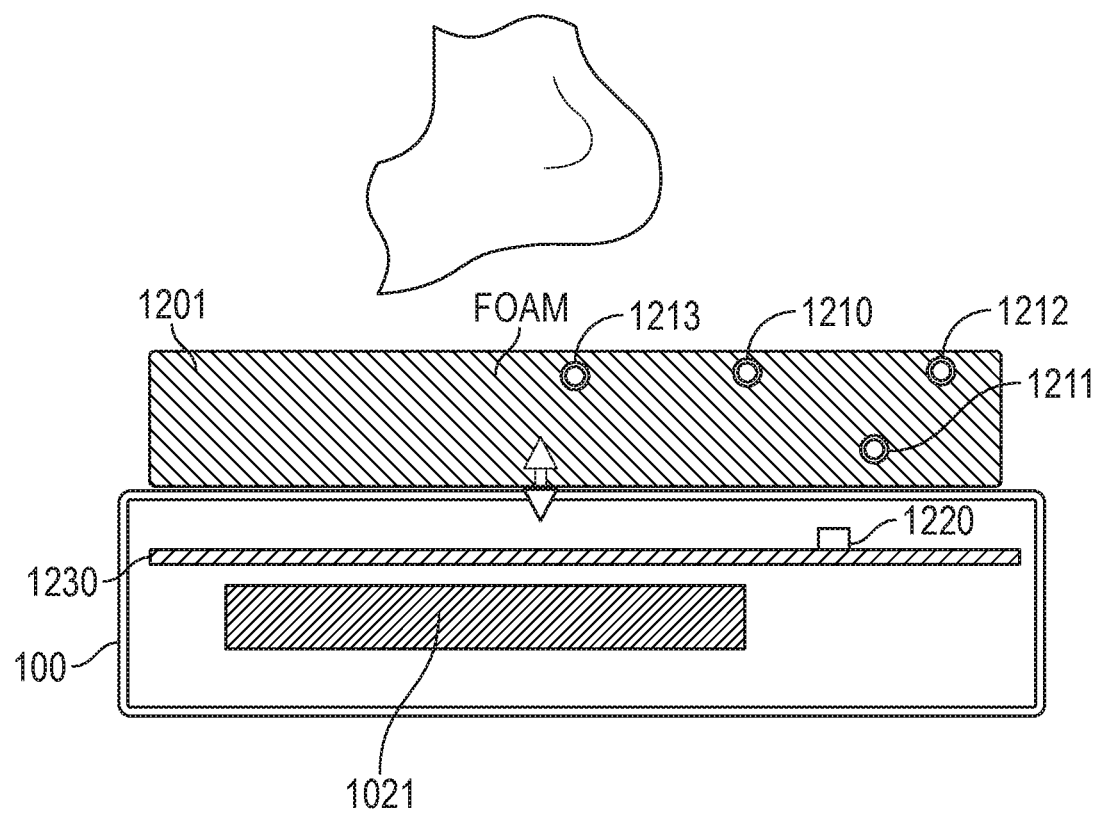

Although FIGS. 12A and 12B illustrate generally a single magnet and single magnetometer configuration, other configurations can be used. For example, multiple magnets can be used with a single magnetometer. FIG. 12C is a block diagram illustrating footwear components that can include a magnetic foot presence sensor with the magnetometer 1220 and multiple magnets 1210-1213 (or other discrete materials that can be sensed by the magnetometer 1220). In an example, the multiple magnets 1210-1213 can be positioned in different places in a footwear article. For example, an array of magnets can be disposed within an insole, such as at different vertical heights over or near the magnetometer 1220, and/or at different lateral spacing relative to the magnetometer 1220. In the example of FIG. 12C, a first magnet 1210 is offset by a first height and lateral displacement relative to the magnetometer 1220, and a second magnet 1211 is offset by a lesser second height and lesser lateral displacement relative to the magnetometer 1210. Alternatively or additionally, multiple magnetometers can be used to sense information about displacement of one or more different magnets.

Figure 12D:
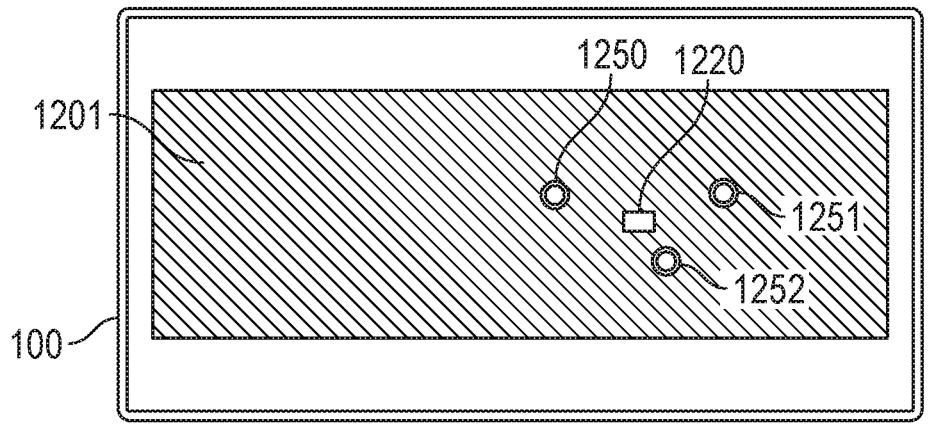

FIG. 12D is a block diagram illustrating a top view of footwear components that includes a magnetic foot presence sensor with the magnetometer 1220. In this example, an array of magnets 1250-1252 (or other discrete materials that can be sensed by the magnetometer 1220) is shown as being laterally offset (i.e., in x and y directions) from a vertical axis (i.e., z direction, into the page) of the magnetometer 1220. In this example, information from the magnetometer 1220 can be used to monitor foot presence, and to monitor information about foot shear, that is, information about a lateral shift in a position of the foot. For example, a foot on the insole 1201 can cause the insole to move or deflect forward, backward, or to a side. The array of magnets 1250-1252, such as can be coupled to or disposed within the insole 1201, can move relative to the magnetometer 1220. Resulting signals from the magnetometer 1220 can indicate a degree or magnitude of shear or later foot movement.

In an example, an article of footwear (see, e.g., FIG. 1) can include a ferromagnetic body disposed in the article, such as the magnet 1210 or the array of magnets 1250-1252. The article can include the magnetometer 1220 provided or arranged within the article to measure a strength or direction of a magnetic field that is influenced by a position of the ferromagnetic body. In an example, one of the ferromagnetic body and the magnetometer is configured to move relative to the other one of the ferromagnetic body and the magnetometer, such as according to movement of a foot in the article or according to movement of the article itself. For example, when the ferromagnetic body is disposed in the insole 1201, the ferromagnetic body can move according to compression or relaxation of the insole 1201 when the article is used for walking, running, or other activities.

In an example, the magnetometer 1220 is coupled to the processor circuit 1020. The processor circuit 1020 can receive a signal from the magnetometer that corresponds to a sensed magnetic field strength. In an example, the signal includes information about a change or rate of change of the sensed magnetic field. For example, the signal can include information about a changing location of, or series of locations of, the ferromagnetic body relative to the magnetometer 1220.

Figure 12E:
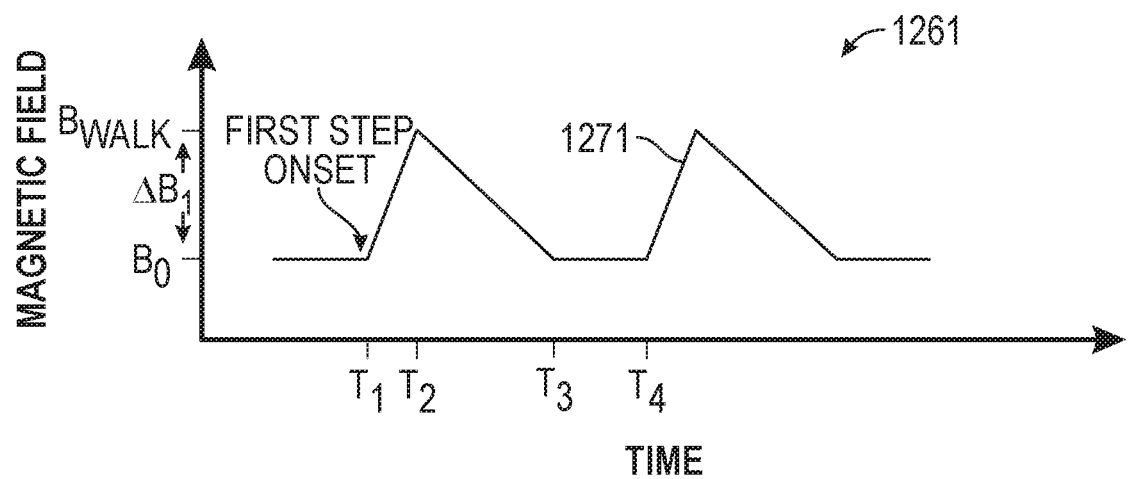
FIGS. 12E and 12F illustrate charts showing time-varying information from a magnetometer.
Figure 12F:
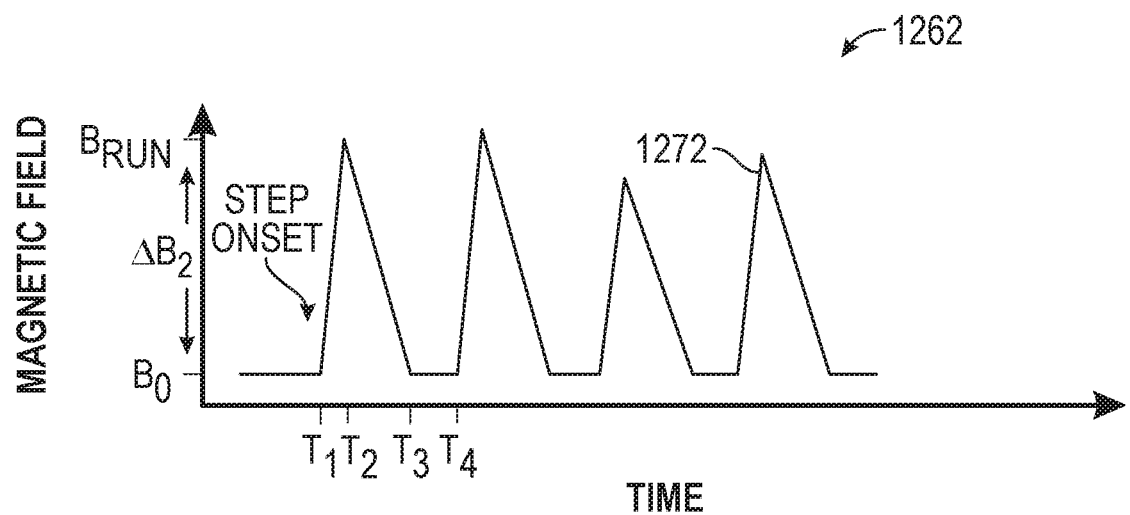

FIGS. 12E and 12F illustrate charts showing time-varying information from a magnetometer. FIG. 12E shows a first magnetic field chart 1261 with a first time-varying magnetic field signal 1271. In an example, the first time-varying magnetic field signal 1271 can be generated by the magnetometer 1220, and the signal is based on sensed information about a location of the magnet 1210 relative to the magnetometer 1220, such as in a first footwear article. That is, the first time-varying magnetic field signal 1271 can represent magnetic field strength information over time.

In the example of FIG. 12E, the first time-varying magnetic field signal 1271 has a baseline or reference magnetic field strength $B_0$. The reference magnetic field strength $B_0$ can correspond to a reference position of the footwear article that includes the magnetometer 1220 and the magnet 1210. In an example, the reference magnetic field strength $B_0$ corresponds to empty or unused footwear, or corresponds to footwear that is in a relaxed or uncompressed state (e.g., a wearer is sitting or otherwise exerting minimal force on the insole 1201). In an example, the reference magnetic field strength $B_0$ corresponds to a stationary footwear condition, such as when a wearer is standing substantially still and the magnet 1210 is biased toward the magnetometer 1220 by a substantially constant bias force.

The example of FIG. 12E illustrates several changes in the first time-varying magnetic field signal 1271 over the interval shown. In an example, the several changes correspond to foot strike events or steps. A first time $T_1$ can correspond to an onset of a first step. That is, at the first time $T_1$ a wearer of the article can begin to apply pressure or force to the insole 1201 of a first footwear article that includes that magnet 1210. At a second time $T_2$, the first step can be completed and the wearer's weight can rest substantially on the one foot that corresponds to the first footwear article. At the second time $T_2$, the insole 1201 can be compressed and the magnet 1210 can be moved into a more proximal position with respect to the magnetometer 1220. As a result, the magnetometer 1220 can detect a greater magnetic field strength $B_{WALK}$ than was detected in the reference position, $B_0$.

An interval from the second time $T_2$ to a third time $T_3$ can represent a wearer progressing through a walking motion and releasing pressure or compressive force from the first foot. Thus at least a portion of a first step event can be represented by the interval between the first and third times $T_1$ and $T_3$. At time $T_3$, the magnet 1210 in the first footwear article is returned to its baseline or reference position, and the magnetometer 1220 again senses the reference magnetic field strength $B_0$.

Various information about the first step event can be determined from the first time-varying magnetic field signal 1271. In an example, a signal magnitude change (e.g., $\Delta B_1$ in FIG. 12E) can represent a foot impact force for the first step event. That is, quantitative information about the foot's impact can correspond to displacement of the magnet 1210 relative to the magnetometer 1220. A greater signal magnitude change can correspond to a greater foot impact force, for example, because the insole 1201 can be further compressed under a greater foot impact force than under a lesser force.

Information about a duration between various magnetic field signal magnitude changes can be used to provide information about a foot impact. For example, a duration between the first and second times $T_1$ and $T_2$ can indicate how rapidly the insole 1201, and therefore the foot, goes from a relaxed state to a compressed state and can, in an example, correspond to how quickly a user is moving (walking, jogging, running, etc.). Thus, in an example, the duration information can be used to assess or provide information about a physiologic effect of the wearer's own activity or gait.

In an example, an activity type can be classified based on the rate of change information, or based on signal morphology information, from the first time-varying magnetic field signal 1271. A magnetic field signal that represents a walking gait can have different time intervals between signal peaks and valleys as compared to a signal that represents a running gait. A signal that represent a jogging gait can be further distinguished, such as based on signal bounces or other slight changes in the signal. For example, a signal that corresponds to a jogging gait can have longer intervals with somewhat rounded peaks or valleys, and durations between different peak or valley events can drift moderately over time. A signal that corresponds to a running gait can have shorter intervals and sharp, well-defined peaks or valleys, and can include durations between different peak or valley events that are most consistent or static over time.

In the example of FIG. 12E, the rate of change or slope of the first time-varying magnetic field signal 1271 between the first and second times $T_1$ and $T_2$ differs from the rate of change or slope between the second and third times $T_2$ and $T_3$. In this example, the slope difference can represent a relatively quick step onset and a relatively slow or relaxed recoil or transition to another foot. In some examples, the magnetic field signal slopes can be relatively constant over different step events, and the slopes can be relatively constant for each foot. Rate of change information about different feet, or about a rate of change of various portions of the magnetic field signal, can be used to analyze a wearer's gait such as to determine if the wearer tends to "favor" one foot over the other, or to analyze recovery progression after an injury.

In an example, rate of change information or event information can be determined from a time-varying magnetic field signal and used to identify a series of foot strike events. The information can be used to provide a step counter or pedometer. In an example, the processor circuit 1020 can include or use information about a stride length, together with the foot strike information, to calculate distance information. In an example, different stride information can be selected by the processor circuit 1020, such as corresponding to different rate of change information in a foot strike for a particular foot strike event, to enhance accuracy of a distance determination.

FIG. 12F shows a second magnetic field chart 1262 with a second time-varying magnetic field signal 1272. In an example, the second time-varying magnetic field signal 1272 can be generated by the magnetometer 1220, and the signal is based on sensed information about a location of the magnet 1210 relative to the magnetometer 1220, such as in a first footwear article. That is, the second time-varying magnetic field signal 1272 can represent magnetic field strength information over time.

In the example of FIG. 12F, the second time-varying magnetic field signal 1272 has a baseline or reference magnetic field strength $B_0$. The baseline or reference field can be the same or different baseline or reference field as used in the example of FIG. 12E. In an example, the baseline or reference field can be user specific, and can be influenced by one or more environmental factors that contribute to a magnetic field strength detected by the magnetometer 1220. As similarly explained above, the reference magnetic field strength $B_0$ in the example of FIG. 12F can correspond to a reference position of the footwear article that includes the magnetometer 1220 and the magnet 1210.

The example of FIG. 12F illustrates several changes in the second time-varying magnetic field signal 1272 over the interval shown. In an example, the several changes correspond to foot strike events or steps for a running wearer. A first time $T_1$ can correspond to an onset of a first step in a running gait. That is, at the first time $T_1$ a wearer of the article can begin to apply pressure or force to the insole 1201 of a first footwear article that includes that magnet 1210. At a second time $T_2$, the first step in the running gait can be completed and the wearer's weight can rest substantially or entirely on the one foot that corresponds to the first footwear article. At the second time $T_2$, the insole 1201 can be compressed and the magnet 1210 can be moved into a more proximal position with respect to the magnetometer 1220. As a result, the magnetometer 1220 can detect a greater magnetic field strength $B_{RUN}$ than was detected in the reference position, $B_0$. Furthermore, since the running gait can represent a wearer traveling at a greater speed than walking, the detected magnetic field strength $B_{RUN}$ in the example of FIG. 12F can be greater than the detected magnetic field strength $B_{WALK}$ in the example of FIG. 12E (e.g., assuming the first and second time-varying magnetic field signals 1271 and 1272 correspond to the same wearer, or wearers of substantially the same weight).

An interval from the second time $T_2$ to a third time $T_3$ can represent a wearer progressing through a running motion on a first foot and releasing pressure or compressive force from the first foot. At time $T_3$, the magnet 1210 in the first footwear article is returned to its baseline or reference position, and the magnetometer 1220 again senses the reference magnetic field strength $B_0$.

Various information about discrete steps or strides in the running gait can be determined from the second time-varying magnetic field signal 1272. In an example, a signal magnitude change (e.g., $\Delta B_2$ in FIG. 12F) can represent a peak foot impact force for the illustrated strides. As shown in the example of FIG. 12F, different strides can have different peak values. A greater peak or greater signal magnitude change can correspond to a greater foot impact force, for example, because the insole 1201 can be further compressed under a greater foot impact force than under a lesser force.

Information about a duration between various magnetic field signal magnitude changes can be used to provide information about a foot impact. For example, a duration between the first and second times $T_1$ and $T_2$ can indicate how rapidly the insole 1201, and therefore the foot, goes from a relaxed state to a compressed state and can, in an example, correspond to how quickly the wearer is running.

Figure 12G:
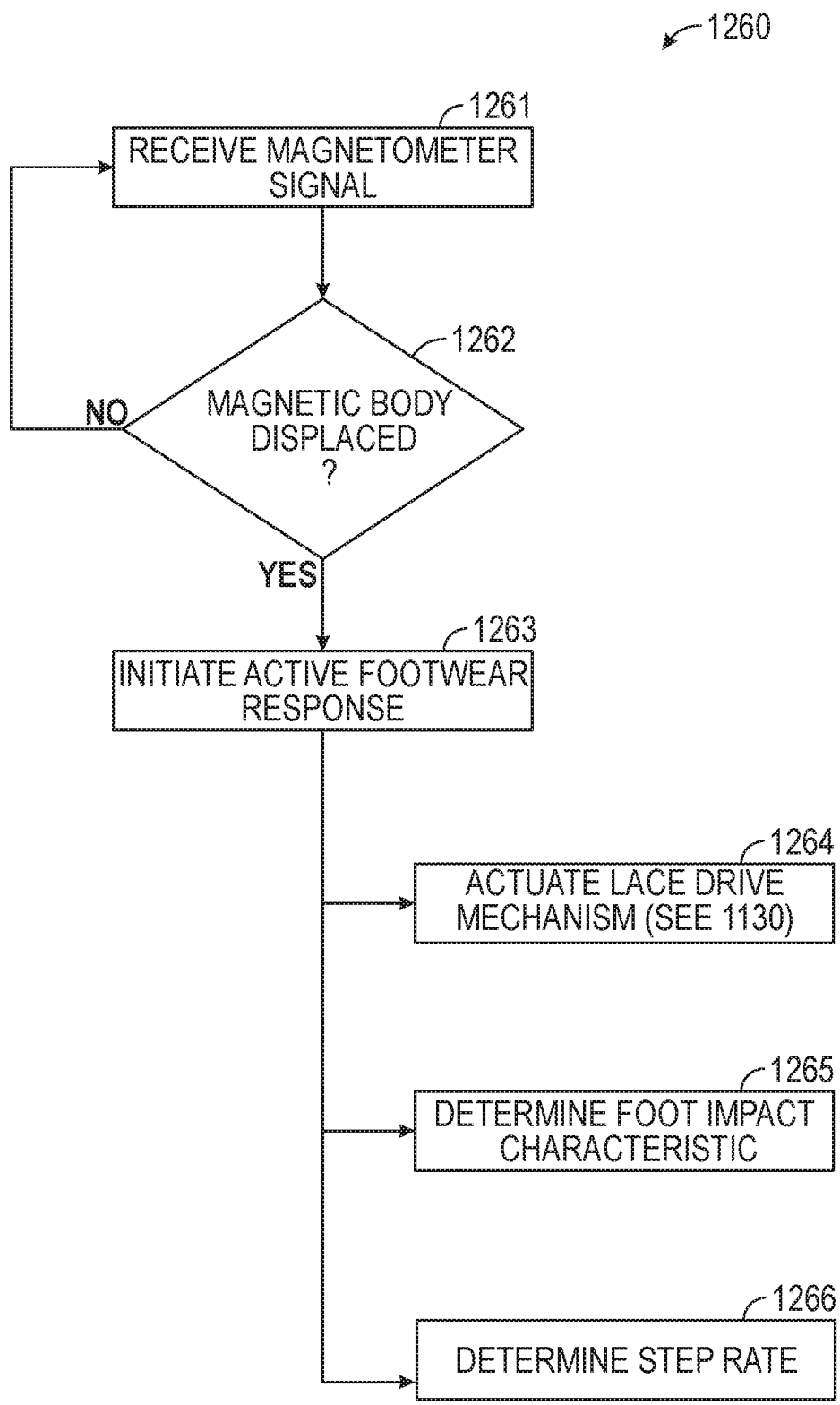
FIG. 12G illustrates generally an example of a method that includes initiating an active footwear response to a magnetometer signal.

FIG. 12G illustrates generally an example of a method 1260 that includes initiating an active footwear response to a magnetometer signal. The method 1260 can be performed at least in part by the processor circuit 1020 using information from the magnetometer 1220. At operation 1261, the method 1260 includes receiving a signal from the magnetometer 1220. The received signal can include an analog or digital, time-varying signal indicative of a time-varying magnetic field detected by the magnetometer 1220. The magnetic field can change, for example, based on a changing position of the magnet 1210 in footwear. In an example, the processor circuit 1020, or other dedicated circuit configured to carry out acts based on specified input conditions, can be configured to receive the magnetometer signal at operation 1261.

At operation 1262, the processor circuit 1020 can analyze the received signal and determine whether a magnetic body (e.g., the magnet 1210) was moved or displaced, such as by greater than a specified threshold movement amount. If no movement or insignificant (non-threshold) displacement is detected, then the method 1260 can return to operation 1261 to receive subsequent information from the magnetometer 1220. In an example, a fixed or variable delay can be provided between magnetometer signal sampling events. If, at operation 1262, the magnetic body is determined to have moved by greater than the specified threshold movement amount, then the example can continue at operation 1263 by initiating a response in the active footwear that includes the magnetometer 1220.

For example, at operation 1263, various footwear functions can be initiated, such as actuating a lace drive mechanism (operation 1264), determining a foot impact characteristic (operation 1265), or determining a step rate (operation 1266). At operation 1264, a lace drive mechanism can be actuated. For example, the lace drive mechanism can be actuated according to operation 1130 in the example of FIG. 10B. In an example, actuating the lace drive mechanism at operation 1264 includes monitoring foot impact or rate of change information from a time-varying magnetometer signal (e.g., received at operation 1261). The lace drive actuation at operation 1264 can include automatically adjusting a footwear tension about a foot in response to sensed foot impact information. For example, in response to information from the time-varying magnetometer signal that indicates a strenuous activity or severe use case, such as running or jumping, the lace drive mechanism can be actuated at operation 1264 to tighten the footwear about the foot. In contrast, if the time-varying information from the magnetometer 1220 indicates a wearer is stationary or walking slowly, then the lace drive mechanism can be actuated at operation 1264 to relax the footwear about the foot.

In an example, actuating the lace drive mechanism at operation 1264 includes tensioning the footwear about the foot when the footwear is first donned by the wearer. The magnetometer signal received at operation 1261 can indicate that the wearer is just starting to move or begin a step with the footwear, and in response the drive mechanism can be actuated to quickly tension the footwear to a first tension level. The tension level can be automatically adjusted by the processor circuit 1020, such as after gait information is received over the first couple of step events.

At operation 1265, the example of FIG. 12G includes determining a foot impact characteristic based on the received magnetometer signal. As discussed above in the examples of FIGS. 12E and 12F, a foot impact characteristic can include a rate of change in a compressive force that is applied to the footwear (and is thereby incurred or experienced by the foot inside the footwear). The foot impact characteristic can include information about a contact time, flight time, or time between impacts such as during running, walking, jumping, or other activities.

In an example, information about the foot impact characteristic can be used to provide a wearer with information about how hard his or her feet (individually) strike or impact a receiving surface. Information about the foot impact characteristic can further include information about whether the wearer is moving with a proper or desired foot placement. Such foot placement information can be discerned using a multi-axis magnetometer, or using the array of magnets 1250-1252. In an example, information about the foot impact characteristic can be recorded over time and used to provide information about a status of one or more components of the footwear. For example, the processor circuit 1020 can use information about foot impact characteristics over time to determine when the insole 1201 requires replacement.

At operation 1266, the example of FIG. 12G includes determining a step rate using the received magnetometer signal. As discussed above in the examples of FIGS. 12E and 12F, a step rate can correspond to changes identified in the time-varying magnetic field signals sensed by the magnetometer 1220. For example, magnetic field changes indicating an increase and subsequent decrease in field strength, such as within a specified duration, can be used to indicate a step event, or a likelihood that a step event occurred.

FIG. 12G illustrates several available responses to identified changes in a magnetic field signal sensed by the magnetometer 1220. Other responses can similarly be initiated such as including other responsive actions taken by circuitry or devices in the footwear or by other devices or processes that are in data communication with the footwear. For example, in response to an identified field change, data can be collected from one or more sensors in the footwear, such as from the motion sensor 1024 or environment sensor 1050. In an example, a profile or morphology of a time-varying magnetic field signal can be analyzed by the processor circuit 1020 and gesture information can be identified and used to trigger one or more other footwear functions, processes, or data transfer events.

Figure 13:
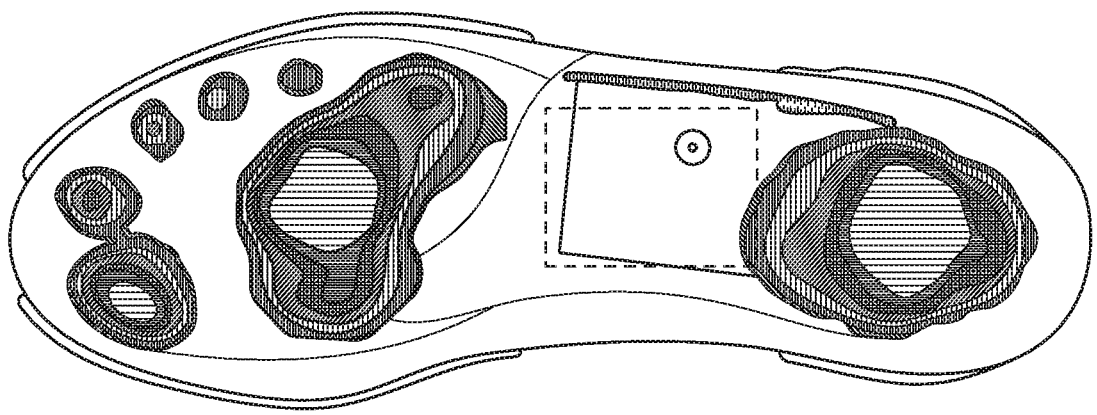
FIG. 13 is a diagram illustrating pressure distribution data for a nominal or average foot (left) and for a high arch foot (right) in a footwear article when a user of the article is standing.
Figure 13:
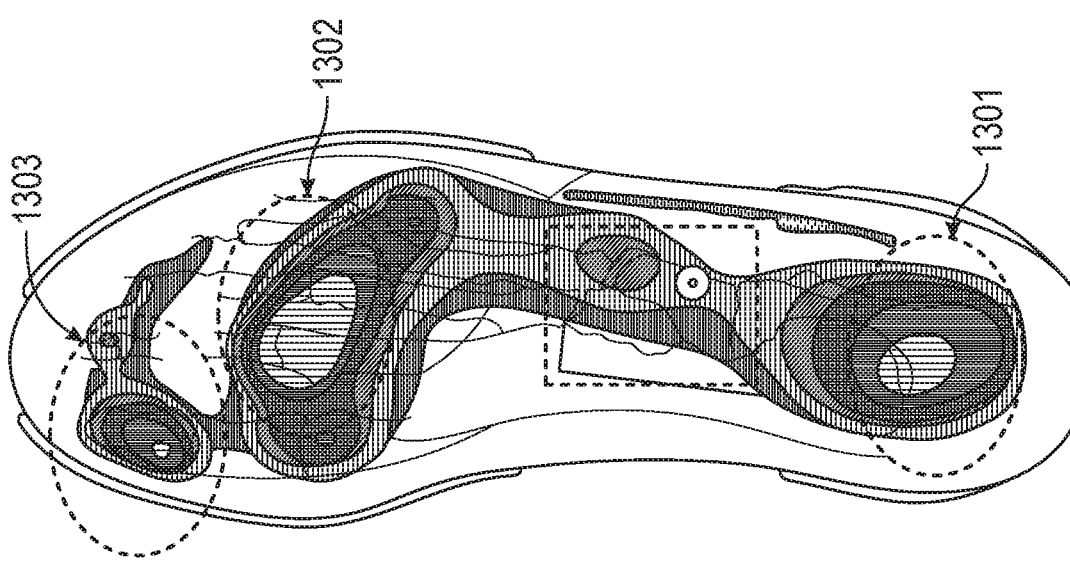

FIG. 13 is a diagram illustrating generally pressure distribution data for a nominal or average foot (left) and for a high arch foot (right) in a footwear article when a user of the article is standing. In this example, it can be seen that the relatively greater areas of pressure underfoot include at a heel region 1301, at a ball region 1302 (e.g., between the arch and toes), and at a hallux region 1303 (e.g., a "big toe" region). As discussed above, however, it can be advantageous to include various active components (e.g., including a foot presence sensor) in a centralized region, such as at or near a footwear arch region. For example, in this region, the housing structure 100 can be generally less noticeable or intrusive to a user when a footwear article that includes the housing structure 100 is worn.

In an example, a magnetometer such as the magnetometer 1220 in the examples of FIGS. 12A-12D can be included in or on the housing structure 100, and can be disposed in an arch area of a footwear article. One or more magnets located in the insole 1201 can be positioned proximal to the magnetometer 1220 as described above, such as also in the arch area of the article. However, because the arch area is generally not subjected to significant pressure or force changes (see, e.g., FIG. 13), a bridge component can optionally be used to transmit a force from another foot region to the magnet(s) and/or to the magnetometer 1220, for example to influence or enhance displacement of the magnet(s) relative to the magnetometer 1220.

Figure 14A:
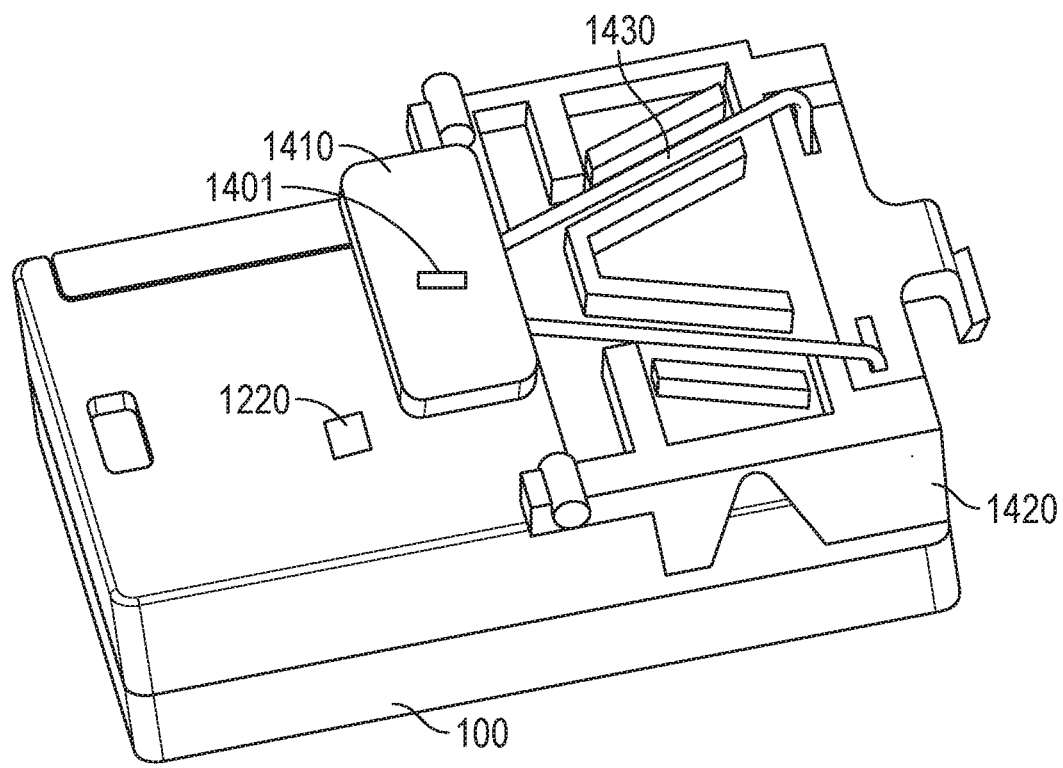
FIGS. 14A and 14B illustrate diagrams showing a bridge component or pressure plate for use with a magnetic sensor.
Figure 14B:
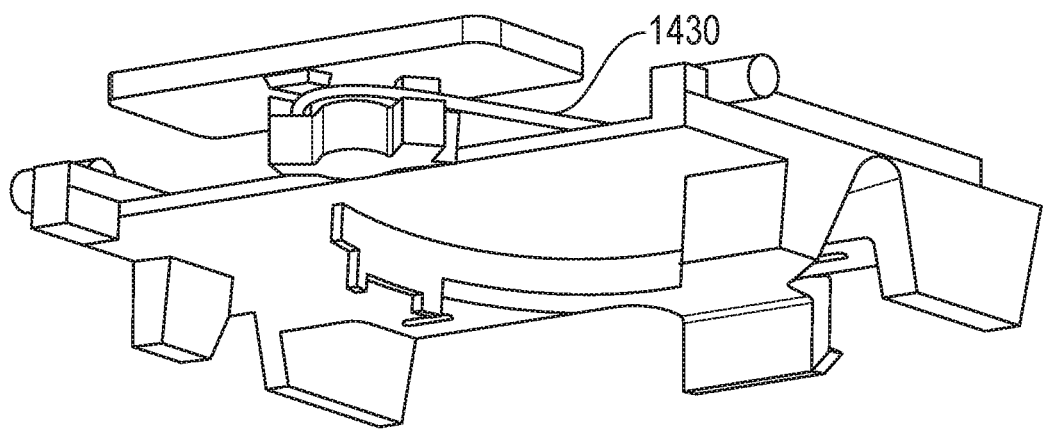

FIGS. 14A and 14B illustrate generally diagrams showing a bridge component or pressure plate for use with a magnetic sensor. FIG. 14A illustrates a first magnet 1401 disposed on a bridge component 1410. The bridge component 1410 can be coupled to a lid 1420 of the housing structure 100 by way of a spring wire 1430. The spring wire 1430 can be configured to push or bias the bridge component 1410, and thereby move the first magnet 1401, into a first position, such as when the first magnet 1401 is not subjected to the presence of a foot or when no pressure is applied to the footwear article that comprises the sensor. That is, the spring wire 1430 can act as a cantilever that projects from the lid 1420 and retains the first magnet 1401 at or near an edge of the cantilever. When a force or foot pressure is applied to the bridge component 1410, the bridge component 1410 can be deflected or moved relative to the housing structure 100 and relative to the magnetometer 1220 included within the housing structure 100. In an example, the housing structure 100 and/or another component of the footwear, such as the midsole 60, includes a recess, cavity, or compressible component that is configured to receive at least a portion of the bridge component 1410, such as to provide a travel path for the bridge component 1410 and the first magnet 1401 when a force or foot pressure is applied thereto.

The bridge component 1410 can have various shapes, contours, or orientations. For example, the bridge component 1410 can have an elongate shape that is oriented parallel or orthogonal to a heel-to-toe axis of a footwear article. In an example, the elongate shape can be configured to receive foot displacement information from the heel region 1301 and/or the hallux region 1303 of a foot (see FIG. 13). In an example, the elongate shape receives foot displacement information from an arch region by receiving displacement information from left and/or right sides of a foot.

In an example, the bridge component 1410 can be a replaceable element in an article of footwear. The bridge component 1410 can be selected from among multiple different bridge component types or styles according to a user's preference or anatomy. For example, a user with high arches can use a bridge component that is wider or longer than would be used by a user with low or shallow arches.

In an example, an article of footwear includes the bridge component 1410, and at least one of a ferromagnetic body, such as the magnet 1210, and the magnetometer 1220 is coupled to the bridge component 1410. The bridge component can be configured to bias the at least one of the magnet 1210 and the magnetometer 1220 away from the other one of the magnet 1210 and the magnetometer 1220 when the magnet 1210 and the magnetometer 1220 are in a relaxed state or reference position.

In an example, the bridge component 1410 is rigid or semi-rigid, such as made of an inflexible polymer or thin metal or ceramic. The bridge component can be configured to receive a foot displacement force from a foot from an arch region or other region of the foot and, in response, to correspondingly displace one of the magnet 1210 and the magnetometer 1220 (e.g., disposed on or coupled to the bridge component 1410) relative to its reference position.

FIGS. 15A-15C illustrate test data associated with magnet-based foot presence sensor configurations with a magnet pole oriented along an x-axis. FIGS. 15D-15F illustrate test data associated with magnet-based foot presence sensor configurations with a magnet pole oriented along a y-axis. FIGS. 15G-15I illustrate test data associated with magnet-based foot presence sensor configurations with a magnet pole oriented along a z-axis.

Figure 16A:
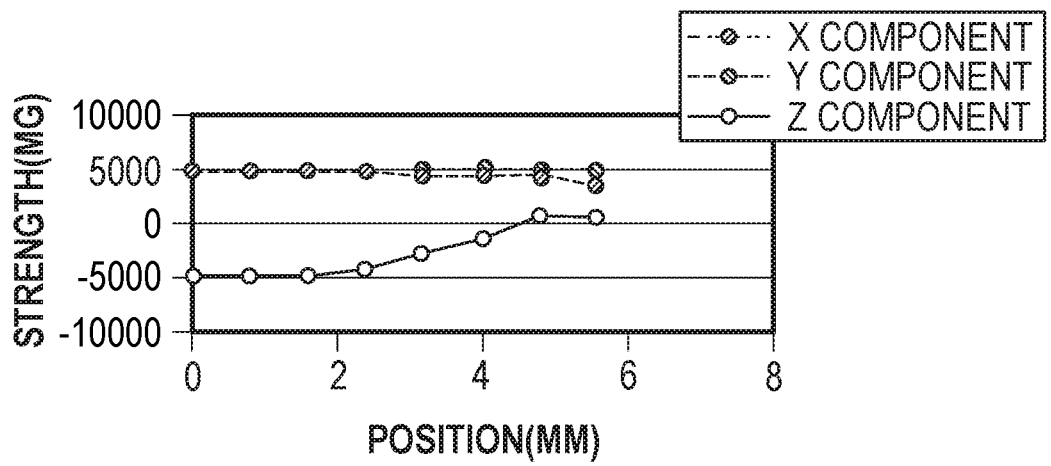
FIGS. 16A-16B illustrate magnetic field strength test data for a rectangular magnet.
Figure 16B:
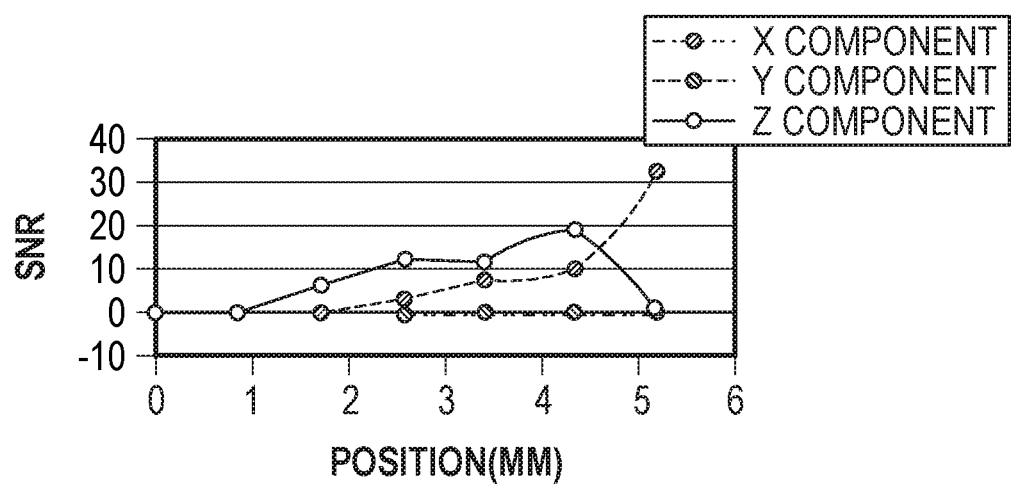
Figure 16C:
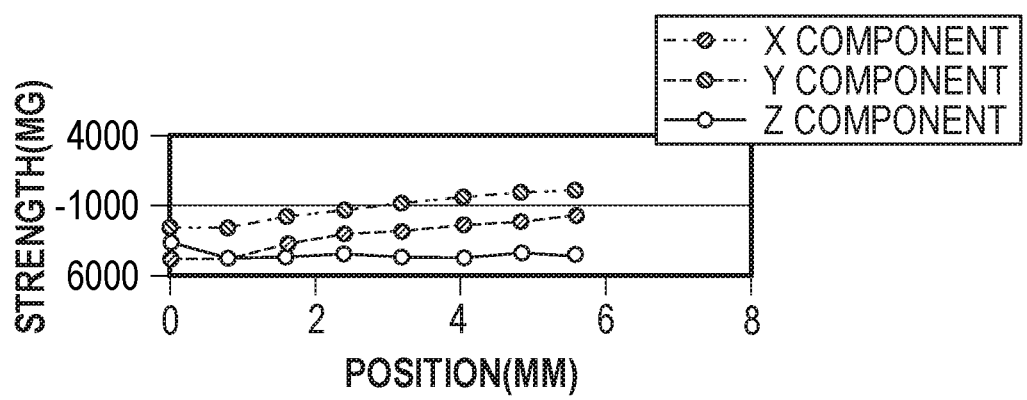
FIGS. 16C-16F illustrate magnetic field strength test data for a first circular magnet.
Figure 16D:
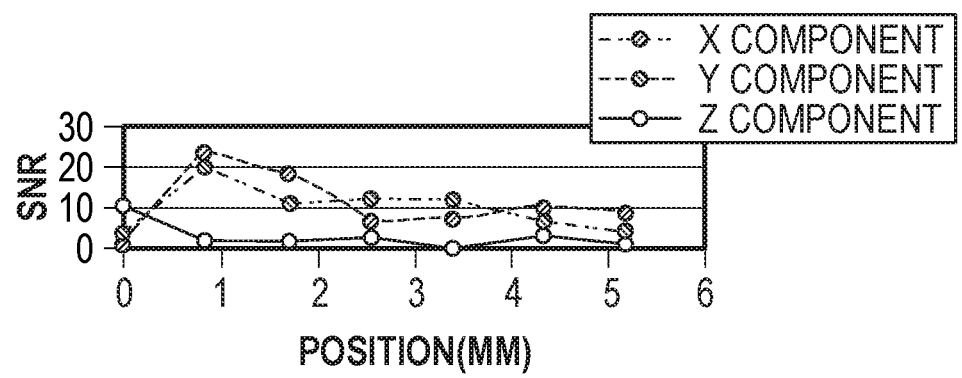
Figure 16E:
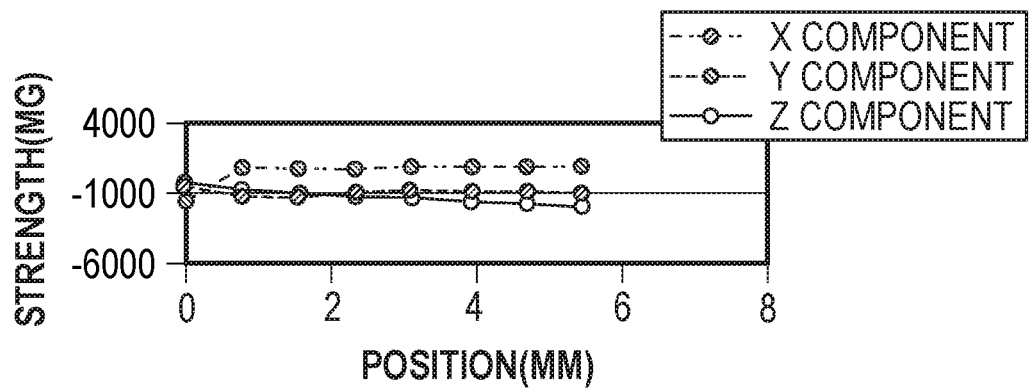
Figure 16F:
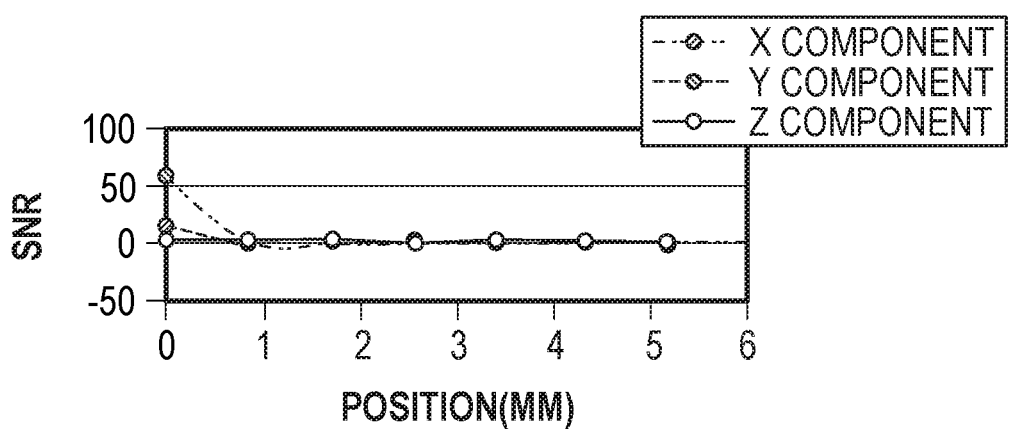
Figure 17A:
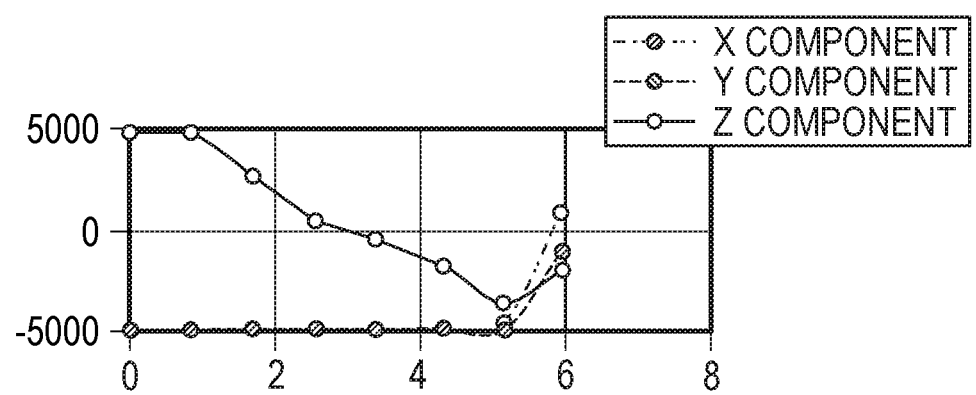
FIGS. 17A-17D illustrate magnetic field strength test data for a first circular magnet.
Figure 17B:
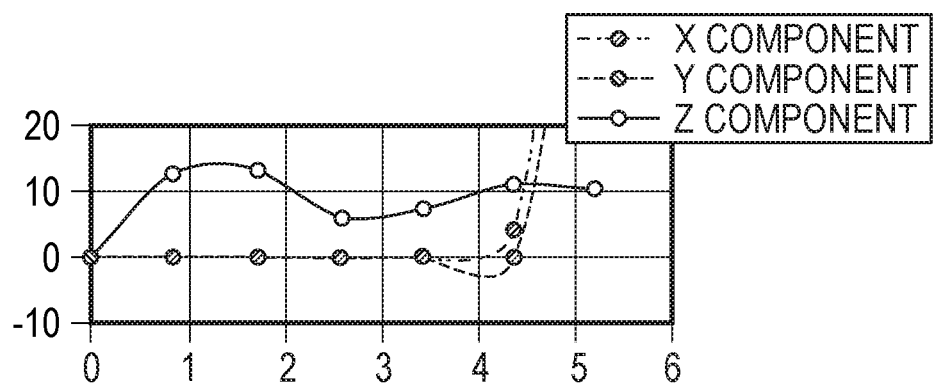
Figure 17C:
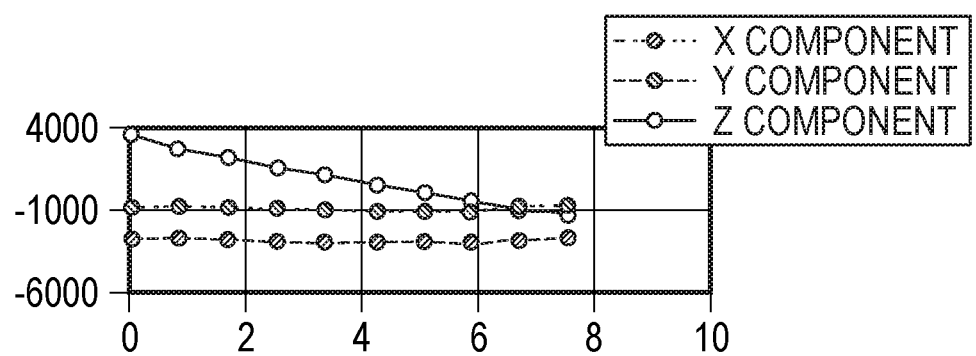
Figure 17D:
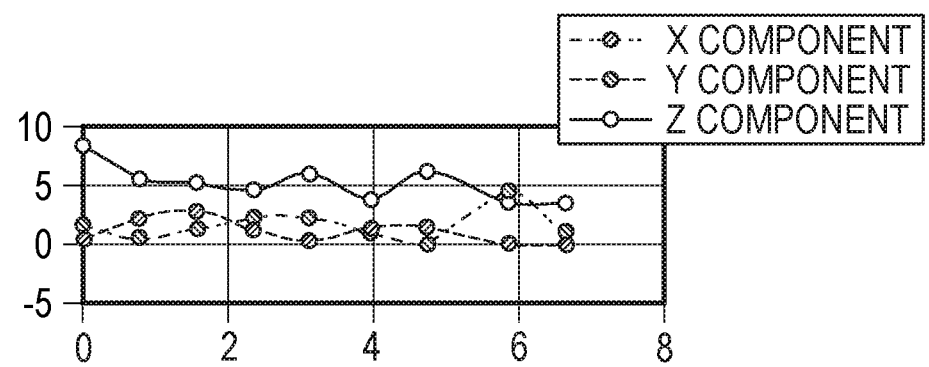

FIGS. 16A-16B illustrate magnetic field strength test data for a rectangular magnet. FIGS. 16C-16F illustrate magnetic field strength test data for a first circular magnet.

FIGS. 17A-17D illustrate magnetic field strength test data for a first circular magnet.

FIGS. 15A-17D illustrate various test data associated with magnets and magnetometers. In the examples of FIG. 15A-15I, field strength can be erratic or inconsistent along a Z axis of the magnetometer. Generally, as a magnet travels along X or Y axes, magnetic field strength drops off quickly, such as around 50 mm laterally away from the magnetometer. When traveling along X and Y directions, the Z component typically peaks and then drops off.

FIGS. 16A-16F illustrate field strength test data corresponding to different magnet types and different lateral offset locations relative to the magnetometer.

Based on the examples of FIGS. 15A-17D it can be seen that several positions can provide acceptable signal to noise ratios (SNR) for each magnet type. A minimum deflection of about 0.5 mm is generally used to achieve a good SNR. Placement of a magnet directly over the magnetometer can be less optimal than other magnet placement locations. In an example, there is potential for multi-duty use of the magnetometer such as by placing magnets to maximize signal on one or two axes and not on others. Such an arrangement could enable an index pulse for spooling, or other functionality.

Various different magnet types and shapes can be used. For example, a neodymium magnet can be used. The magnet can be rectangular, circular, toroidal, small (e.g., about 0.1" diameter by about 0.04" thick), or large (e.g., about 0.25" diameter by about 0.06" thick).

The present inventors have recognized that, to optimize performance of the magnetometer in the context of footwear with a small magnet travel or deflection distance, the magnet should be offset from a Z axis associated with the magnetometer, that is, spaced laterally or sideways from a vertical or Z axis of the magnetometer.

In an example, a footwear article can include or use a capacitive foot presence sensor. A capacitive foot presence sensor can include a surface type sensor or a projective type sensor. A surface type sensor uses capacitive sensors at the corners of a thin film that can be distributed across a sensor surface. In this example, the capacitive sensor surface can include an inside surface of the footwear article, such as on an insole, tongue, footwear article wall, or elsewhere. A projective type sensor can use a grid of conductive elements arranged in rows and columns. In both types, when a body part or foot is located at or proximal to the film and/or conductive elements, an electrical charge can be transferred to the foot to complete a circuit, thereby creating a voltage change.

Figure 18:
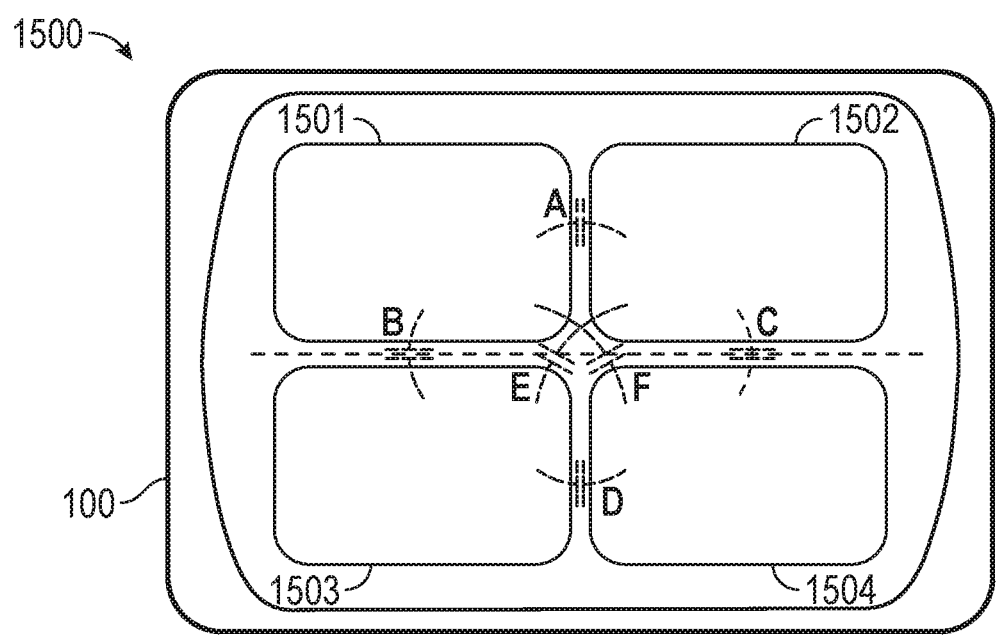
FIG. 18 illustrates a block diagram of a capacitor-based foot presence sensor.

FIG. 18 illustrates generally an example of a capacitive sensor 1500. The capacitive sensor 1500 can include multiple capacitive plates, such as can be arranged on the housing structure 100, for example, to be positioned at or near an underside of a foot when the footwear article including the capacitive sensor 1500 is worn.

The foot presence sensor 1500 can include a plurality of capacitor plates. In the example of FIG. 18, four capacitor plates are identified as 1501-1504. The capacitor plates can be made of a conductive material such as a conductive foil. The foil can be flexible and can optionally be embedded into a plastic of the housing structure 100. It is to be appreciated that any conductive material could be used, such as films, inks, etc.

A capacitance value of a capacitor is functionally related to a dielectric constant of a material between two plates that form a capacitor. Within the sensor 1500, a capacitor can be formed between each pair of two or more of the capacitor plates 1501-1504. Accordingly, there are six effective capacitors formed by the six unique combination pairs of the capacitor plates 1501-1504. Optionally, two or more of the plates can be electrically coupled to form a single plate, That is, first and second capacitor plates 1501 and 1502 can optionally be electrically coupled and used as half of a capacitor with the third and fourth capacitor plates 1503 and 1504 electrically coupled to form the other half.

A capacitive effect between the first and second capacitor plates 1501 and 1502 is represented in FIG. 18 by a phantom capacitor identified by letter A. The capacitive effect between the first and third capacitor plates 1501 and 1503 is represented by the phantom capacitor identified by letter B. The capacitive effect between the second and fourth capacitor plates 1502 and 1504 is represented by the phantom capacitor identified by letter C. The capacitive effect between the third and fourth capacitor plates 1503 and 1504 is represented by the phantom capacitor identified by letter D. The capacitive effect between the second and third capacitor plates 1502 and 1503 is represented by the phantom capacitor identified by letter E. The capacitive effect between the first and fourth capacitor plates 1501 and 1504 is represented by the phantom capacitor identified by letter F. A person of ordinary skill in the art will appreciate that each phantom capacitor is representative of an electrostatic field extending between the respective pair of capacitor plates. Hereinafter, for the purpose of easy identification, the capacitor formed by each pair of capacitive plates is referred to by the same letter (e.g., "A", "B", etc.) used in FIG. 18 to identify the phantom-drawn capacitors.

For each pair of capacitor plates in the example of FIG. 18, an effective dielectric between the plates includes an airgap (or other material) between the plates. Also, for each pair of capacitor plates, any portion of a foot that is proximal to the respective pair of capacitive plates becomes part of the effective dielectric for the given pair of capacitive plates. A dielectric constant between each pair of capacitor plates can be related to a proximity of a foot to the respective pair of plates. For example, the closer a foot is to a given pair of plates, the greater the value of the effective dielectric. As the dielectric constant value increases, the capacitance value increases.

The foot presence sensor can include a plurality of capacitive sensor drive/monitor circuits. A drive/monitor circuit can be associated with each pair of capacitor plates in the example of FIG. 18, In an example, drive/monitor circuits can provide drive signals (e.g., electrical excitation) to the capacitor plate pairs and, in response, can receive capacitance-indicating values. Each drive/monitor circuit can be configured to measure a variable capacitance value of an associated capacitor (e.g., the capacitor "A" corresponding to the first and second plates 1501 and 1502), and can be further configured to provide a signal indicative of the measured capacitance value. The drive/monitor circuits can have any suitable structure for measuring the capacitance.

In an example, capacitance values measured by the drive/monitor circuits can be provided to a controller or processor circuit (see, e.g., the processor circuit of FIG. 10A). An operation of the controller includes providing a lace mechanism actuator. The operation can optionally be performed by discrete, "hard-wired" components, can be performed by a processor executing software, or can be performed by a combination of hard-wired components and software. In an example, the lace mechanism actuation function includes (1) monitoring signals from the drive/monitor circuits, (2) determining which, if any, of the signals indicate a capacitance value in excess of a specified threshold value (e.g., stored in the processor circuit and/or in a memory circuit in data communication with the processor circuit), (3) make a characterization of the location, size, etc. of the foot that is located proximal to the sensor matrix based upon, e.g., a number of threshold values that are exceeded, and (4) permit, alter or suppress actuation of the lace driving mechanism depending upon the characterization.

Figure 19:
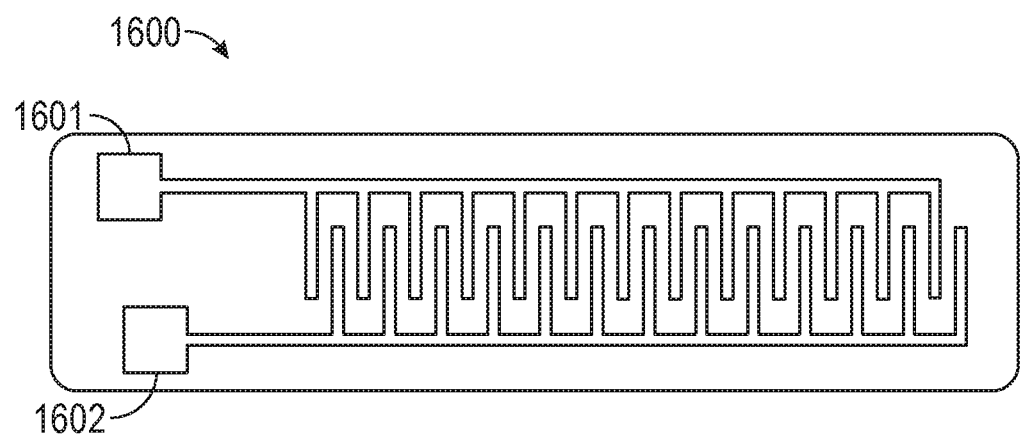
FIG. 19 illustrates generally an example of an electrode configuration for a capacitor-based foot presence sensor.

FIG. 19 illustrates generally an example 1600 of a capacitive electrode configuration. The example includes first and second electrodes 1601 and 1602 arranged along a substantially planar surface, such as in a comb configuration. The processor circuit (see FIG. 8A) can be configured to generate a stimulus signal to apply to the first and second electrodes 1601 and 1602 and to sense a response signal indicative of a change in capacitance between the electrodes. The capacitance can be influenced by the presence of a body or foot relative to the electrodes. For example, the first and second electrodes 1601 and 1602 can be arranged on or near a surface of the housing structure 100, such as proximal to a foot.

In an example, a foot presence sensor includes an etched conductive layer, such as in an X-Y grid to form a pattern of electrodes, or by etching multiple separate, parallel layers of conductive material, for example with perpendicular lines or tracks to form the grid. In this and other capacitive sensors, no direct contact between a body or foot and a conductive layer is needed. The conductive layer can optionally be embedded in the housing structure 100, or can be coated with a protective or insulating layer.

In an example, a capacitive foot sensor is configured to sense or use information about a mutual capacitance among multiple electrodes or plates. Mutual capacitive sensors can include a capacitor at each intersection of each row and each column of an electrode grid. Optionally, the electrode grid is arranged in a single row or column. In an example, a voltage signal can be applied to the rows or columns, and a body or foot near the surface of the sensor changes a local electric field that, in turn, can reduce the mutual capacitance. A capacitance change at every individual point on the grid can be measured to determine a body location, such as by measuring a voltage in each axis. In an example, mutual capacitance measuring techniques can provide information from multiple locations around the grid at the same time.

In an example, a mutual capacitance measurement uses an orthogonal grid of transmit and receive electrodes. In a mutual capacitance sensor system, each detection can be detected as a discrete X-Y coordinate pair. In an example, information from multiple measurements of a capacitive sensor can be used to determine foot presence. In an example, rate of change information about X and/or Y detection coordinates can be used.

In an example, a self-capacitance based foot presence sensor can have the same X-Y grid as a mutual capacitance sensor, but the columns and rows can operate independently. In a self-capacitance sensor, capacitive loading of a body at each column or row can be detected independently.

In an example, capacitive sensors can optionally have electrodes or plates that have a relatively large surface area, and can sense changes in capacitance over a correspondingly large area.

In an example, a foot presence sensor that is capacitor-based can have a baseline or reference capacitance value. The reference capacitance value can be a function of an electrode surface area, or of an electrode placement relative to other footwear components, or of an orientation or environment of the sensor or footwear itself. That is, a sensor can have some associated capacitance value even without a foot present in the footwear, and that value can be a function of a dielectric effect of one or more materials or environmental factors at or near the sensor. In an example, an orthotic insert (e.g., insole) in footwear can change a dielectric characteristic of a capacitive sensor. However, the processor circuit can optionally be configured to calibrate or self-calibrate the capacitive sensor when a baseline or reference characteristic changes, such as when an insole is changed.

The present inventors performed a variety of tests to evaluate an effect of various orthotic inserts on capacitive foot sensing techniques. Full and partial length orthotic insoles were tested. The addition of a regular (partial length) orthotic to the footwear increased an overall dielectric and decreased an electric field sensitivity to the presence of the foot. The signal amplitude also decreased in the presence of the orthotic. The RMS amplitude of the noise was similar with or without the orthotic. The response under loading and unloading conditions was also similar.

Based on results of the orthotics tests, utilizing capacitive sensing for detection of foot presence with regular or full-length orthotics is feasible with respect to signal to noise resolution. With a regular and full length orthotic, under both light and high duty loading conditions, a SNR exceeding a minimum of 6 dB required to resolve foot presence was measured. The auto-calibration of the sensor has adequate offset range to compensate for added dielectric effects of the orthotics.

In the case of the full-length orthotic, the test procedure included removing the production insole, and the orthotic itself was used as the only. The dielectric was nearly equivalent resulting in similar SNR in the compressed state to the no-orthotic case.

Air gaps between the full-length orthotic and the sensing electrode resulted in a measurable variation in SNR as a function of an applied load. Various foot zones behaved similarly under low loading conditions, showing no permanent deformation of the gap distance under the orthotic. Under high loading conditions, such as exerted by standing, can be enough to compress the orthotic arch against the sensor and eliminate a gap. The resulting resultant electric field can be similar in magnitude to the use of the production insole (no orthotic). In an example, this variation can be compensated for, such as by using a gap-filling foam at the underside of the full-length orthotic.

Figure 20A:
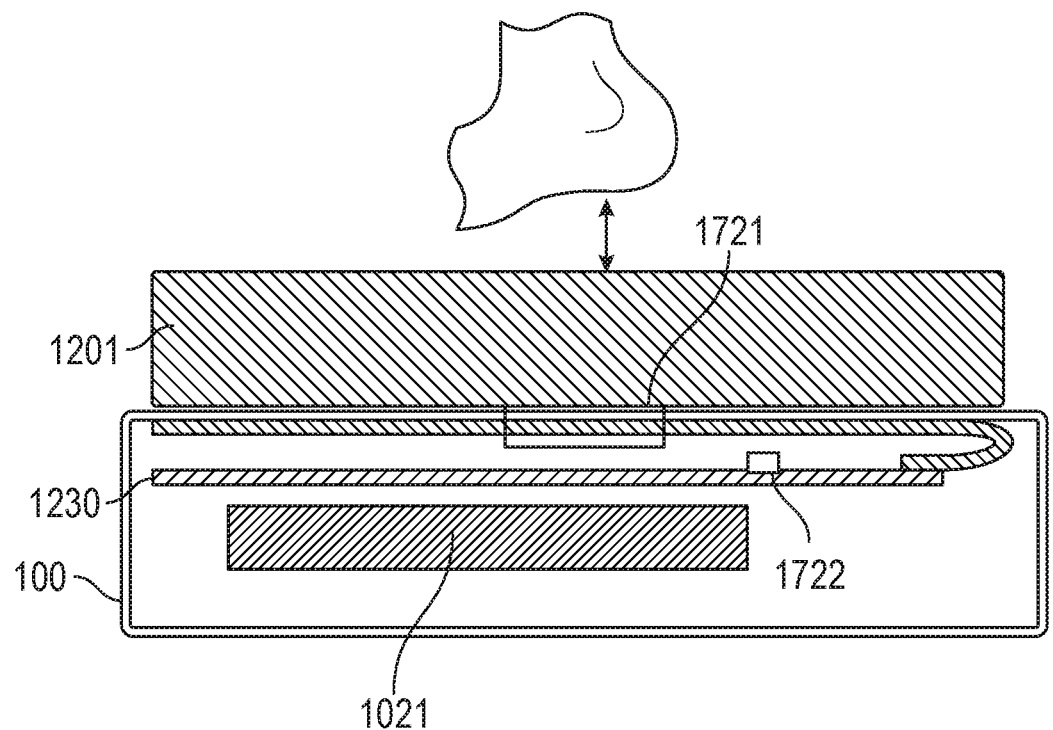

FIG. 20A illustrates generally an example of a capacitive foot presence sensor. The capacitive foot presence sensor can include a capacitive sensing electrode 1721 coupled to a capacitive sensing controller circuit 1722. The electrode 1721 and/or the controller circuit 1722 can optionally be included in or mounted to the housing structure 100.

In an example, the controller circuit 1722 includes an Atmel ATSAML21E18B-MU, ST Microelectronics STM32L476M, or other similar device. As discussed herein, the electrode 1721 can optionally be included in a recess above the housing structure, or as part of the foam insole 1201, or elsewhere.

Figure 20B:
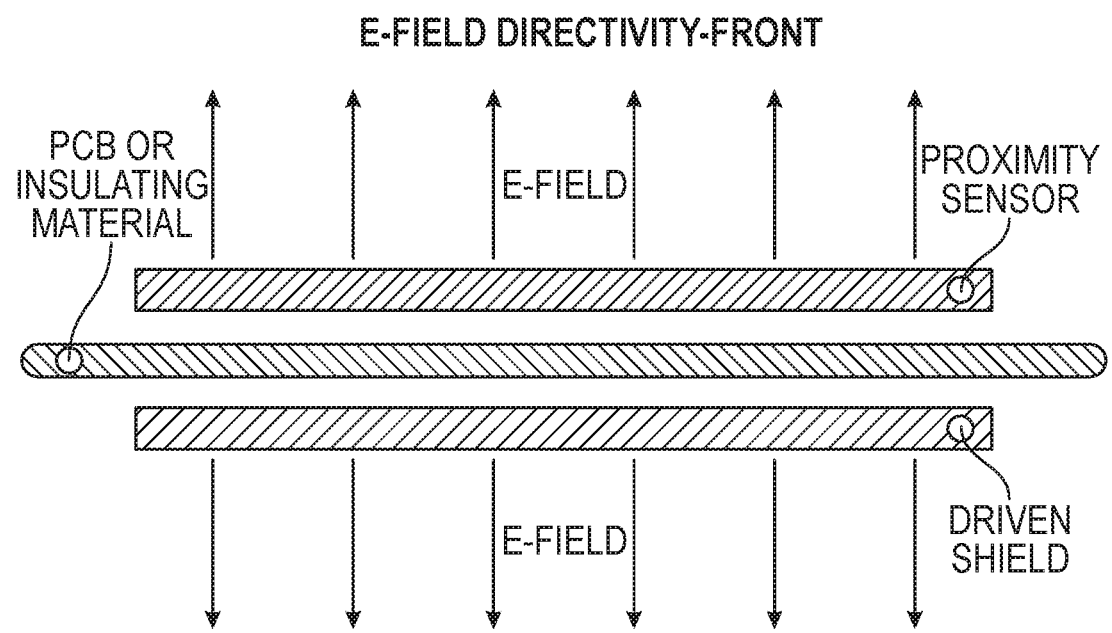

In the example of FIG. 20A, an electric field can project from a top side of the electrode 1721. In an example, an electric field below the electrode can be blocked by placing a driven shield below the sensing electrode (see FIG. 20B). The driven shield and sensing electrode 1721 can be electrically insulated from each other. If the sensing electrode 1721 is on one surface of the PCB or FPC then the driven shield can be on the bottom layer of the PCB or any of the lower inner layers on a multi-layer PCB or FPC. In an example, the driven shield can be of equal or greater surface area of the sensing electrode 1721 and centered directly below the sensing electrode 1721. The shield can be driven to create an electric field of the same polarity, phase and/or amplitude of an x axis leg of the sensing electrode 1721, The shield's field can repel the electric field of the sensing electrode 1721, thereby isolating it from undesired coupling effects, such as to a lower ground plane of the main PCA.

One advantage of using capacitive sensing techniques for detecting foot presence includes that a capacitive sensor can function well even when a capacitive sensor is placed in an arch region and a user has high arches. For example, a preferred integration of a foot presence sensor can include inside of the housing structure 100 such as to protect it from perspiration and dirt. Minimizing or eliminating connections through the housing increases reliability. As described above, a good position in which to locate the housing is in an arch area because it is the least likely to be felt or to cause discomfort to a wearer.

In an example, sensing electrode 1721 can be configured to sense a difference in signal between multiple electrodes, such as between X and Y electrodes. In an example, a suitable sampling frequency can be between about 2 and 50 Hz, Capacitive sensing techniques can also be relatively invariant to perspiration (wetness) on the insole or in a sock around a foot. The effect of such moisture can be to reduce a dynamic range of the detection since the presence of moisture can increase a measured capacitance. However, in some examples, the dynamic range is sufficient to accommodate this effect within expected levels of moisture.

FIG. 20C illustrates generally top (left) and perspective views (right) of a sensing electrode 1725. In this example, the sensing electrode can be configured to be disposed inside of the housing structure 100, such as at or near (e.g., pressed or mounted against or adjacent to) a top inner wall of the housing structure 100. In an example, the sensing electrode 1725 includes a flexible substrate.

Various tests were performed by the present inventors to validate foot presence sensing using capacitive sensing techniques. In an example, capacitive sensing for detection of foot presence is feasible with respect to signal to noise resolution. With a 99.9% confidence, an SNR of 22 dB can be measured. In one series of tests, 16 subjects were used, including 4 female and 12 male. The distribution of foot size was a normal distribution with a range from 5.5 to 12.5. Arch height as self-reported among low, medium, and high, was normally distributed. With an R value of 0.039 there was no correlation between the quality of the signal and the size of the subject's foot.

In an example, a foot presence sensor includes a first pressure sensor. The first pressure sensor can be embedded in the outsole 60, in a footwear side or top component, or elsewhere in the footwear. The first pressure sensor can be configured to sense a change in mass, such as when a user places weight on to the sensor. In an example, the first pressure sensor can include a force-sensitive resistor.

Figure 21A:
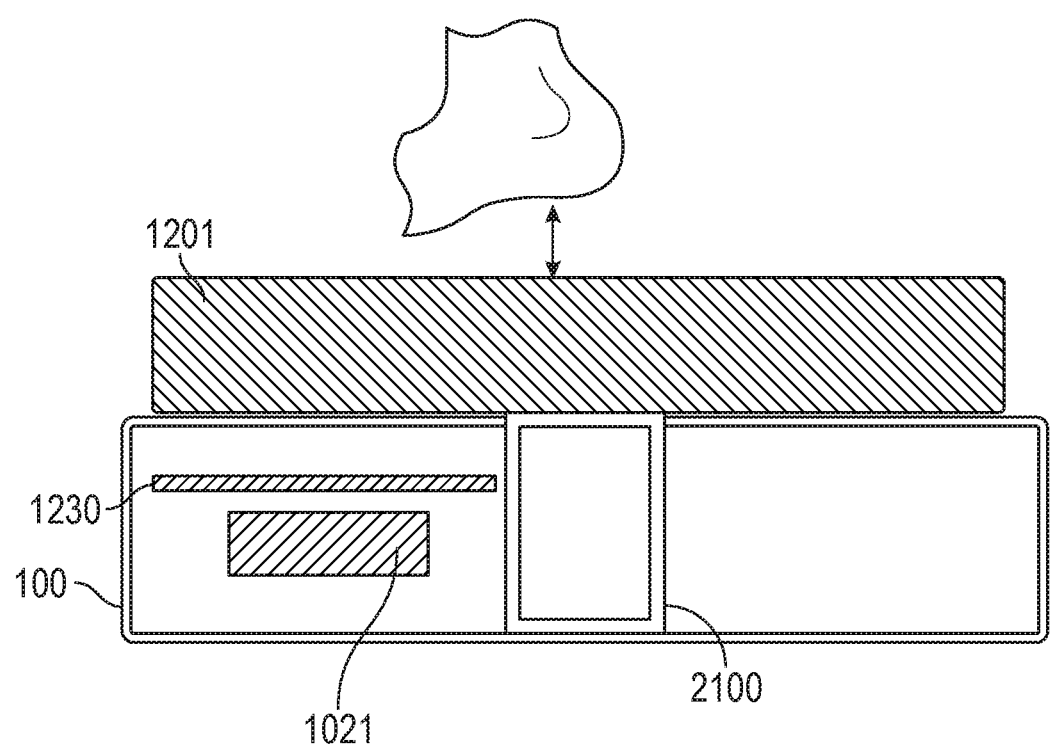
FIGS. 21A and 21B illustrate generally examples of a pressure-based foot presence sensor configuration.

FIG. 21A illustrates generally an example is a block diagram illustrating footwear components that can include a pressure-based foot presence sensor. The example in FIG. 21A includes a pressure sensor enclosure 2100. The pressure sensor enclosure 2100 can be a substantially airtight or liquid-tight enclosure having a measurement membrane disposed therein. The measurement membrane can move or respond to changes in a distribution of a gas or fluid in the enclosure 2100. As shown, the pressure sensor enclosure 2100 can be positioned underfoot and can be configured to receive a physical foot impact when the footwear is worn. In an example, the pressure sensor enclosure 2100 shares a wall with, or is adjacent to a wall of, the housing structure 100. In response to impact from a foot, at least one wall of the enclosure 2100 can move slightly, thereby changing a distribution of gas or fluid in the enclosure. Information from the sensor or membrane about the change in gas or fluid distribution can be received by a processor circuit (e.g., the processor circuit 1020 of FIG. 10A) and used to identify foot presence or foot activity information.

Figure 21B:
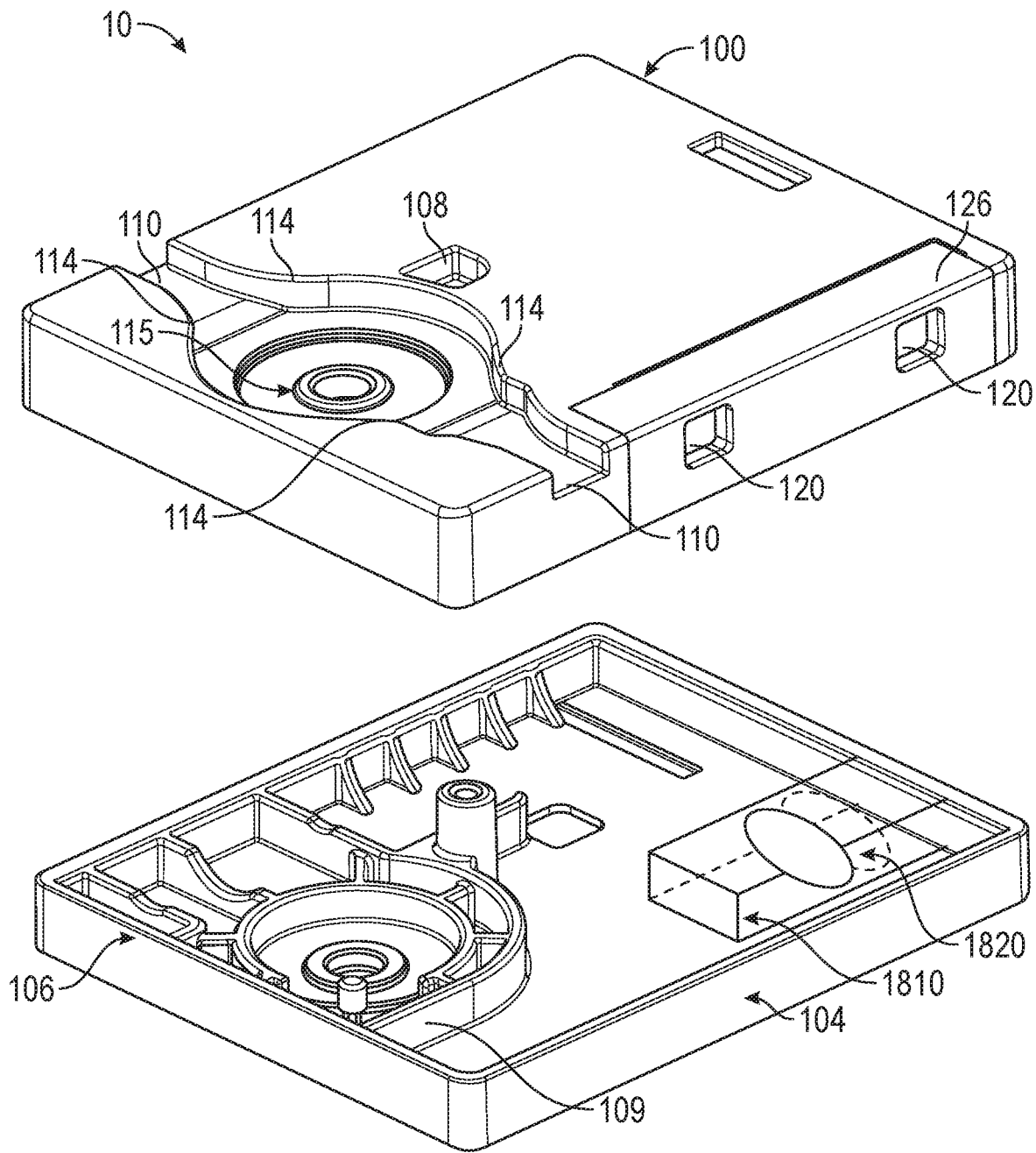

FIG. 21B illustrates generally an example of the lacing engine 10 from FIG. 2B with a second pressure sensor 1820. The second pressure sensor 1820 can be embedded inside of the housing structure 100 of the lacing engine 10. The lacing engine 10 can be substantially vapor sealed or hermetically sealed. That is, the lacing engine 10 can be a substantially closed structure that includes at least a portion that is airtight. In an example, the second pressure sensor 1820 can be embedded in a hermetic chamber 1810, and the hermetic chamber 1810 can be included inside of the housing structure 100. The hermetic chamber 1810 can include a wall or walls that are in contact with or shared by the housing structure 100.

In an example, the second pressure sensor 1820 includes a membrane that is embedded in the hermetic chamber 1810. When subjected to force, such as when a user applies weight to the footwear article when standing or walking, one or more sides of the hermetic chamber 1810 can deflect or bend, thus changing a distribution of gas inside of the hermetic chamber 1810. The membrane of the second pressure sensor 1820 can move in response to such a gas distribution change and can generate a sensor signal indicative of the membrane movement. The sensor signal from the second pressure sensor 1820 can thus indicate that a foot is present when membrane movement is detected.

In an example, information from a foot presence sensor or magnetometer can be used as a pedometer. For example, changes in a time-varying magnetic field signal from the magnetometer 1220 can indicate that a footwear article is in motion. Optionally, the information from the magnetometer can be used or processed together with other sensor information, such as with accelerometer or temperature information, to help determine when a step event occurs. The processor circuit (see, e.g., the processor circuit 1020 of FIG. 10A) can be used to receive the magnetometer signal and, in response, determine information about a number of steps taken by the wearer. Further to its use as a pedometer, information from a magnetometer can be used to determine a rate or travel.

In an example, a magnetometer can be configured to monitor a physiological characteristic of a wearer. For example, the sensor can provide information about a foot expansion or contraction characteristic, a pulsatile characteristic detected from pressure changes of a foot itself, or other physiologic information.

In an example, a magnetometer can provide information about displacement or force. When sensor information includes displacement information, information about a foot strike can be obtained. Foot strike information can include information about a force or impact of a foot in footwear. For example, the foot strike information can be used to determine whether a wearer is walking (low impact, low force), running (medium impact, medium force), or jumping (high impact, high force).

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Although an overview of the inventive subject matter has been described with reference to specific example embodiments, various modifications and changes may be made to these embodiments without departing from the broader scope of embodiments of the present disclosure. Such embodiments of the inventive subject matter may be referred to herein, individually or collectively, by the term "invention" merely for convenience and without intending to voluntarily limit the scope of this application to any single disclosure or inventive concept if more than one is, in fact, disclosed.

The embodiments illustrated herein are described in sufficient detail to enable those skilled in the art to practice the teachings disclosed. Other embodiments may be used and derived therefrom, such that structural and logical substitutions and changes may be made without departing from the scope of this disclosure. The disclosure, therefore, is not to be taken in a limiting sense, and the scope of various embodiments includes the full range of equivalents to which the disclosed subject matter is entitled.

The following Aspects provide a non-limiting overview of the footwear and foot presence or position sensing systems and methods discussed herein.

Aspect 1 can include or use subject matter (such as an apparatus, a system, a device, a method, a means for performing acts, or a device readable medium including instructions that, when performed by the device, can cause the device to perform acts), such as can include or use an article of footwear comprising a ferromagnetic body disposed in the article, and a magnetometer configured to measure a strength or direction of a magnetic field that is influenced by a position of the ferromagnetic body. In Aspect 1, one of the ferromagnetic body and the magnetometer can be configured to move relative to the other one of the ferromagnetic body and the magnetometer according to movement of a foot in the article or according to movement of the article itself.

Aspect 2 can include or use, or can optionally be combined with the subject matter of Aspect 1, to optionally include or use a processor circuit, wherein the magnetometer is configured to generate a magnetometer signal that indicates the position of the ferromagnetic body, and wherein the processor circuit is configured to receive the magnetometer signal from the magnetometer.

Aspect 3 can include or use, or can optionally be combined with the subject matter of Aspect 2, to optionally include, when the magnetometer signal indicates a specified change in the position of the ferromagnetic body, the processor circuit is configured to initiate data collection from one or more other sensors in or associated with the article of footwear.

Aspect 4 can include or use, or can optionally be combined with the subject matter of one or any combination of Aspects 2 or 3 to optionally include, when the magnetometer signal indicates a specified change in the position of the ferromagnetic body, the processor circuit is configured to actuate a drive mechanism to tighten or loosen the article of footwear about the foot.

Aspect 5 can include or use, or can optionally be combined with the subject matter of one or any combination of Aspects 2 through 4 to optionally include the magnetometer is configured to generate a time-varying magnetometer signal that indicates the position of the ferromagnetic body while the article is worn and moved by a foot, and wherein the processor circuit is configured to determine a foot impact characteristic based on the time-varying magnetometer signal.

Aspect 6 can include or use, or can optionally be combined with the subject matter of Aspect 5, to optionally include or use the processor circuit is configured to determine a foot impact force characteristic or step timing characteristic based on the time-varying magnetometer signal.

Aspect 7 can include or use, or can optionally be combined with the subject matter of one or any combination of Aspects 5 or 6 to optionally include the processor circuit is configured to determine the foot impact characteristic for a single step event.

Aspect 8 can include or use, or can optionally be combined with the subject matter of one or any combination of Aspects 5 through 7 to optionally include the processor circuit is configured to determine a rate of change of the time-varying magnetometer signal and, based on the determined rate of change, characterize a step force or a step frequency.

Aspect 9 can include or use, or can optionally be combined with the subject matter of one or any combination of Aspects 1 through 8 to optionally include the magnetometer configured to generate a magnetometer signal that includes information about a change in the magnetic field when the article is worn and at least one of the ferromagnetic body and the magnetometer is moved relative to the other by a foot.

Aspect 10 can include or use, or can optionally be combined with the subject matter of one or any combination of Aspects 1 through 9 to optionally include or use the magnetometer configured to sense information about a change in an ambient magnetic field in response to an influence of the foot itself on the ambient magnetic field.

Aspect 11 can include or use, or can optionally be combined with the subject matter of one or any combination of Aspects 1 through 10 to optionally include the ferromagnetic body or the magnetometer is configured to move relative to the other of the ferromagnetic body or the magnetometer when the article is worn or moved.

Aspect 12 can include or use, or can optionally be combined with the subject matter of one or any combination of Aspects 1 through 11 to optionally include or use multiple ferromagnetic bodies disposed in the article and spaced apart from the magnetometer, and wherein at least one of the multiple bodies is configured to move relative to the magnetometer when the article is worn or moved.

Aspect 13 can include or use, or can optionally be combined with the subject matter of one or any combination of Aspects 1 through 12 to optionally include or use the magnetometer being a three-axis magnetometer that is configured to provide information about a change in the magnetic field in at least x, y, and z dimensions.

Aspect 14 can include or use, or can optionally be combined with the subject matter of one or any combination of Aspects 1 through 13 to optionally include or use the ferromagnetic body being embedded in a compressible material that is configured to be worn underfoot in the article of footwear.

Aspect 15 can include or use, or can optionally be combined with the subject matter of Aspect 14, to optionally include or use the magnetometer being configured to be disposed underfoot and in an arch region of the article.

Aspect 16 can include or use, or can optionally be combined with the subject matter of one or any combination of Aspects 14 or 15 to optionally include or use the magnetometer being configured to be disposed underfoot and in a heel or toe region of the article.

Aspect 17 can include or use, or can optionally be combined with the subject matter of one or any combination of Aspects 1 through 16 to optionally include or use a bridge component, wherein at least one of the ferromagnetic body and the magnetometer is coupled to the bridge component, and wherein the bridge component biases the at least one of the ferromagnetic body and the magnetometer away from the other one of the ferromagnetic body and the magnetometer when the ferromagnetic body and the magnetometer are in a relaxed state or reference position.

Aspect 18 can include or use, or can optionally be combined with the subject matter of Aspect 17, to optionally include or use a spring coupled to the bridge component, wherein the spring biases the bridge component to a first location.

Aspect 19 can include or use, or can optionally be combined with the subject matter of one or any combination of Aspects 17 or 18 to optionally include or use the bridge component being rigid or semi-rigid, and wherein the bridge component is configured to receive a foot arch displacement force and, in response, to correspondingly displace one of the ferromagnetic body and the magnetometer relative to its reference position.

Aspect 20 can include or use, or can optionally be combined with the subject matter of one or any combination of Aspects 17 or 18 to optionally include or use the bridge component being rigid or semi-rigid, and wherein the bridge component is configured to receive a foot displacement force from a foot from other than a central arch region of the foot and, in response, to correspondingly displace one of the ferromagnetic body and the magnetometer relative to its reference position.

Aspect 21 can include or use, or can optionally be combined with the subject matter of one or any combination of Aspects 1 through 20 to optionally include or use the ferromagnetic body being laterally offset from a first axis of the magnetometer.

Aspect 22 can include or use, or can optionally be combined with the subject matter of one or any combination of Aspects 1 through 21 to optionally include or use the ferromagnetic body having one of a circle, rectangle, or torpid shape.

Aspect 23 can include or use, or can optionally be combined with the subject matter of one or any combination of Aspects 1 through 22 to optionally include or use a lacing mechanism disposed in an arch region of the article of footwear, and wherein the lacing mechanism is actuated based on information from the magnetometer about the position of the ferromagnetic body.

Aspect 24 can include or use, or can optionally be combined with the subject matter of one or any combination of Aspects 1 through 23 to optionally include or use a processor circuit configured to determine a strike force of a step using the measured strength or direction of the magnetic field.

Aspect 25 can include or use, or can optionally be combined with the subject matter of one or any combination of Aspects 1 through 24 to optionally include or use a processor circuit configured to determine a step interval or a step count from the measured strength or direction of the magnetic field.

Aspect 26 can include or use, or can optionally be combined with the subject matter of one or any combination of Aspects 1 through 25 to optionally include or use a processor circuit configured to determine, from the measured strength or direction of the magnetic field, a shear stress or a shear displacement of the foot relative to the article of footwear.

Aspect 27 can include or use subject matter (such as an apparatus, a system, a device, a method, a means for performing acts, or a device readable medium including instructions that, when performed by the device, can cause the device to perform acts), such as can include or use an article of footwear with an automatic lacing system, the article comprising a mid-sole including a cavity, a motor disposed in the cavity, an insole disposed over the mid-sole, a plurality of straps configured to adjust a tightness or looseness characteristic of the article about a foot when the article is worn, wherein the plurality of straps are configured to move between tightened and loosened positions in response to activity of the motor, a ferromagnetic body disposed in the article, and at least one sensor configured to sense a location change of the ferromagnetic body in response to compression of the insole by a foot when the article is worn. In Aspect 27, the motor is coupled to the sensor (e.g., by way of a processor circuit) and the motor is configured to respond to a sensed change in the location of the ferromagnetic body by adjusting a tension of the straps.

Aspect 28 can include or use, or can optionally be combined with the subject matter of Aspect 27, to optionally include or use the at least one sensor includes a magnetometer configured to sense a change in a magnetic field, the change due at least in part to the location change of the ferromagnetic body, and wherein one of the ferromagnetic body and the magnetometer is substantially fixed relative to a housing or wall of the article, and wherein the other one of the ferromagnetic body and the magnetometer is movable with respect to the housing or wall of the article.

Aspect 29 can include or use, or can optionally be combined with the subject matter of Aspect 28, to optionally include the insole is compressible by a foot, and the ferromagnetic body is coupled to the insole and moves according to compression of the insole by the foot.

Aspect 30 can include or use, or can optionally be combined with the subject matter of one or any combination of Aspects 27 through 29 to optionally include or use a processor circuit coupled to the at least one sensor, and wherein the processor circuit is configured to determine rate of change information about the sensed location change of the ferromagnetic body.

Aspect 31 can include or use subject matter (such as an apparatus, a system, a device, a method, a means for performing acts, or a device readable medium including instructions that, when performed by the device, can cause the device to perform acts), such as can include or use a magnetic foot position sensor (FPS) for use in an article of footwear, the FPS comprising a bridge configured to be worn below or near an arch of a foot, wherein the bridge is configured to move in vertical or lateral directions in response to pressure applied to the bridge from the foot, and a first magnetic body coupled to the bridge, and a magnetometer spaced apart from the first magnetic body and configured to provide a signal indicative of displacement of the first magnetic body relative to the magnetometer when the article is worn and the bridge is moved according to movement of a foot.

Aspect 32 can include or use, or can optionally be combined with the subject matter of Aspect 31, to optionally include or use the magnetometer being a multiple-axis magnetometer that is configured to provide a signal indicative of displacement of the first magnetic body along one or more of the multiple axes.

Aspect 33 can include or use, or can optionally be combined with the subject matter of one or any combination of Aspects 31 or 32 to optionally include or use the magnetometer being configured to provide the signal indicative of displacement of the first magnet in response to a vertical or lateral displacement of the first magnetic body relative to the magnetometer.

Aspect 34 can include or use, or can optionally be combined with the subject matter of one or any combination of Aspects 31 through 33 to optionally include or use a second magnetic body, wherein the magnetometer is spaced apart from the second magnetic body and is configured to provide a signal indicative of displacement of either or both of the first and second magnetic bodies relative to the magnetometer.

Aspect 35 can include or use, or can optionally be combined with the subject matter of one or any combination of Aspects 31 through 34 to optionally include or use a spring mechanism that biases the bridge and the first magnetic body away from the magnetometer.

Each of these non-limiting Aspects can stand on its own, or can be combined in various permutations or combinations with one or more of the other Aspects and examples discussed herein.

As used herein, the term "or" may be construed in either an inclusive or exclusive sense. Moreover, plural instances may be provided for resources, operations, or structures described herein as a single instance. Additionally, boundaries between various resources, operations, modules, engines, and data stores are somewhat arbitrary, and particular operations are illustrated in a context of specific illustrative configurations. Other allocations of functionality are envisioned and may fall within a scope of various embodiments of the present disclosure. In general, structures and functionality presented as separate resources in the example configurations may be implemented as a combined structure or resource. Similarly, structures and functionality presented as a single resource may be implemented as separate resources. These and other variations, modifications, additions, and improvements fall within a scope of embodiments of the present disclosure as represented by the appended claims. The specification and drawings are, accordingly, to be regarded in an illustrative rather than a restrictive sense.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein, such as the motor control examples, can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. An Abstract, if provided, is included to comply with 37 C.F.R. § 1.72(b), to allow the reader to quickly ascertain the nature of the technical disclosure. It is submitted with the understanding that it will not be used to interpret or limit the scope or meaning of the claims. Also, in the above Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An article of footwear with an automatic lacing system, the article comprising:
a mid-sole including a cavity;
a motor disposed in a motor housing inside the cavity;
an insole disposed over the mid-sole;
a plurality of straps configured to adjust a tightness or looseness characteristic of the article about a foot when the article is worn, wherein the plurality of straps are configured to move between tightened and loosened positions in response to activity of the motor;
a ferromagnetic body disposed in the article;
at least one sensor configured to sense a location of the ferromagnetic body;
a bridge assembly coupled to the motor housing and to the ferromagnetic body, the bridge assembly including a biasing element that biases the ferromagnetic body away from the at least one sensor and away from the motor housing; and
a processor circuit configured to receive a sensor signal from the at least one sensor, the sensor signal indicative of a location change of the ferromagnetic body in response to compression of the insole by a foot, and the processor circuit is configured to determine a rate of change of the location of the ferromagnetic body;

wherein the motor is coupled to the processor circuit and the motor is configured to respond to the determined rate of change of the location of the ferromagnetic body by adjusting a tension of the straps.

2. The article of claim 1, wherein the at least one sensor includes a magnetometer configured to sense a change in a magnetic field, the change due at least in part to the location change of the ferromagnetic body, and wherein one of the ferromagnetic body or the magnetometer is fixed relative to a housing or wall of the article, and wherein the other one of the ferromagnetic body or the magnetometer is movable with respect to the housing or wall of the article.

3. The article of claim 2, wherein the insole is compressible by a foot, and wherein the ferromagnetic body is coupled to the insole and moves according to compression of the insole by the foot.

4. The article of claim 1, wherein the processor circuit is configured to determine a gait characteristic based on the rate of change of the location of the ferromagnetic body.

5. The article of claim 1, wherein the processor circuit is configured to determine an injury recovery characteristic based on the rate of change of the location of the ferromagnetic body.

6. The article of claim 1, wherein the bridge assembly comprises a bridge plate and a spring, wherein the spring is coupled between the bridge plate and the motor housing, and wherein the ferromagnetic body is coupled to the bridge plate.

7. An article of footwear with an automatic lacing system, the article comprising:
    a mid-sole including a cavity;
    a motor disposed in a motor housing inside the cavity;
    an insole disposed over the mid-sole;
    a plurality of straps configured to adjust a tightness or looseness characteristic of the article about a foot when the article is worn, wherein the plurality of straps are configured to move between tightened and loosened positions in response to activity of the motor;
    a ferromagnetic body disposed in the article;
    at least one sensor configured to sense a location of the ferromagnetic body;
    a bridge assembly coupled to the motor housing and to the ferromagnetic body, the bridge assembly including a biasing element that biases the ferromagnetic body away from the at least one sensor; and
    a processor circuit configured to receive a sensor signal from the at least one sensor, the sensor signal indicative of a location of the ferromagnetic body in response to compression of the insole by a foot, and the processor circuit further configured to control the motor to adjust a tension of the straps when the sensor signal indicates a change in the location of the ferromagnetic body.

8. The article of claim 7, wherein the at least one sensor comprises a magnetometer spaced apart from the ferromagnetic body and configured to provide a signal indicative of displacement of the ferromagnetic body relative to the magnetometer when the article is worn and the bridge assembly is moved according to movement of a foot.

9. The article of claim 8, wherein the magnetometer is a multiple-axis magnetometer that is configured to provide a signal indicative of displacement of the ferromagnetic body along one or more of the multiple axes.

10. The article of claim 8, wherein the magnetometer is configured to provide a signal indicative of displacement of the ferromagnetic body in response to a vertical or lateral displacement of the ferromagnetic body relative to the magnetometer.

11. The article of claim 7, wherein the bridge assembly comprises a bridge plate and a spring, wherein the spring is coupled between the bridge plate and the motor housing, and wherein the ferromagnetic body is coupled to the bridge plate.

12. The article of claim 7, wherein the processor circuit is configured to determine a gait characteristic based on the change in the location of the ferromagnetic body.

13. The article of claim 7, wherein the processor circuit is configured to determine an injury recovery characteristic based on the change in the location of the ferromagnetic body.

14. An article of footwear with an automatic lacing system, the article comprising:
    an insole;
    a motor disposed in a motor housing inside of a cavity under the insole;
    laces configured to adjust a tightness or looseness characteristic of the article about a foot when the article is worn, wherein the laces are configured to move between tightened and loosened positions in response to activity of the motor;
    a ferromagnetic body disposed in the article;
    a sensor configured to sense a location of the ferromagnetic body;
    a bridge assembly coupled to the motor housing and to the ferromagnetic body, the bridge assembly including a biasing element that biases the ferromagnetic body away from the sensor; and
    a processor circuit configured to receive a sensor signal from the sensor, the sensor signal indicative of a location of the ferromagnetic body in response to compression of the insole by a foot, and the processor circuit further configured to control the motor to adjust a tension of the straps when the sensor signal indicates a change in the location of the ferromagnetic body.

15. The article of claim 14, wherein the sensor comprises a magnetometer spaced apart from the ferromagnetic body and configured to provide a signal indicative of displacement of the ferromagnetic body relative to the magnetometer when the article is worn and the bridge assembly is moved according to movement of a foot.

16. The article of claim 14, wherein the bridge assembly comprises a bridge plate and a spring, wherein the spring is coupled between the bridge plate and the motor housing, and wherein the ferromagnetic body is coupled to the bridge plate.

17. The article of claim 14, wherein the processor circuit is configured to determine a gait characteristic based on the change in the location of the ferromagnetic body.

18. The article of claim 14, wherein the processor circuit is configured to determine an injury recovery characteristic based on the change in the location of the ferromagnetic body.

19. The article of claim 14, wherein the processor circuit is configured to determine a foot impact force characteristic or a step timing characteristic based on the sensor signal.

20. The article of claim 14, wherein the processor circuit is configured to determine a step force or step frequency based on the sensor signal.

* * * * *